United States Patent
Harvey et al.

(10) Patent No.: US 11,292,840 B2
(45) Date of Patent: Apr. 5, 2022

(54) METHODS OF TREATING CANCER IN A SUBJECT HAVING ELEVATED ICOS AND/OR T-BET LEVELS OF CD+4 CELLS BY ADMINISTERING AN ICOS AGONIST

(71) Applicant: Jounce Therapeutics, Inc., Cambridge, MA (US)

(72) Inventors: Christopher Harvey, Boston, MA (US); Deborah Law, Hillsborough, CA (US); Amanda Elizabeth Hanson, Newton, MA (US); Martin Yu Fan, Boston, MA (US)

(73) Assignee: Jounce Therapeutics, Inc., Cambridge, MA (US)

( * ) Notice: Subject to any disclaimer, the term of this patent is extended or adjusted under 35 U.S.C. 154(b) by 205 days.

(21) Appl. No.: 16/411,744

(22) Filed: May 14, 2019

(65) Prior Publication Data
US 2019/0367613 A1 Dec. 5, 2019

Related U.S. Application Data

(60) Provisional application No. 62/827,312, filed on Apr. 1, 2019, provisional application No. 62/750,026, filed on Oct. 24, 2018, provisional application No. 62/679,346, filed on Jun. 1, 2018, provisional application No. 62/671,181, filed on May 14, 2018.

(51) Int. Cl.
C07K 16/28 (2006.01)

(52) U.S. Cl.
CPC ...... *C07K 16/2812* (2013.01); *C07K 16/2896* (2013.01); *C07K 2317/24* (2013.01); *C07K 2317/33* (2013.01); *C07K 2317/73* (2013.01); *C07K 2317/75* (2013.01); *C07K 2317/76* (2013.01); *C07K 2317/92* (2013.01)

(58) Field of Classification Search
CPC ............ C07K 16/2812; C07K 16/2896; C07K 2317/73; C07K 2317/75; C07K 2317/76
See application file for complete search history.

(56) References Cited

U.S. PATENT DOCUMENTS 10,570,203 B2 * 2/2020 Sazinsky ................. A61P 35/00

FOREIGN PATENT DOCUMENTS

| CA | 3032897 A1 | 2/2018 |
|---|---|---|
| WO | WO-2012/131004 A2 | 10/2012 |
| WO | WO-2017/070423 A1 | 4/2017 |
| WO | WO-2018/029474 A2 | 2/2018 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Ara et al., "Potent activity of soluble B7RP-1-Fc in therapy of murine tumors in syngeneic hosts," Int J Cancer. 103(4):501-7 (2003).
Arimura et al., "A co-stimulatory molecule on activated T cells, H4/ICOS, delivers specific signals in T(h) cells and regulates their responses," Int Immunol. 14(6):555-66 (2002).
Bailey et al., "Human $CD26^{high}$ T Cells elicit tumor immunity against multiple malignancies via enhanced migration and persistence," Nat Commun. 8(1):1961 (2017) (13 pages).
Bakkour et al., "Mapping of the ICOS binding surface of murine B7h using an unbiased, cellular library of B7h mutants created by cyclical packaging rescue," J Immunol Methods. 332(1-2):151-61 (2008).
Beier et al., "Induction, binding specificity and function of human ICOS," Eur J Immunol. 30(12):3707-17 (2000).
Bertino et al., "Roquin paralogs add a new dimension to ICOS regulation," Immunity. 38(4):624-6 (2013).
Carmi et al., "Tumor-binding antibodies and tumor immunity," Oncotarget. 6(34):35129-30 (2015).
Carthon et al., "Preoperative CTLA-4 blockade: tolerability and immune monitoring in the setting of a presurgical clinical trial," Clin Cancer Res. 16(10):2861-71 (2010).
Chattopadhyay et al., "Structural basis of inducible costimulator ligand costimulatory function: determination of the cell surface oligomeric state and functional mapping of the receptor binding site of the protein," J Immunol. 177(6):3920-9 (2006).
Chen et al., "Anti-CTLA-4 therapy results in higher $CD4^+ICOS^{hi}$ T cell frequency and IFN-gamma levels in both nonmalignant and malignant prostate tissues," Proc Natl Acad Sci U S A. 106(8):2729-34 (2009).
Chen et al., "CD4 T cells require ICOS-mediated PI3K signaling to increase T-Bet expression in the setting of anti-CTLA-4 therapy," Cancer Immunol Res. 2(2):167-76 (2013).
Clinical Protocol MDX1106-02 Amendment 04, "A Phase 1, Double-blind, Randomized, Multicenter, Placebo-controlled, Safety and Pharmacokinetic Dose-escalation Study of a Single Intravenous Administration of MDX-1106, a Fully Human Monoclonal Antibody to PD-1, in Subjects with Active Hepatitis C Genotype 1 Infection," Medarex, Inc. (2009) (92 pages).
Di Giacomo et al., "Long-term survival and immunological parameters in metastatic melanoma patients who responded to ipilimumab 10 mg/kg within an expanded access programme," Cancer Immunol Immunother. 62(6):1021-8 (2013).
Dianzani et al., "B7h Triggering Inhibits the Migration of Tumor Cell Lines," J Immunol. 192(10):1-11 (2014) (12 pages).
Dulos et al., "PD-1 Blockade Augments Th1 and Th17 and Suppresses Th2 Responses in Peripheral Blood from Patients With Prostate and Advanced Melanoma Cancer," J Immunother. 35(2):169-78 (2012).

(Continued)

*Primary Examiner* — Robert S Landsman
(74) *Attorney, Agent, or Firm* — Clark & Elbing LLP; Susan M. Michaud

(57) ABSTRACT

The invention provides methods of treating cancer and methods for selecting treatment approaches for cancer.

19 Claims, 25 Drawing Sheets
Specification includes a Sequence Listing.

(56) References Cited

OTHER PUBLICATIONS

Faget et al., "ICOS-ligand expression on plasmacytoid dendritic cells supports breast cancer progression by promoting the accumulation of immunosuppressive CD4+ T cells," Cancer Res. 72(23) (2012) (37 pages).
Fu et al., "The ICOS/ICOSL pathway is required for optimal antitumor responses mediated by anti-CTLA-4 therapy," Cancer Res. 71 (16):5445-54 (2011).
Goldberg et al., "Pembrolizumab for patients with melanoma or non-small-cell lung cancer and untreated brain metastases: early analysis of a non-randomised, open-label, phase 2 trial," Lancet Oncol. 17(7):976-983 (2016).
Harada et al., "A single amino acid alteration in cytoplasmic domain determines IL-2 promoter activation by ligation of CD28 but not inducible costimulator (ICOS)," J Exp Med. 197(2):257-62 (2003).
Heissmeyer et al., "Molecular control of Tfh-cell differentiation by Roquin family proteins," Immunol Rev. 253(1):273-89 (2013).
Hu et al., "Noncanonical NF-kappaB regulates inducible costimulator (ICOS) ligand expression and T follicular helper cell development," Proc Natl Acad Sci U S A. 108(31):12827-32 (2011).
Hutloff et al., "ICOS is an inducible T-cell co-stimulator structurally and functionally related to CD28," Nature. 397(6716):263-6 (1999).
Kaufman et al., "Natalizumab treatment shows no clinically meaningful effects on immunization responses in patients with relapsing-remitting multiple sclerosis," J Neurol Sci. 341:22-27 (2014).
Khayyamian et al., "ICOS-ligand, expressed on human endothelial cells, costimulates Th1 and Th2 cytokine secretion by memory CD4+ T cells," Proc Natl Acad Sci U S A. 99(9):6198-203 (2002).
Kohrt et al., "Immunodynamics: a cancer immunotherapy trials network review of immune monitoring in immuno-oncology clinical trials," J Immunother Cancer. 4(15):1-16 (2016).
Kosuge et al., "Induction of immunologic tolerance to cardiac allograft by simultaneous blockade of inducible co-stimulator and cytotoxic T-lymphocyte antigen 4 pathway," Transplantation. 75(8):1374-80 (2003).
Liakou et al., "CTLA-4 blockade increases IFNgamma-producing CD4+ICOS$^{hi}$ cells to shift the ratio of effector to regulatory T cells in cancer patients," Proc Natl Acad Sci U S A. 105(39):14987-92 (2008).
Ling et al., "Differential expression of inducible costimulator-ligand splice variants: lymphoid regulation of mouse GL50-B and human GL50 molecules," J Immunol. 166(12):7300-8 (2001).
Lischke et al., "Comprehensive analysis of CD4+ T cells in the decision between tolerance and immunity in vivo reveals a pivotal role for ICOS," J Immunol. 189(1):234-44 (2012).
Mages et al., "Molecular cloning and characterization of murine ICOS and identification of B7h as ICOS ligand," Eur J Immunol. 30(4):1040-7 (2000).
Martin-Orozco et al., "Melanoma cells express ICOS ligand to promote the activation and expansion of T-regulatory cells," Cancer Res. 70(23):9581-90 (2010).
McAdam et al., "Mouse inducible costimulatory molecule (ICOS) expression is enhanced by CD28 costimulation and regulates differentiation of CD4+ T cells," J Immunol. 165(9):5035-40 (2000).
Muranski et al., "Adoptive immunotherapy of cancer using CD4+ T cells," Curr Opin Immunol. 21(2):200-8 (2009) (15 pages).
Nabeyama et al., "Beneficial effects of costimulatory blockade with anti-inducible costimulator antibody in conjunction with CTLA4Ig on prevention of islet xenograft rejection from rat to mouse," Transplantation. 78(11):1590-6 (2004).
Nakamura et al., "Acceptance of islet allografts in the liver of mice by blockade of an inducible costimulator," Transplantation. 75(8):1115-8 (2003).
Patil et al., "Precursors of human CD4+ cytotoxic T lymphocytes identified by single-cell transcriptome analysis," Sci. Immunol. 3(19):eaan8664 (2018) (14 pages).
Protocol for 'Brahmer et al., "Safety and activity of anti-PD-L1 antibody in patients with advanced cancer," N Engl J Med. 366(26):2455-65 (2012)', (946 pages).
Riley et al., "Modulation of TCR-induced transcriptional profiles by ligation of CD28, ICOS, and CTLA-4 receptors," Proc Natl Acad Sci USA. 99(18):11790-5 (2002).
Rodig et al., "MHC proteins confer differential sensitivity to CTLA-4 and PD-1 blockade in untreated metastatic melanoma," Sci Transl Med. 10(450):eaar3342 (2018) (14 pages).
Sakthivel et al., "Attenuation of immune-mediated influenza pneumonia by targeting the inducible co-stimulator (ICOS) molecule on T cells," PLoS One. 9(7):e100970, p. 1-11 (2014).
Sim et al., "IL-2 therapy promotes suppressive ICOS+ Treg expansion in melanoma patients," J Clin Investi. 124(1):99-110 (2014).
Simpson et al., "Regulation of CD4 T cell activation and effector function by inducible costimulator (ICOS)," Curr Opin Immunol. 22(3):326-32 (2010).
Smigiel et al., "CCR7 provides localized access to IL-2 and defines homeostatically distinct regulatory T cell subsets," J Exp Med. 211 (1):121-36 (2014).
Spitzer et al., Systemic Immunity Is Required for Effective Cancer Immunotherapy, Cell. 168(3):487-502.e15 (2017) (32 pages).
Tajima et al., "Critical role of activation-inducible lymphocyte immunomediatory molecule/inducible costimulator in the effector function of human T cells: a comparative in vitro study of effects of its blockade and CD28 blockade in human beings and monkeys," Hum Immunol. 69(7):399-408 (2008).
Tajima et al., "JTA-009, a fully human antibody against human AILIM/ICOS, ameliorates graft-vs-host reaction in SCID mice grafted with human PBMCs," Exp Hematol. 36(11):1514-23 (2008).
Tang et al., "Increased frequency of ICOS+ CD4 T cells as a pharmacodynamic biomarker for anti-CTLA-4 therapy," Cancer Immunol Res. 1(4):229-34 (2013).
Wang et al., "Biomarkers on melanoma patient T cells associated with ipilimumab treatment," J Transl Med. 10:146 (2012) (25 pages).
Wang et al., "Ligand binding sites of inducible costimulator and high avidity mutants with improved function," J Exp Med. 195(8):1033-41 (2002).
Watanabe et al., "A distinct role for ICOS-mediated co-stimulatory signaling in CD4+ and CD8+ T cell subsets," Int Immunol. 17(3):269-78 (2005).
Watanabe et al., "Grb2 and Gads exhibit different interactions with CD28 and play distinct roles in CD28-mediated costimulation," J Immunol. 177(2):1085-91 (2006).
Xu et al., "Follicular T-helper cell recruitment governed by bystander B cells and ICOS-driven motility," Nature. 496(7446):523-7 (2013) (7 pages).
Yagi et al., "Regulatory roles of IL-2 and IL-4 in H4/inducible costimulator expression on activated CD4+ T cells during Th cell development," J Immunol. 171(2):783-94 (2003).
Yao et al., "B7-H2 is a costimulatory ligand for CD28 in human," Immunity. 34(5):729-40 (2011) (23 pages).
Yao et al., "Supplemental Information: B7-H2 Is a Costimulatory Ligand for CD28 in Human," Immunity. 34(5):1-11 (2011).
Yost et al., "Clonal replacement of tumor-specific T cells following PD-1 blockade," Nat Med. 25(8):1251-1259 (2019).
Zheng et al., "ICOS regulates the generation and function of human CD4+ Treg in a CTLA-4 dependent manner," PLoS One. 8(12):e82203 (2013) (11 pages).
Zuberek et al., "Comparable in vivo efficacy of CD28/B7, ICOS/GL50, and ICOS/GL50B costimulatory pathways in murine tumor models: IFNgamma-dependent enhancement of CTL priming, effector functions, and tumor specific memory CTL," Cell Immunol. 225(1):53-63 (2003).
International Preliminary Report on Patentability dated Nov. 17, 2020, for PCT International Application No. PCT/US2019/032184, Harvey et al., "Methods of Treating Cancer," filed May 14, 2019 (9 pages).
Faget et al., "ICOS is associated with poor prognosis in breast cancer as it promotes the amplification of immunosuppressive CD4+ T cells by plasmacytoid dendritic cells," Oncoimmunology. 2(3):e23185 (2013) (4 pages).

(56) References Cited

OTHER PUBLICATIONS

International Search Report and Written Opinion dated Aug. 13, 2019, for PCT International Application No. PCT/US2019/032184 Harvey et al., "Methods of Treating Cancer," filed May 14, 2019 (17 pages).

Majchrzak et al., "Exploiting IL-17-producing CD4+ and CD8+ T cells to improve cancer immunotherapy in the clinic," Cancer Immunol Immunother. 65(3):247-259 (2016).

Michaelson et al., "Abstract SY03-02: Preclinical assessment of JTX-2011, an agonist antibody targeting ICOS, supports evaluation in ICONIC clinical trial," AACR 77(Suppl 13). AACR Annual Meeting 2017, April 1-5, Washington, DC, Cancer Res 2017; 77(13 Suppl); available at <http://cancerres.aacrjournals.org/content/77/13_Supplement/SY03-02.short>, retrieved on Jul. 29, 2019 (2017) (4 pages).

\* cited by examiner

Gates drawn to bisect the two populations.

Histograms of the ICOS lo and ICOS hi quadrants are overlaid with geometric mean fluorescent intensity calculated.

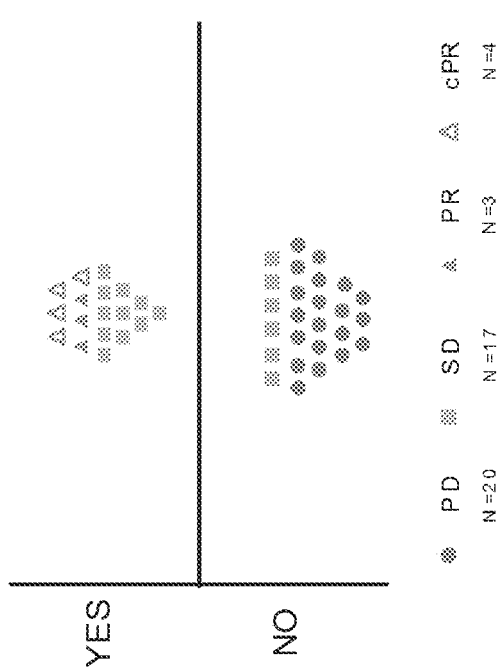

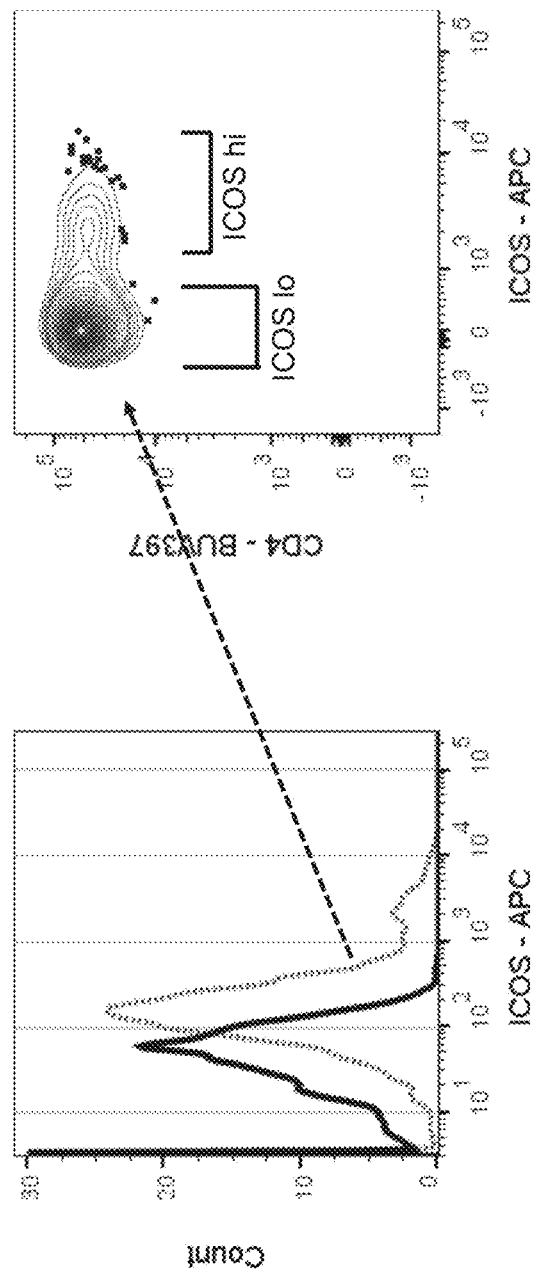

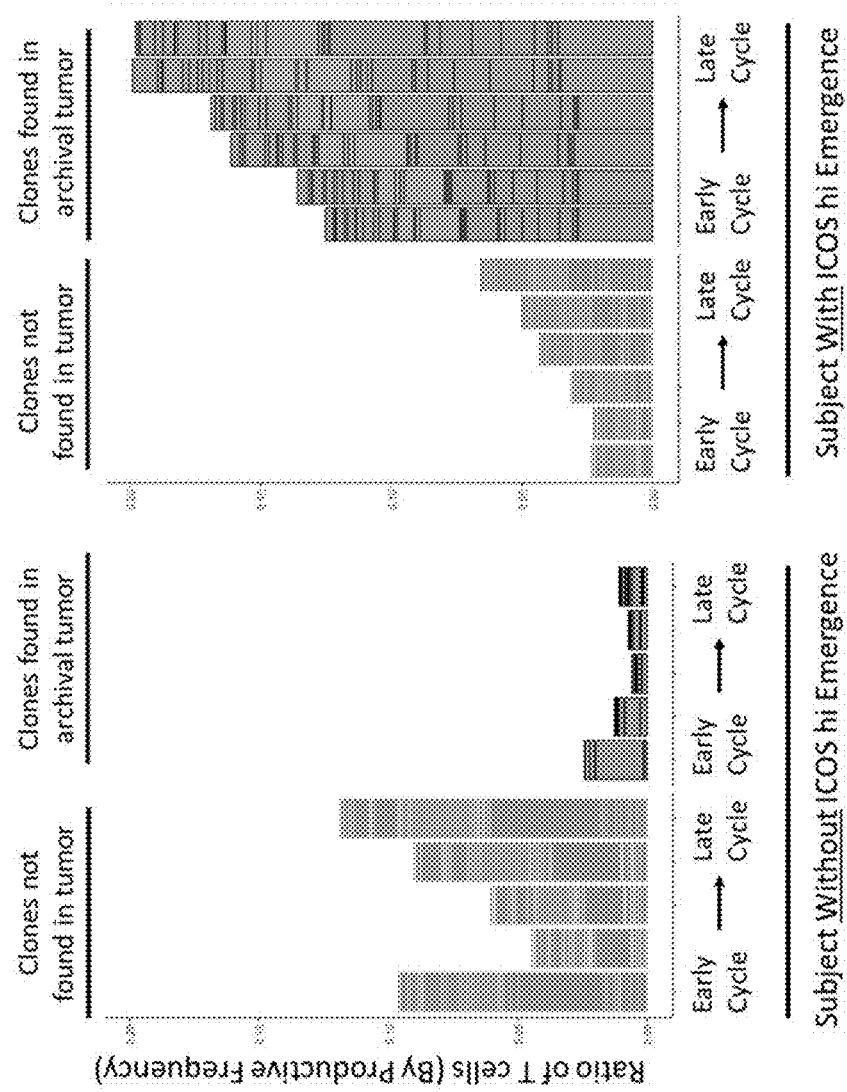

SEQUENCE LISTING

<160> NUMBER OF SEQ ID NOS: 44

<210> SEQ ID NO 1
<211> LENGTH: 446
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg

```
                  405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 2
<211> LENGTH: 218
<212> TYPE: PRT
<213> ORGANISM: Artificial Sequence
<220> FEATURE:
<223> OTHER INFORMATION: Synthetic Construct

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg His Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 117
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45
```

```
Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Trp Gly Arg Phe Gly Phe Asp Ser Trp Gly Gln Gly Thr Leu
            100                 105                 110

Val Thr Val Ser Ser
            115

<210> SEQ ID NO 4
<211> LENGTH: 111
<212> TYPE: PRT
<213> ORGANISM: Artificial Sequence
<220> FEATURE:
<223> OTHER INFORMATION: Synthetic Construct

<400> SEQUENCE: 4

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ser Gly
                 20                  25                  30

Ser Phe Asn Tyr Leu Thr Trp Tyr Gln Gln Lys Pro Gly Gln Pro Pro
             35                  40                  45

Lys Leu Leu Ile Phe Tyr Ala Ser Thr Arg His Thr Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys His His Tyr
                 85                  90                  95

Asn Ala Pro Pro Thr Phe Gly Pro Gly Thr Lys Val Asp Ile Lys
            100                 105                 110

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Phe Thr Phe Ser Asp Tyr Trp Met Asp
 1               5                  10

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct

<400> SEQUENCE: 6

Asn Ile Asp Glu Asp Gly Ser Ile Thr Glu Tyr Ser Pro Phe Val Lys
 1               5                  10                  15

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 7

Trp Gly Arg Phe Gly Phe Asp Ser
1               5

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Lys Ser Ser Gln Ser Leu Leu Ser Gly Ser Phe Asn Tyr Leu Thr
1               5                  10                  15

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Tyr Ala Ser Thr Arg His Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

His His His Tyr Asn Ala Pro Pro Thr
1               5

<210> SEQ ID NO 11
<211> LENGTH: 199
<212> TYPE: PRT
<213> ORGANISM: Homo sapiens

<400> SEQUENCE: 11

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140
```

```
Ile Gly Cys Ala Ala Phe Val Val Cys Ile Leu Gly Cys Ile Leu
145                 150                 155                 160

Ile Cys Trp Leu Thr Lys Lys Tyr Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195
```

<210> SEQ ID NO 12
<211> LENGTH: 179
<212> TYPE: PRT
<213> ORGANISM: Homo sapiens

<400> SEQUENCE: 12

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Ala Phe Val Val Val Cys Ile Leu Gly Cys Ile Leu Ile Cys Trp Leu
    130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu
```

<210> SEQ ID NO 13
<211> LENGTH: 200
<212> TYPE: PRT
<213> ORGANISM: Mus musculus

<400> SEQUENCE: 13

```
Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80
```

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Phe Gln Glu Arg Asn Leu Ser Gly Gly Tyr
            115                 120                 125

Leu His Ile Tyr Glu Ser Gln Leu Cys Cys Gln Leu Lys Leu Trp Leu
            130                 135                 140

Pro Val Gly Cys Ala Ala Phe Val Val Leu Leu Phe Gly Cys Ile
145                 150                 155                 160

Leu Ile Ile Trp Phe Ser Lys Lys Tyr Gly Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Val Thr Ser
            195                 200

<210> SEQ ID NO 14
<211> LENGTH: 180
<212> TYPE: PRT
<213> ORGANISM: Mus musculus

<400> SEQUENCE: 14

Glu Ile Asn Gly Ser Ala Asp His Arg Met Phe Ser Phe His Asn Gly
1               5                   10                  15

Gly Val Gln Ile Ser Cys Lys Tyr Pro Glu Thr Val Gln Gln Leu Lys
            20                  25                  30

Met Arg Leu Phe Arg Glu Arg Glu Val Leu Cys Glu Leu Thr Lys Thr
        35                  40                  45

Lys Gly Ser Gly Asn Ala Val Ser Ile Lys Asn Pro Met Leu Cys Leu
    50                  55                  60

Tyr His Leu Ser Asn Asn Ser Val Ser Phe Phe Leu Asn Asn Pro Asp
65                  70                  75                  80

Ser Ser Gln Gly Ser Tyr Tyr Phe Cys Ser Leu Ser Ile Phe Asp Pro
                85                  90                  95

Pro Pro Phe Gln Glu Arg Asn Leu Ser Gly Gly Tyr Leu His Ile Tyr
            100                 105                 110

Glu Ser Gln Leu Cys Cys Gln Leu Lys Leu Trp Leu Pro Val Gly Cys
        115                 120                 125

Ala Ala Phe Val Val Leu Leu Phe Gly Cys Ile Leu Ile Ile Trp
    130                 135                 140

Phe Ser Lys Lys Tyr Gly Ser Ser Val His Asp Pro Asn Ser Glu
145                 150                 155                 160

Tyr Met Phe Met Ala Ala Val Asn Thr Asn Lys Lys Ser Arg Leu Ala
                165                 170                 175

Gly Val Thr Ser
            180

<210> SEQ ID NO 15
<211> LENGTH: 200
<212> TYPE: PRT
<213> ORGANISM: Rattus norvegicus

<400> SEQUENCE: 15

Met Lys Pro Tyr Phe Ser Cys Val Phe Val Cys Phe Leu Ile Lys
1               5                   10                  15

```
Leu Leu Thr Gly Glu Leu Asn Asp Leu Ala Asn His Arg Met Phe Ser
         20                  25                  30

Phe His Asp Gly Gly Val Gln Ile Ser Cys Asn Tyr Pro Glu Thr Val
         35                  40                  45

Gln Gln Leu Lys Met Gln Leu Phe Lys Asp Arg Glu Val Leu Cys Asp
     50                  55                  60

Leu Thr Lys Thr Lys Gly Ser Gly Asn Thr Val Ser Ile Lys Asn Pro
 65                  70                  75                  80

Met Ser Cys Pro Tyr Gln Leu Ser Asn Asn Ser Val Ser Phe Phe Leu
                 85                  90                  95

Asp Asn Ala Asp Ser Ser Gln Gly Ser Tyr Phe Leu Cys Ser Leu Ser
             100                 105                 110

Ile Phe Asp Pro Pro Phe Gln Glu Lys Asn Leu Ser Gly Gly Tyr
             115                 120                 125

Leu Leu Ile Tyr Glu Ser Gln Leu Cys Cys Gln Leu Lys Leu Trp Leu
 130                 135                 140

Pro Val Gly Cys Ala Ala Phe Val Ala Ala Leu Leu Phe Gly Cys Ile
 145                 150                 155                 160

Phe Ile Val Trp Phe Ala Lys Lys Lys Tyr Arg Ser Ser Val His Asp
                 165                 170                 175

Pro Asn Ser Glu Tyr Met Phe Met Ala Ala Val Asn Thr Asn Lys Lys
             180                 185                 190

Ser Arg Leu Ala Gly Met Thr Ser
             195                 200

<210> SEQ ID NO 16
<211> LENGTH: 180
<212> TYPE: PRT
<213> ORGANISM: Rattus norvegicus

<400> SEQUENCE: 16

Glu Leu Asn Asp Leu Ala Asn His Arg Met Phe Ser Phe His Asp Gly
 1               5                   10                  15

Gly Val Gln Ile Ser Cys Asn Tyr Pro Glu Thr Val Gln Gln Leu Lys
             20                  25                  30

Met Gln Leu Phe Lys Asp Arg Glu Val Leu Cys Asp Leu Thr Lys Thr
         35                  40                  45

Lys Gly Ser Gly Asn Thr Val Ser Ile Lys Asn Pro Met Ser Cys Pro
     50                  55                  60

Tyr Gln Leu Ser Asn Asn Ser Val Ser Phe Phe Leu Asp Asn Ala Asp
 65                  70                  75                  80

Ser Ser Gln Gly Ser Tyr Phe Leu Cys Ser Leu Ser Ile Phe Asp Pro
                 85                  90                  95

Pro Pro Phe Gln Glu Lys Asn Leu Ser Gly Gly Tyr Leu Leu Ile Tyr
             100                 105                 110

Glu Ser Gln Leu Cys Cys Gln Leu Lys Leu Trp Leu Pro Val Gly Cys
         115                 120                 125

Ala Ala Phe Val Ala Ala Leu Leu Phe Gly Cys Ile Phe Ile Val Trp
     130                 135                 140

Phe Ala Lys Lys Lys Tyr Arg Ser Ser Val His Asp Pro Asn Ser Glu
 145                 150                 155                 160

Tyr Met Phe Met Ala Ala Val Asn Thr Asn Lys Lys Ser Arg Leu Ala
                 165                 170                 175

Gly Met Thr Ser
             180
```

<210> SEQ ID NO 17
<211> LENGTH: 199
<212> TYPE: PRT
<213> ORGANISM: Macaca fascicularis

<400> SEQUENCE: 17

Met Lys Ser Gly Leu Trp Tyr Phe Phe Leu Phe Cys Leu His Met Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Lys Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp Arg Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Thr Phe Val Val Cys Ile Phe Gly Cys Ile Leu
145                 150                 155                 160

Ile Cys Trp Leu Thr Lys Lys Lys Tyr Ser Ser Thr Val His Asp Pro
                165                 170                 175

Asn Gly Glu Tyr Met Phe Met Arg Ala Val Asn Thr Ala Lys Lys Ser
            180                 185                 190

Arg Leu Thr Gly Thr Thr Pro
        195

<210> SEQ ID NO 18
<211> LENGTH: 179
<212> TYPE: PRT
<213> ORGANISM: Macaca fascicularis

<400> SEQUENCE: 18

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Lys Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

Arg Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

```
Thr Phe Val Val Val Cys Ile Phe Gly Cys Ile Leu Ile Cys Trp Leu
        130                 135                 140

Thr Lys Lys Lys Tyr Ser Ser Thr Val His Asp Pro Asn Gly Glu Tyr
145                 150                 155                 160

Met Phe Met Arg Ala Val Asn Thr Ala Lys Lys Ser Arg Leu Thr Gly
                165                 170                 175

Thr Thr Pro

<210> SEQ ID NO 19
<211> LENGTH: 118
<212> TYPE: PRT
<213> ORGANISM: Artificial Sequence
<220> FEATURE:
<223> OTHER INFORMATION: Synthetic Construct

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ser Tyr
                20                  25                  30

Tyr Met His Trp Val Arg Gln Ala Pro Gly Gln Gly Leu Glu Trp Met
            35                  40                  45

Gly Ile Ile Asn Pro Glu Gly Gly Ser Thr Ala Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Tyr Tyr Asp Tyr Thr Tyr Trp Gly Gln Gly Thr
                100                 105                 110

Leu Val Thr Val Ser Ser
        115

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Tyr Thr Phe Pro Ser Tyr Tyr Met His
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Ile Ile Asn Pro Glu Gly Gly Ser Thr Ala Tyr Ala Gln Lys Phe Gln
1               5                   10                  15

Gly

<210> SEQ ID NO 22
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 22

Ala Arg Gly Gly Thr Tyr Tyr Asp Tyr Thr Tyr
1               5                   10

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Arg Ala Ser Gln Ser Ile Ser Ser Trp Leu Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Glu Ala Ser Ser Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Tyr Asn Ser Phe Pro Pro Thr
1               5
```

```
<210> SEQ ID NO 27
<211> LENGTH: 120
<212> TYPE: PRT
<213> ORGANISM: Mus musculus

<400> SEQUENCE: 27

Glu Val Gln Leu Gln Gln Ser Gly Ala Glu Leu Val Arg Pro Gly Ala
1               5                   10                  15

Val Val Lys Leu Ser Cys Lys Ala Ser Gly Phe Asp Ile Lys Asp Tyr
            20                  25                  30

Tyr Met His Trp Val Gln Gln Arg Pro Glu Gln Gly Leu Glu Trp Ile
        35                  40                  45

Gly Trp Ile Asp Pro Glu Asn Gly Asn Ala Val Tyr Asp Pro Gln Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Asp Tyr Tyr Gly Ser Lys Gly Tyr Leu Asp Val Trp Gly Ala
            100                 105                 110

Gly Thr Thr Val Thr Val Ser Ser
        115                 120

<210> SEQ ID NO 28
<211> LENGTH: 5
<212> TYPE: PRT
<213> ORGANISM: Mus musculus

<400> SEQUENCE: 28

Asp Tyr Tyr Met His
1               5

<210> SEQ ID NO 29
<211> LENGTH: 17
<212> TYPE: PRT
<213> ORGANISM: Mus musculus

<400> SEQUENCE: 29

Trp Ile Asp Pro Glu Asn Gly Asn Ala Val Tyr Asp Pro Gln Phe Gln
1               5                   10                  15

Gly

<210> SEQ ID NO 30
<211> LENGTH: 11
<212> TYPE: PRT
<213> ORGANISM: Mus musculus

<400> SEQUENCE: 30

Asp Tyr Tyr Gly Ser Lys Gly Tyr Leu Asp Val
1               5                   10

<210> SEQ ID NO 31
<211> LENGTH: 106
<212> TYPE: PRT
<213> ORGANISM: Mus musculus

<400> SEQUENCE: 31

Gln Ile Val Leu Thr Gln Ser Pro Thr Ile Met Ser Ala Ser Pro Gly
1               5                   10                  15

Glu Lys Val Thr Ile Thr Cys Ser Ala Ser Ser Ser Val Ser Tyr Met
            20                  25                  30
```

```
His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Gly Gly Ser
 50                  55                  60

Arg Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Phe Thr
                 85                  90                  95

Phe Gly Ser Gly Thr Lys Leu Glu Ile Lys
             100                 105

<210> SEQ ID NO 32
<211> LENGTH: 10
<212> TYPE: PRT
<213> ORGANISM: Mus musculus

<400> SEQUENCE: 32

Ser Ala Ser Ser Ser Val Ser Tyr Met His
1               5                   10

<210> SEQ ID NO 33
<211> LENGTH: 7
<212> TYPE: PRT
<213> ORGANISM: Mus musculus

<400> SEQUENCE: 33

Ser Thr Ser Asn Leu Ala Ser
1               5

<210> SEQ ID NO 34
<211> LENGTH: 9
<212> TYPE: PRT
<213> ORGANISM: Mus musculus

<400> SEQUENCE: 34

Gln Gln Arg Ser Ser Tyr Pro Phe Thr
1               5

<210> SEQ ID NO 35
<211> LENGTH: 115
<212> TYPE: PRT
<213> ORGANISM: Mus musculus

<400> SEQUENCE: 35

Glu Val Gln Leu Gln Gln Ser Gly Ala Glu Leu Val Arg Ser Gly Ala
1               5                   10                  15

Ser Val Lys Leu Ser Cys Thr Thr Ser Ala Phe Asn Ile Ile Asp Tyr
             20                  25                  30

Tyr Met His Trp Val Ile Gln Arg Pro Glu Gln Gly Leu Glu Trp Ile
         35                  40                  45

Ala Trp Ile Asp Pro Glu Asn Gly Asp Pro Glu Tyr Ala Pro Lys Phe
     50                  55                  60

Gln Asp Lys Ala Thr Met Thr Thr Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Thr Ala Trp Arg Gly Phe Ala Tyr Trp Gly Gln Gly Thr Leu Val Thr
             100                 105                 110

Val Ser Ala
```

-continued

```
               115

<210> SEQ ID NO 36
<211> LENGTH: 5
<212> TYPE: PRT
<213> ORGANISM: Mus musculus

<400> SEQUENCE: 36

Asp Tyr Tyr Met His
1               5

<210> SEQ ID NO 37
<211> LENGTH: 17
<212> TYPE: PRT
<213> ORGANISM: Mus musculus

<400> SEQUENCE: 37

Trp Ile Asp Pro Glu Asn Gly Asp Pro Glu Tyr Ala Pro Lys Phe Gln
1               5                   10                  15

Asp

<210> SEQ ID NO 38
<211> LENGTH: 6
<212> TYPE: PRT
<213> ORGANISM: Mus musculus

<400> SEQUENCE: 38

Trp Arg Gly Phe Ala Tyr
1               5

<210> SEQ ID NO 39
<211> LENGTH: 112
<212> TYPE: PRT
<213> ORGANISM: Mus musculus

<400> SEQUENCE: 39

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Ile His Val Pro Pro Thr Phe Gly Gly Gly Thr Lys Leu Glu Ile Lys
            100                 105                 110

<210> SEQ ID NO 40
<211> LENGTH: 16
<212> TYPE: PRT
<213> ORGANISM: Mus musculus

<400> SEQUENCE: 40

Arg Ser Ser Gln Ser Leu Val His Ser Asn Gly Asn Thr Tyr Leu His
1               5                   10                  15

<210> SEQ ID NO 41
```

```
<211> LENGTH: 7
<212> TYPE: PRT
<213> ORGANISM: Mus musculus

<400> SEQUENCE: 41

Lys Val Ser Asn Arg Phe Ser
1               5

<210> SEQ ID NO 42
<211> LENGTH: 9
<212> TYPE: PRT
<213> ORGANISM: Mus musculus

<400> SEQUENCE: 42

Ser Gln Ser Ile His Val Pro Pro Thr
1               5

<210> SEQ ID NO 43
<211> LENGTH: 535
<212> TYPE: PRT
<213> ORGANISM: Homo sapiens

<400> SEQUENCE: 43

Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
    50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190

Asp Gln His His Trp Arg Tyr Gln Ser Gly Lys Trp Val Gln Cys Gly
        195                 200                 205

Lys Ala Glu Gly Ser Met Pro Gly Asn Arg Leu Tyr Val His Pro Asp
    210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255

Met Ile Val Leu Gln Ser Leu His Lys Tyr Gln Pro Arg Leu His Ile
            260                 265                 270
```

```
Val Glu Val Asn Asp Gly Glu Pro Glu Ala Ala Cys Asn Ala Ser Asn
            275                 280                 285

Thr His Ile Phe Thr Phe Gln Glu Thr Gln Phe Ile Ala Val Thr Ala
        290                 295                 300

Tyr Gln Asn Ala Glu Ile Thr Gln Leu Lys Ile Asp Asn Asn Pro Phe
305                 310                 315                 320

Ala Lys Gly Phe Arg Glu Asn Phe Glu Ser Met Tyr Thr Ser Val Asp
                325                 330                 335

Thr Ser Ile Pro Ser Pro Pro Gly Pro Asn Cys Gln Phe Leu Gly Gly
            340                 345                 350

Asp His Tyr Ser Pro Leu Leu Pro Asn Gln Tyr Pro Val Pro Ser Arg
        355                 360                 365

Phe Tyr Pro Asp Leu Pro Gly Gln Ala Lys Asp Val Val Pro Gln Ala
        370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
                405                 410                 415

Met Ser Tyr Tyr Arg Gly Gln Glu Val Leu Ala Pro Gly Ala Gly Trp
            420                 425                 430

Pro Val Ala Pro Gln Tyr Pro Pro Lys Met Gly Pro Ala Ser Trp Phe
        435                 440                 445

Arg Pro Met Arg Thr Leu Pro Met Glu Pro Gly Pro Gly Gly Ser Glu
        450                 455                 460

Gly Arg Gly Pro Glu Asp Gln Gly Pro Pro Leu Val Trp Thr Glu Ile
465                 470                 475                 480

Ala Pro Ile Arg Pro Glu Ser Ser Asp Ser Gly Leu Gly Glu Gly Asp
                485                 490                 495

Ser Lys Arg Arg Arg Val Ser Pro Tyr Pro Ser Ser Gly Asp Ser Ser
            500                 505                 510

Ser Pro Ala Gly Ala Pro Ser Pro Phe Asp Lys Glu Ala Glu Gly Gln
        515                 520                 525

Phe Tyr Asn Tyr Phe Pro Asn
        530                 535

<210> SEQ ID NO 44
<211> LENGTH: 530
<212> TYPE: PRT
<213> ORGANISM: Mus musculus

<400> SEQUENCE: 44

Met Gly Ile Val Glu Pro Gly Cys Gly Asp Met Leu Thr Gly Thr Glu
1               5                   10                  15

Pro Met Pro Ser Asp Glu Gly Arg Gly Pro Gly Ala Asp Gln Gln His
            20                  25                  30

Arg Phe Phe Tyr Pro Glu Pro Gly Ala Gln Asp Pro Thr Asp Arg Arg
        35                  40                  45

Ala Gly Ser Ser Leu Gly Thr Pro Tyr Ser Gly Gly Ala Leu Val Pro
    50                  55                  60

Ala Ala Pro Gly Arg Phe Leu Gly Ser Phe Ala Tyr Pro Pro Arg Ala
65                  70                  75                  80

Gln Val Ala Gly Phe Pro Gly Pro Gly Glu Phe Phe Pro Pro Pro Ala
                85                  90                  95

Gly Ala Glu Gly Tyr Pro Pro Val Asp Gly Tyr Pro Ala Pro Asp Pro
            100                 105                 110
```

Arg Ala Gly Leu Tyr Pro Gly Pro Arg Glu Asp Tyr Ala Leu Pro Ala
              115                 120                 125

Gly Leu Glu Val Ser Gly Lys Leu Arg Val Ala Leu Ser Asn His Leu
        130                 135                 140

Leu Trp Ser Lys Phe Asn Gln His Gln Thr Glu Met Ile Ile Thr Lys
145                 150                 155                 160

Gln Gly Arg Arg Met Phe Pro Phe Leu Ser Phe Thr Val Ala Gly Leu
                    165                 170                 175

Glu Pro Thr Ser His Tyr Arg Met Phe Val Asp Val Val Leu Val Asp
                180                 185                 190

Gln His His Trp Arg Tyr Gln Ser Gly Lys Trp Val Gln Cys Gly Lys
            195                 200                 205

Ala Glu Gly Ser Met Pro Gly Asn Arg Leu Tyr Val His Pro Asp Ser
    210                 215                 220

Pro Asn Thr Gly Ala His Trp Met Arg Gln Glu Val Ser Phe Gly Lys
225                 230                 235                 240

Leu Lys Leu Thr Asn Asn Lys Gly Ala Ser Asn Asn Val Thr Gln Met
                245                 250                 255

Ile Val Leu Gln Ser Leu His Lys Tyr Gln Pro Arg Leu His Ile Val
                260                 265                 270

Glu Val Asn Asp Gly Glu Pro Glu Ala Ala Cys Ser Ala Ser Asn Thr
            275                 280                 285

His Val Phe Thr Phe Gln Glu Thr Gln Phe Ile Ala Val Thr Ala Tyr
    290                 295                 300

Gln Asn Ala Glu Ile Thr Gln Leu Lys Ile Asp Asn Asn Pro Phe Ala
305                 310                 315                 320

Lys Gly Phe Arg Glu Asn Phe Glu Ser Met Tyr Ala Ser Val Asp Thr
                325                 330                 335

Ser Val Pro Ser Pro Pro Gly Pro Asn Cys Gln Leu Leu Gly Gly Asp
            340                 345                 350

Pro Phe Ser Pro Leu Leu Ser Asn Gln Tyr Pro Val Pro Ser Arg Phe
    355                 360                 365

Tyr Pro Asp Leu Pro Gly Gln Pro Lys Asp Met Ile Ser Gln Pro Tyr
370                 375                 380

Trp Leu Gly Thr Pro Arg Glu His Ser Tyr Glu Ala Glu Phe Arg Ala
385                 390                 395                 400

Val Ser Met Lys Pro Thr Leu Leu Pro Ser Ala Pro Gly Pro Thr Val
                405                 410                 415

Pro Tyr Tyr Arg Gly Gln Asp Val Leu Ala Pro Gly Ala Gly Trp Pro
                420                 425                 430

Val Ala Pro Gln Tyr Pro Pro Lys Met Ser Pro Ala Gly Trp Phe Arg
            435                 440                 445

Pro Met Arg Thr Leu Pro Met Asp Pro Gly Leu Gly Ser Ser Glu Glu
    450                 455                 460

Gln Gly Ser Ser Pro Ser Leu Trp Pro Glu Val Thr Ser Leu Gln Pro
465                 470                 475                 480

Glu Pro Ser Asp Ser Gly Leu Gly Glu Gly Asp Thr Lys Arg Arg Arg
                485                 490                 495

Ile Ser Pro Tyr Pro Ser Ser Gly Asp Ser Ser Pro Ala Gly Ala
            500                 505                 510

-continued

```
Pro Ser Pro Phe Asp Lys Glu Thr Glu Gly Gln Phe Tyr Asn Tyr Phe
        515                 520                 525

Pro Asn
    530
```

METHODS OF TREATING CANCER IN A SUBJECT HAVING ELEVATED ICOS AND/OR T-BET LEVELS OF CD+4 CELLS BY ADMINISTERING AN ICOS AGONIST

SEQUENCE LISTING

The instant application contains a Sequence Listing which has been submitted electronically in ASCII format and is hereby incorporated by reference in its entirety. Said ASCII copy, created on May 13, 2019, is named 51266-006005_Sequence_Listing_5.13.19_ST25ST25 and is 41,815 bytes in size.

FIELD OF THE INVENTION

The invention relates to methods of treating cancer and methods for selecting treatment approaches for cancer.

BACKGROUND

ICOS (Inducible T-cell COStimulator; CD278) is a member of the B7/CD28/CTLA-4 immunoglobulin superfamily and is specifically expressed on T cells. Unlike CD28, which is constitutively expressed on T cells and provides co-stimulatory signals necessary for full activation of resting T cells, ICOS is expressed only after initial T cell activation.

ICOS has been implicated in diverse aspects of T cell responses (reviewed in Simpson et al., Curr. Opin. Immunol. 22: 326-332, 2010). It plays a role in the formation of germinal centers, T/B cell collaboration, and immunoglobulin class switching. ICOS-deficient mice show impaired germinal center formation and have decreased production of interleukin IL-10. These defects have been specifically linked to deficiencies in T follicular helper cells. ICOS also plays a role in the development and function of other T cell subsets, including Th1, Th2, and Th17. Notably, ICOS co-stimulates T cell proliferation and cytokine secretion associated with both Th1 and Th2 cells. Accordingly, ICOS knock-out mice demonstrate impaired development of auto-immune phenotypes in a variety of disease models, including diabetes (Th1), airway inflammation (Th2), and EAE neuro-inflammatory models (Th17).

In addition to its role in modulating T effector (Teff) cell function, ICOS also modulates T regulatory cells (Tregs). ICOS is expressed at high levels on Tregs, and has been implicated in Treg homeostasis and function.

Upon activation, ICOS, a disulfide-linked homodimer, induces a signal through the PI3K and AKT pathways. Subsequent signaling events result in expression of lineage specific transcription factors (e.g., T-bet, GATA-3) and, in turn, effects on T cell proliferation and survival.

ICOS ligand (ICOSL; B7-H2; B7RP1; CD275; GL50), also a member of the B7 superfamily, is the only ligand for ICOS and is expressed on the cell surfaces of B cells, macrophages, and dendritic cells. ICOSL functions as a non-covalently linked homodimer on the cell surface in its interaction with ICOS. Human ICOSL, although not mouse ICOSL, has been reported to bind to human CD28 and CTLA-4 (Yao et al., Immunity 34: 729-740, 2011).

T-bet (T box expressed in T cells) is a member of the T box family of transcription factors and is a lineage-defining transcription factor expressed selectively in thymocytes and Th1 cells. It initiates Th1 lineage development from naïve Th precursor cells both by activating Th1 genetic programs and by repressing the opposing Th2 and Th17 genetic programs. T-bet activates transcription of a set of genes important for Th1 cell function, including those encoding interferon gamma (IFN-γ) and the chemokine receptor CXCR3, and can also redirect polarized Th2 cells into the Th1 pathway. T-bet also controls IFN-γ production in CD8+ T cells, as well as in cells of the innate immune system, e.g., NK cells and dendritic cells. Expression of the human T-bet correlates with IFN-γ expression in Th1 and natural killer cells, suggesting a role for this gene in initiating Th1 lineage development from naïve Th precursor cells (Szabo et al., Cell 100(6):665-69, 2000).

SUMMARY

The invention provides methods of treating cancer in a subject (e.g., a human patient) in need thereof, the methods including (i) administering one or more dosages of one or more anti-cancer therapies to the subject, (ii) after the administration, obtaining one or more peripheral blood test samples from the subject, (iii) measuring ICOS and/or T-bet levels of CD4+ T cells present in the one or more peripheral blood test samples, (iv) determining if there is a population of CD4+ T cells having elevated ICOS and/or T-bet levels in any of the one or more peripheral blood test samples when compared to a control, and (v) administering (a) one or more additional dosages of the one or more anti-cancer therapies, or (b) an anti-ICOS agonist, to the subject if any of the one or more peripheral blood test samples is determined to include a population of CD4+ T cells having elevated ICOS and/or T-bet levels.

In some embodiments, step (iii) includes measuring ICOS levels of CD4+ T cells present in the one or more peripheral blood test samples, step (iv) includes determining if there is a population of CD4+ T cells having elevated ICOS levels in any one of the one or more peripheral blood test samples when compared to a control, and step (v) includes administering (a) one or more additional dosages of the one or more anti-cancer therapies, or (b) an anti-ICOS agonist, to the subject if any of the one or more peripheral blood test samples is determined to include a population of CD4+ T cells having elevated ICOS levels.

In some embodiments, step (iii) includes measuring T-bet levels of CD4+ T cells present in the one or more peripheral blood test samples, step (iv) includes determining if there is a population of CD4+ T cells having elevated T-bet levels in any one of the one or more peripheral blood test samples when compared to a control, and step (v) includes administering (a) one or more additional dosages of the one or more anti-cancer therapies, or (b) an anti-ICOS agonist, to the subject if any of the one or more peripheral blood test samples is determined to include a population of CD4+ T cells having elevated T-bet levels.

In some embodiments, step (iii) includes measuring ICOS and T-bet levels of CD4+ T cells present in the one or more peripheral blood test samples, step (iv) includes determining if there is a population of CD4+ T cells having elevated ICOS and T-bet levels in any one of the one or more peripheral blood test samples when compared to a control, and step (v) includes administering (a) one or more additional dosages of the one or more anti-cancer therapies, or (b) an anti-ICOS agonist, to the subject if any of the one or more peripheral blood test samples is determined to include a population of CD4+ T cells having elevated ICOS and/or T-bet levels.

The invention also includes methods for determining whether a subject (e.g., a human patient) may benefit from continued treatment with one or more anti-cancer therapies, or treatment with an anti-ICOS agonist, the methods including determining ICOS and/or T-bet levels of peripheral CD4+ T cells of a sample of blood of the subject, wherein detection of increased ICOS and/or T-bet levels relative to a control indicates that the subject may benefit from the continued treatment with the one or more anti-cancer therapies, optionally in combination with an anti-ICOS antibody agonist, or treatment with an anti-ICOS agonist, when the one or more anti-cancer therapies does not include anti-ICOS antibody agonist treatment.

In some embodiments, the method includes determining ICOS levels of peripheral CD4+ T cells of a sample of blood of the subject, wherein detection of increased ICOS levels relative to a control indicates that the subject may benefit from the continued treatment with the one or more anti-cancer therapies, optionally in combination with an anti-ICOS antibody agonist, or treatment with an anti-ICOS agonist, when the one or more anti-cancer therapies does not comprise anti-ICOS antibody agonist treatment.

In some embodiments, the method includes determining T-bet levels of peripheral CD4+ T cells of a sample of blood of the subject, wherein detection of increased T-bet levels relative to a control indicates that the subject may benefit from the continued treatment with the one or more anti-cancer therapies, optionally in combination with an anti-ICOS antibody agonist, or treatment with an anti-ICOS agonist, when the one or more anti-cancer therapies does not comprise anti-ICOS antibody agonist treatment.

In some embodiments, the method includes determining ICOS and T-bet levels of peripheral CD4+ T cells of a sample of blood of the subject, wherein detection of increased ICOS and/or T-bet levels relative to a control indicates that the subject may benefit from the continued treatment with the one or more anti-cancer therapies, optionally in combination with an anti-ICOS antibody agonist, or treatment with an anti-ICOS agonist, when the one or more anti-cancer therapies does not comprise anti-ICOS antibody agonist treatment.

In some embodiments, the one or more anti-cancer therapies includes an immunotherapy, such as, for example, an anti-CTLA-4 antagonist antibody (e.g., ipilimumab, tremelimumab, or BMS-986249), an anti-PD-1 or anti-PD-L1 antagonist antibody (e.g., avelumab, atezolizumab, CX-072, pembrolizumab, nivolumab, cemiplimab, spartalizumab, tislelizumab, JNJ-63723283, genolimzumab, AMP-514, AGEN2034, durvalumab, or JNC-1), or anti-ICOS agonist antibody (e.g., JTX-2011, BMS-986226, or GSK3359609). In some embodiments, the anti-ICOS agonist comprises an anti-ICOS agonist antibody (e.g., JTX-2011, BMS-986226, or GSK3359609).

In some embodiments, the one or more anti-cancer therapies includes one or more of the therapies listed in Table 2.

In some embodiments, the one or more anti-cancer therapies includes a chemotherapy (e.g., capecitabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, pemetrexed, vinorelbine, vincristine, erlotinib, afatinib, gefitinib, crizotinib, dabrafenib, trametinib, vemurafenib, or cobimetanib).

In some embodiments, the one or more anti-cancer therapies includes radiation therapy.

In some embodiments, step (v) includes administration of an anti-ICOS antibody agonist to the subject if any of the one or more peripheral blood test samples is determined to include a population of CD4+ T cells having elevated ICOS and/or T-bet levels.

In some embodiments, the anti-ICOS antibody agonist includes at least one CDR selected from the group consisting of: (a) an HCDR1 including the amino acid sequence of SEQ ID NO: 5; (b) an HCDR2 including the amino acid sequence of SEQ ID NO: 6; (c) an HCDR3 including the amino acid sequence of SEQ ID NO: 7; (d) an LCDR1 including the amino acid sequence of SEQ ID NO: 8; (e) an LCDR2 including the amino acid sequence of SEQ ID NO: 9; and (f) an LCDR3 including the amino acid sequence of SEQ ID NO: 10, wherein one or more of the CDRs includes 1 or 2 amino acid substitutions.

In some embodiments, the anti-ICOS antibody agonist includes (a) an HCDR1 including the amino acid sequence of SEQ ID NO: 5; (b) an HCDR2 including the amino acid sequence of SEQ ID NO: 6; (c) an HCDR3 including the amino acid sequence of SEQ ID NO: 7; (d) an LCDR1 including the amino acid sequence of SEQ ID NO: 8; (e) an LCDR2 including the amino acid sequence of SEQ ID NO: 9; and (f) an LCDR3 including the amino acid sequence of SEQ ID NO: 10.

In some embodiments, the anti-ICOS antibody agonist includes (a) a heavy chain including the amino acid sequence of SEQ ID NO: 1 and/or (b) a light chain including the amino acid sequence of SEQ ID NO: 2.

In some embodiments, the one or more anti-cancer therapies includes any combination of at least two or at least three of: (i) an anti-CTLA-4 antagonist antibody, (ii) an anti-PD-1 or anti-PD-L1 antagonist antibody, (iii) an anti-ICOS agonist antibody, (iv) a therapy of Table 2, (v) a chemotherapy, and (vi) radiation therapy.

In some embodiments, the one or more anti-cancer therapies is administered two, three, four, five, or more times prior to obtaining the one or more peripheral blood test samples.

In some embodiments, the obtaining of the one or more peripheral blood test samples is performed fewer than 4 weeks, 3 weeks, or 2 weeks, or less than 1 week, after the one or more administrations of the dosages of the one or more anti-cancer therapies.

In some embodiments, the dosage of the one or more anti-cancer therapies is administered multiple times at regular intervals, e.g., regular intervals selected from the group consisting of a dosage every week, a dosage every two weeks, a dosage every three weeks, a dosage every four weeks, a dosage every six weeks, a dosage every nine weeks, and a dosage every twelve weeks.

In some embodiments, the obtaining of the one or more peripheral blood test samples includes the obtaining of multiple peripheral blood test samples, with test samples being obtained concurrent with one or more of the administrations.

In some embodiments, the obtaining of the one or more peripheral blood test samples includes the obtaining of multiple peripheral blood test samples, with test samples being obtained during a time intervening the multiple administrations.

In some embodiments, the methods further include halting the administration of the one or more anti-cancer therapies if, after the one or more anti-cancer therapies is administered for four or more intervals, a population of CD4+ T cells having elevated ICOS and/or T-bet levels compared to a control is not detected in any one of the peripheral blood test samples.

In some embodiments, the methods further include halting the administration of the one or more anti-cancer therapies if, after of the one or more anti-cancer therapies is administered for five or more, six or more, seven or more, eight or more, nine or more, or ten or more intervals, a peripheral blood test sample is obtained based on which it is determined that there is not a population of CD4+ T cells having elevated ICOS and/or T-bet levels compared to a control.

In some embodiments, the method further includes storing a portion of one or more of the peripheral blood test samples.

In some embodiments, a portion of the CD4+ T cells having elevated ICOS and/or T-bet levels is isolated from one or more of the peripheral blood test samples and stored under conditions suitable for maintaining the viability of the CD4+ T cells.

In some embodiments, the stored CD4+ T cells are stored in a cell culture medium.

In some embodiments, the stored CD4+ T cells are stored at a concentration of greater than 100,000 cells/mL, e.g., a concentration between 100,000 cells/mL and 100 million cells/mL.

The invention also provides suspensions of CD4+ T cells obtained according to the methods described herein.

In some embodiments, the control includes a peripheral blood test sample, which is optionally obtained from the subject before one or more of the administrations of the one or more anti-cancer therapies to the subject.

In some embodiments, the control includes a peripheral blood sample obtained from a healthy individual not receiving the one or more anti-cancer therapies.

In some embodiments, determining of ICOS and/or T-bet levels includes the use of an immunoassay, which optionally includes the use of an antibody that binds to an intracellular domain of ICOS to detect ICOS.

In some embodiments, antibody includes a heavy chain variable region sequence of SEQ ID NO: 27 and a light chain variable region sequence of SEQ ID NO: 31; or the antibody includes a heavy chain variable region sequence of SEQ ID NO: 35 and a light chain variable region sequence of SEQ ID NO: 39.

In some embodiments, the antibody cross-competes with an antibody including a heavy chain variable region sequence of SEQ ID NO: 27 and a light chain variable region sequence of SEQ ID NO: 31; or cross-competes with an antibody including a heavy chain variable region sequence of SEQ ID NO: 35 and a light chain variable region sequence of SEQ ID NO: 39.

In some embodiments, the methods further include measuring ICOS and/or T-bet levels of CD8+ T cells present in the one or more peripheral blood test samples, wherein a population of CD8+ T cells having elevated ICOS and/or T-bet levels relative to a control is not detected in the samples.

In some embodiments, the cancer is selected from gastric cancer, breast cancer, which optionally is triple negative breast cancer (TNBC), non-small cell lung cancer (NSCLC), melanoma, renal cell carcinoma (RCC), bladder cancer, endometrial cancer, diffuse large B-cell lymphoma (DLBCL), Hodgkin's lymphoma, ovarian cancer, and head and neck squamous cell cancer (HNSCC).

In some embodiments, the population of CD4+ T cells having elevated ICOS and/or T-bet levels includes a new, separate population of CD4+ T cells, which was induced by the one or more anti-cancer therapies.

The invention also includes methods of generating an expanded population of CD4+ T cells having elevated ICOS expression, the method including culturing the foregoing suspension of CD4+ T cells under initial culture conditions suitable for expanding the population of CD4+ T cells. These initial conditions suitable for expanding the population of CD4+ T cells may include contacting the suspension with, e.g., a CD3 agonist (e.g., OKT3), one or more of an anti-PD-1 antibody antagonist, an anti-CTLA-4 antibody, and an ICOS agonist, and, optionally, one or more compounds (e.g., two or more, or all three) selected from the group including of IL-2, IL-12, and anti-IL-4. These methods can also include contacting the suspension with, e.g., a CD28 agonist. In certain embodiments, the CD3 agonist and anti-CD28 agonist are present in a tetrameric antibody complex. In such methods, the suspension of CD4+ T cells are incubated under the initial culture conditions, e.g., for a period between one and five days (e.g., approximately 1, 2, 3, 4, or 5 days).

In certain embodiments, the methods of the invention can further include incubating the suspension of CD4+ T cells under a second culture condition suitable for expanding the population of CD4+ T cells. Here, optionally, the cells are washed prior to the application of the second culture condition. In certain embodiments, the second culture condition can include, e.g., contacting the suspension of cells with an anti-PD-1 antibody antagonist, an anti-CTLA-4 antibody, and an ICOS agonist. In certain embodiments, the second culture condition includes contacting the suspension of cells with one or more compounds (e.g., two or more, or all three) selected from the group including of IL-2, IL-12, and anti-IL-4. Additionally, or alternatively, the second culture condition includes contacting the suspension of cells with an anti-CD28 antibody agonist. Alternatively, in certain embodiments, the second culture conditions does not include contacting the suspension of cells with a CD3 agonist and/or CD28 agonist. The second culture condition can be maintained, e.g., for between 1 and 5 days (e.g., for 1, 2, 3, 4, or 5 days).

In another embodiment, the invention features a suspension of cells generated by any one of the foregoing culturing methods.

In yet another embodiment, the invention features a method of treating cancer in a subject in need thereof, the method including administering to the patient the foregoing suspension of cells to said patient (e.g., wherein the suspension of cells are derived from a population of cells obtained from the patient prior to culturing).

Other features and advantages of the invention will be apparent from the following detailed description, the drawings, and the claims.

BRIEF DESCRIPTION OF THE DRAWINGS

FIG. 7A is a plot showing the number of cancer patients receiving JTX-2011 monotherapy or combination therapy of JTX-2011 and nivolumab who had CD4+ T cells with and without (yes and no) elevated levels of ICOS. Circles represent patients who had progressive disease, squares represent patients who had stable disease, filled triangles represent patients who had unconfirmed partial responses, and unfilled triangles represent patients who had confirmed partial responses.

FIG. 8A is a graph showing an increase in ICOS staining 48 hours post-dose relative to 1 hour post-dose in Sa1/N tumor bearing mice receiving a once weekly dose of 0.25 mg/kg JTX-10110-mG2a.

FIG. 8B is a contour plot showing ICOS expression in CD4+ T cells at 48 hours post dose from a Sa1/N tumor bearing mice receiving a once weekly dose of 0.25 mg/kg JTX-10110-mG2a.

FIGS. 19A and 19B are a pair of graphs showing the frequency of tumor associated clones and de novo clones in subjects without (FIG. 19A) and with (FIG. 19B) emergent ICOS$^{hi}$ CD4+ T cells.

DETAILED DESCRIPTION

Figure 1:
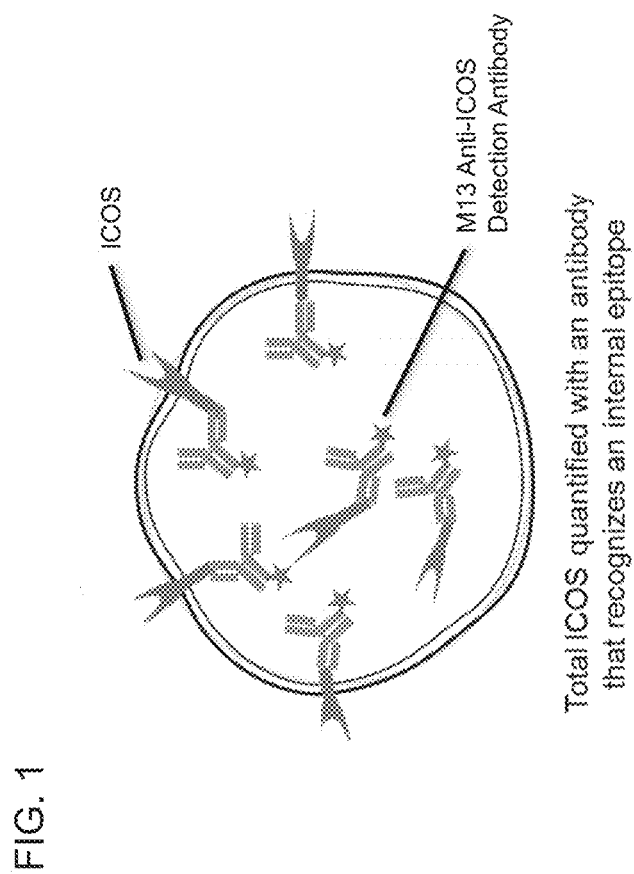
FIG. 1 is a schematic showing the M13 anti-ICOS detection antibody (see, e.g., Table 3 and WO 2017/070423; 2M13) binding to an intracellular epitope of ICOS. M13 binding to ICOS does not interfere with binding of therapeutic anti-ICOS antibody JTX-2011 to the ICOS extracellular region.

Methods of treating cancer are provided. The methods include treating subjects with one or more anti-cancer therapies and then determining whether peripheral blood samples of the subjects include CD4+ T cells with elevated ICOS and/or T-bet levels. If they do, then either (a) treatment with the one or more anti-cancer therapies is continued, optionally in combination with treatment with an anti-ICOS agonist antibody, or (b) the subject is treated with an anti-ICOS agonist (e.g., an anti-ICOS agonist antibody) in the absence of further treatment with the one or more anti-cancer therapies. Also provided are methods for determining whether a subject may benefit from continued treatment with one or more anti-cancer therapies, or treatment with an anti-ICOS agonist (e.g., an anti-ICOS agonist antibody), based on detection of elevated ICOS and/or T-bet levels in CD4+ T cells from peripheral blood samples. If a population of such cells is identified in a sample, then the subject may benefit from either (a) continued treatment with the one or more anti-cancer therapies, optionally in combination with an anti-ICOS agonist antibody, or (b) treatment with an anti-ICOS agonist (e.g., an anti-ICOS agonist antibody) in the absence of further treatment with the one or more anti-cancer therapies.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

I. Definitions

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments.

As used herein, the singular form "a," "an," and "the" includes plural references unless indicated otherwise.

Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

As is understood by one skilled in the art, reference to "about" a value or parameter herein includes (and describes) embodiments that are directed to that value or parameter per se. For example, description referring to "about X" includes description of "X."

The terms "nucleic acid molecule," "nucleic acid," and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

"ICOS" and "inducible T-cell costimulatory" as used herein refer to any native ICOS that results from expression and processing of ICOS in a cell. The term includes ICOS from any vertebrate source, including mammals such as primates (e.g., humans and cynomolgus monkeys) and rodents (e.g., mice and rats), unless otherwise indicated. The term also includes naturally occurring variants of ICOS, e.g., splice variants or allelic variants. The amino acid sequence of an exemplary human ICOS precursor protein, with signal sequence (amino acids 1-20) is shown in SEQ ID NO: 11. The amino acid sequence of an exemplary mature human ICOS is shown in SEQ ID NO: 12. The intracellular portion of ICOS is indicated in Table 3 by underlining within SEQ ID NOs: 11 and 12. The amino acid sequence of an exemplary mouse ICOS precursor protein, with signal sequence (amino acids 1-20) is shown in SEQ ID NO: 13. The amino acid sequence of an exemplary mature mouse ICOS is shown in SEQ ID NO: 14. The amino acid sequence of an exemplary rat ICOS precursor protein, with signal sequence (amino acids 1-20) is shown in SEQ ID NO: 15. The amino acid sequence of an exemplary mature rat ICOS is shown in SEQ ID NO: 16. The amino acid sequence of an exemplary cynomolgus monkey ICOS precursor protein, with signal sequence (amino acids 1-20) is shown in SEQ ID NO: 17. The amino acid sequence of an exemplary mature cynomolgus monkey ICOS is shown in SEQ ID NO: 18.

"T-bet," "T-cell-Specific T-Box Transcription Factor T-Bet," or "T-Box 21" as used herein refer to any native T-bet, encoded by the TBX21 gene, that results from expression and processing of T-bet in a cell. The term includes T-bet from any vertebrate source, including mammals such as primates (e.g., humans and cynomolgus monkeys) and rodents (e.g., mice and rats), unless otherwise indicated. The term also includes naturally occurring variants of T-bet, e.g., splice variants or allelic variants. The amino acid sequence of an exemplary human T-bet protein is shown in SEQ ID NO: 43. The amino acid sequence of an exemplary mouse T-bet is shown in SEQ ID NO: 44.

The term "specifically binds" to an antigen or epitope is a term that is well-understood in the art, and methods to determine such specific binding are also well known in the art. A molecule is said to exhibit "specific binding" or "preferential binding" if it reacts or associates more frequently, more rapidly, with greater duration, and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an ICOS epitope is an antibody that binds this epitope with greater affinity, avidity, more readily, and/or with greater duration than it binds to other ICOS epitopes or non-ICOS epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, "substantially pure" refers to material which is at least 50% pure (that is, free from contaminants), more preferably, at least 90% pure, more preferably, at least 95% pure, yet more preferably, at least 98% pure, and most preferably, at least 99% pure.

As used herein, the term "epitope" refers to a site on a target molecule (for example, an antigen, such as a protein, nucleic acid, carbohydrate, or lipid) to which an antigen-binding molecule (for example, an antibody, antibody fragment, or scaffold protein containing antibody binding regions) binds. Epitopes often include a chemically active surface grouping of molecules such as amino acids, polypeptides, or sugar side chains and have specific three-dimensional structural characteristics as well as specific charge characteristics. Epitopes can be formed both from contiguous and/or juxtaposed noncontiguous residues (for example, amino acids, nucleotides, sugars, or lipid moieties) of the target molecule. Epitopes formed from contiguous residues, also called linear epitopes (for example, amino acids, nucleotides, sugars, or lipid moieties), typically are retained on exposure to denaturing solvents whereas epitopes formed from non-contiguous residues, also called non-linear or conformational epitopes, are formed by tertiary folding, and typically are lost on treatment with denaturing solvents. An epitope may include, but is not limited to, at least 3, at least 5, or 8-10 residues (for example, amino acids or nucleotides). In some examples, an epitope is less than 20 residues (for example, amino acids or nucleotides) in length, less than 15 residues, or less than 12 residues.

Two antibodies may bind to the same epitope within an antigen, or to overlapping epitopes, if they exhibit competitive binding for the antigen. Accordingly, in some embodiments, an antibody is said to "cross-compete" with another antibody if it specifically interferes with the binding of the antibody to the same or an overlapping epitope.

The term "antibody" herein is used in the broadest sense and encompasses various antibody structures, including but not limited to, monoclonal antibodies, polyclonal antibodies, multispecific antibodies (for example, bispecific (such as Bi-specific T-cell engagers) and trispecific antibodies), and antibody fragments as long as they exhibit a desired antigen-binding activity.

The term antibody includes, but is not limited to, fragments that are capable of binding to an antigen, such as Fv, single-chain Fv (scFv), Fab, Fab', di-scFv, sdAb (single domain antibody), and (Fab')2 (including a chemically linked F(ab')2). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc. Furthermore, for all antibody constructs provided herein, variants having the sequences from other organisms are also contemplated. Thus, if a human version of an antibody is disclosed, one of skill in the art will appreciate how to transform the human sequence based antibody into a mouse, rat, cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, and/or a combination of the Kabat, Chothia, AbM, and/or contact definitions. Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The AbM definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, H26-H35B of H1, 50-58 of H2, and 95-102 of H3. The Contact definition can include, for example, CDRs (CDR-L1, CDR-L2, CDR-L3, CDR-H1, CDR-H2, and CDR-H3) at amino acid residues 30-36 of L1, 46-55 of L2, 89-96 of L3, 30-35 of H1, 47-58 of H2, and 93-101 of H3. The Chothia definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, 26-32 . . . 34 of H1, 52-56 of H2, and 95-102 of H3. With the exception of CDR1 in $V_H$, CDRs generally comprise the amino acid residues that form the hypervariable loops. The various CDRs within an antibody can be designated by their appropriate number and chain type, including, without limitation as: a) CDR-L1, CDR-L2, CDR-L3, CDR-H1, CDR-H2, and CDR-H3; b) CDRL1, CDRL2, CDRL3, CDRH1, CDRH2, and CDRH3; c) LCDR-1, LCDR-2, LCDR-3, HCDR-1, HCDR-2, and HCDR-3; or d) LCDR1, LCDR2, LCDR3, HCDR1, HCDR2, and HCDR3; etc. The term "CDR" is used herein to also encompass HVR or a "hyper variable region," including hypervariable loops. Exemplary hypervariable loops occur at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987)).

The term "heavy chain variable region" as used herein refers to a region comprising at least three heavy chain CDRs. In some embodiments, the heavy chain variable region includes the three CDRs and at least FR2 and FR3. In some embodiments, the heavy chain variable region includes at least heavy chain HCDR1, framework (FR) 2, HCDR2, FR3, and HCDR3. In some embodiments, a heavy chain variable region also comprises at least a portion of an FR1 and/or at least a portion of an FR4.

The term "heavy chain constant region" as used herein refers to a region comprising at least three heavy chain constant domains, CH1, CH2, and CH3. Of course, non-function-altering deletions and alterations within the domains are encompassed within the scope of the term "heavy chain constant region," unless designated otherwise. Non-limiting exemplary heavy chain constant regions include γ, δ, and α. Non-limiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising at least three light chain CDRs. In some embodiments, the light chain variable region includes the three CDRs and at least FR2 and FR3. In some embodiments, the light chain variable region includes at least light chain LCR1, framework (FR) 2, LCD2, FR3, and LCD3. For example, a light chain variable region may comprise light chain CDR1, framework (FR) 2, CDR2, FR3, and CDR3. In some embodiments, a light chain variable region also comprises at least a portion of an FR1 and/or at least a portion of an FR4.

The term "light chain constant region" as used herein refers to a region comprising a light chain constant domain, $C_L$. Non-limiting exemplary light chain constant regions include λ and κ. Of course, non-function-altering deletions and alterations within the domains are encompassed within the scope of the term "light chain constant region," unless designated otherwise.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework can comprise the same amino acid sequence thereof, or it can contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Affinity" refers to the strength of the sum total of noncovalent interactions between a single binding site of a molecule (for example, an antibody) and its binding partner (for example, an antigen). The affinity of a molecule X for its partner Y can generally be represented by the dissociation constant (KD). Affinity can be measured by common methods known in the art (such as, for example, ELISA KD, KinExA, bio-layer interferometry (BLI), and/or surface plasmon resonance devices (such as a BIAcore® device), including those described herein).

The term "KD," "Kd," "Kd," or "Kd value" as used herein, refers to the equilibrium dissociation constant of an antibody-antigen interaction.

The term "biological activity" refers to any one or more biological properties of a molecule (whether present naturally as found in vivo, or provided or enabled by recombinant means). Biological properties include, but are not limited to, binding a receptor, inducing cell proliferation, inhibiting cell growth, inducing other cytokines, inducing apoptosis, and enzymatic activity. In some embodiments, biological activity of an ICOS protein includes, for example, costimulation of T cell proliferation and cytokine secretion associated with Th1 and Th2 cells; modulation of Treg cells; effects on T cell differentiation including modulation of transcription factor gene expression; induction of signaling through PI3K and AKT pathways; and mediating ADCC.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, 90%, or 100%.

The phrase "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 20%, 25%, 30%, 35%, 40%, 45%, 50%, 60%, 70%, 80%, 90%, or 100% compared to the reference value.

The phrase "substantially increased," as used herein, denotes a sufficiently high degree of increase between a numeric value and a reference numeric value such that one of skill in the art would consider the difference between the two values to be of statistical significance within the context of the biological characteristic measured by said values. In some embodiments, the substantially increased numeric values is increased by greater than about any one of 10%, 20%, 25%, 30%, 35%, 40%, 45%, 50%, 60%, 70%, 80%, 90%, or 100% compared to the reference value.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated."

The terms "individual," "patient," or "subject" are used interchangeably herein to refer to an animal, for example, a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

The term "sample" or "patient sample" as used herein, refers to a composition that is obtained or derived from a subject of interest that contains a cellular and/or other molecular entity that is to be characterized and/or identified, for example, based on physical, biochemical, chemical, and/or physiological characteristics. For example, the phrase "test sample," and variations thereof, refers to any sample obtained from a subject of interest that would be expected or is known to contain a cellular and/or molecular entity that is to be characterized. By "tissue or cell sample" is meant a collection of similar cells obtained from a tissue of a subject or patient. The source of the tissue or cell sample may be blood (e.g., peripheral blood) or any blood constituents; solid tissue as from a fresh, frozen, and/or preserved organ or tissue sample or biopsy or aspirate; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like. In some embodiments, a sample includes peripheral blood obtained from a subject or patient, which includes CD4+ cells. In some embodiments, a sample includes CD4+ cells isolated from peripheral blood.

A "control," "control sample," "reference," or "reference sample" as used herein, refers to any sample, standard, or level that is used for comparison purposes. A control or reference may be obtained from a healthy and/or non-diseased sample. In some examples, a control or reference may be obtained from an untreated sample or patient. In some examples, a reference is obtained from a non-diseased or non-treated sample of a subject individual. In some examples, a reference is obtained from one or more healthy individuals who are not the subject or patient. In some embodiments, a control sample, reference sample, reference cell, or reference tissue is obtained from the patient or subject at a time point prior to one or more administrations of a treatment (e.g., one or more anti-cancer treatments), or prior to being subjected to any of the methods of the invention.

A "disease" or "disorder" as used herein refers to a condition where treatment is needed and/or desired. In some embodiments, the disease or disorder is cancer.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular non-limiting examples of such cancers include gastric cancer, breast cancer (e.g., triple negative breast cancer (TNBC)), non-small cell lung cancer (NSCLC), squamous cell cancer, small-cell lung cancer, pituitary cancer, esophageal cancer, astrocytoma, soft tissue sarcoma, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, colon cancer, colorectal cancer, endometrial or uterine carcinoma (including uterine corpus endometrial carcinoma), salivary gland carcinoma, kidney cancer, renal cancer, liver cancer, prostate cancer, vulval cancer, thyroid cancer, hepatic carcinoma, brain cancer, testis cancer, cholangiocarcinoma, gallbladder carcinoma, melanoma, and various types of head and neck cancer. These cancers, and others, can be treated or analyzed according to the methods of the invention.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example, metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering an anti-cancer therapy. "Ameliorating" also includes shortening or reduction in duration of a symptom.

In the context of cancer, the term "treating" includes any or all of: inhibiting growth of cancer cells, inhibiting replication of cancer cells, lessening of overall tumor burden, and ameliorating one or more symptoms associated with the disease.

"Preventing," as used herein, includes providing prophylaxis with respect to the occurrence or recurrence of a disease in a subject that may be predisposed to the disease but has not yet been diagnosed with the disease. Unless otherwise specified, the terms "reduce," "inhibit," or "prevent" do not denote or require complete prevention over all time.

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (for example, severity of disease, progression/non-progression/improvement, etc.). While the present disclosure may provide exemplary pre-determined levels, it is well-known that cutoff values may vary depending on the nature of the immunoassay (for example, antibodies employed, etc.). It further is well within the skill of one of ordinary skill in the art to adapt the disclosure herein for other immunoassays to obtain immunoassay-specific cutoff values for those other immunoassays based on this disclosure. Whereas the precise value of the pre-determined cutoff/level may vary between assays, correlations as described herein (if any) may be generally applicable.

In some embodiments, the terms "elevated levels of ICOS," "elevated ICOS levels," "ICOS at an elevated level," "ICOS$^{HIGH}$," and "ICOS$^{hi}$" refer to increased levels of ICOS in cells (e.g., CD4+ T cells) of a subject, e.g., in a peripheral blood sample of the subject, after treatment of the subject with one or more anti-cancer therapies. The increased levels can be determined relative to a control which may be, e.g., a peripheral blood sample from the subject being treated, but either before any treatment with the one or more anti-cancer therapies at all, or before treatment with a second or further cycle of the one or more anti-cancer therapies. Alternatively, the control can be a level from a matched sample (e.g., a peripheral blood sample) of a healthy individual. In some embodiments, the level of ICOS is determined at the level of expressed protein, which may be detected in some embodiments using an antibody directed to an intracellular portion of ICOS. In some embodiments, the detection using such an antibody is done by use of flow cytometry. In some embodiments, an increase of at least 2-fold (e.g., at least 3-fold, 4-fold, 5-fold, 7.5-fold, 10-fold, or 15-fold) in mean fluorescence intensity (MFI), relative to a control, indicates detection of elevated ICOS levels. In some embodiments, detection of an increase in ICOS levels in at least 5% (e.g., at least 10%, 20%, 30%, 40%, 50%, 60%, 70%, 80%, or 90%) of CD4+ T cells in a peripheral blood sample indicates a subject having an ICOS hi sample. In some embodiments, an increase of at least 2-fold (e.g., at least 3-fold, 4-fold, 5-fold, 7.5-fold, 10-fold, or 15-fold) in mean fluorescence intensity (MFI), relative to a control, in at least 5% (e.g., at least 10%, 20%, 30%, 40%, 50%, 60%, 70%, 80%, or 90%) of CD4+ T cells in a peripheral blood sample indicates detection of elevated ICOS levels. In some embodiments, elevated ICOS levels refer to an increase in total ICOS expression levels (e.g., mRNA levels or protein levels) in CD4+ T cells in the peripheral blood test sample of about 10%, 20%, 30%, 40%, 50%, 60%, 70%, 80%, 85%, 90%, 95%, 100%, or greater relative to a control sample. In some embodiments, elevated ICOS levels refers to an increase in total ICOS expression levels (e.g., mRNA levels or protein levels) in the CD4+ T cells in a peripheral blood sample of about at least 1.1×, 2×, 3×, 4×, 5×, 10×, 15×, 20×, 30×, 40×, 50×, 100×, 500×, 1000×, or greater relative to a control sample.

In some embodiments, the terms "elevated levels of T-bet," "elevated T-bet levels," "T-bet at an elevated level," "T-bet$^{HIGH}$," and "T-bet$^{hi}$" refer to increased levels of T-bet in cells (e.g., CD4+ T cells) of a subject, e.g., in a peripheral blood sample of the subject, after treatment of the subject with one or more anti-cancer therapies. The increased levels can be determined relative to a control which may be, e.g., a peripheral blood sample from the subject being treated, but either before any treatment with the one or more anti-cancer therapies at all, or before treatment with a second or further cycle of the one or more anti-cancer therapies. Alternatively, the control can be a level from a matched sample (e.g., a peripheral blood sample) of a healthy individual. In some embodiments, the level of T-bet is determined at the level of expressed protein, which may be detected in some embodiments using an antibody directed to T-bet. In some embodiments, the detection using such an antibody is done by use of flow cytometry. In some embodiments, an increase of at least 2-fold (e.g., at least 3-fold, 4-fold, 5-fold, 7.5-fold, 10-fold, or 15-fold) in mean fluorescence intensity (MFI), relative to a control, indicates detection of elevated T-bet levels. In some embodiments, detection of an increase in T-bet levels in at least 5% (e.g., at least 10%, 20%, 30%, 40%, 50%, 60%, 70%, 80%, or 90%) of CD4+ T cells in a peripheral blood sample indicates a subject having a T-bet hi sample. In some embodiments, an increase of at least 2-fold (e.g., at least 3-fold, 4-fold, 5-fold, 7.5-fold, 10-fold, or 15-fold) in mean fluorescence intensity (MFI), relative to a control, in at least 5% (e.g., at least 10%, 20%, 30%, 40%, 50%, 60%, 70%, 80%, or 90%) of CD4+ T cells in a peripheral blood sample indicates detection of elevated T-bet levels. In some embodiments, elevated T-bet levels refer to an increase in total T-bet expression levels (e.g., mRNA levels or protein levels) in CD4+ T cells in the peripheral blood test sample of about 10%, 20%, 30%, 40%, 50%, 60%, 70%, 80%, 85%, 90%, 95%, 100%, or greater relative to a control sample. In some embodiments, elevated T-bet levels refers to an increase in total T-bet expression levels (e.g., mRNA levels or protein levels) in the CD4+ T cells in a peripheral blood sample of about at least 1.1×, 2×, 3×, 4×, 5×, 10×, 15×, 20×, 30×, 40×, 50×, 100×, 500×, 1000×, or greater relative to a control sample.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce, or arrest an activity, function, and/or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time.

As used herein, "delaying development of a disease" means to defer, hinder, slow, retard, stabilize, suppress, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

A "therapeutically effective amount" of a substance/molecule, agonist, or antagonist may vary according to factors such as the disease state, age, sex, and weight of the individual, and the ability of the substance/molecule, agonist, or antagonist to elicit a desired response in the individual. A therapeutically effective amount is also one in which any toxic or detrimental effects of the substance/molecule, agonist, or antagonist are outweighed by the therapeutically beneficial effects. A therapeutically effective amount may be delivered in one or more administrations. A therapeutically effective amount refers to an amount effective, at dosages, and for periods of time necessary, to achieve the desired therapeutic and/or prophylactic result. The therapeutically effective amount of the treatment of the invention can be measured by various endpoints commonly used in evaluating cancer treatments, including, but not limited to: extending survival (including OS and PFS); resulting in an objective response (including a CR or a PR); tumor regression, tumor weight or size shrinkage, longer time to disease progression, increased duration of survival, longer PFS, improved OS rate, increased duration of response, and improved quality of life and/or improving signs or symptoms of cancer.

As used herein, the term "progressive disease" (PD) refers to least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. The appearance of one or more new lesions is also considered progression.

As used herein, the term "partial response" (PR) refers to at least a 30% decrease in the sum of diameters of target lesions, taking as reference the baseline sum diameters.

As used herein, the term "complete response" (CR) refers to the disappearance of all target lesions with the short axes of any target lymph nodes reduced to <10 mm.

As used herein, the term "stable disease" (SD) refers to neither sufficient shrinkage to qualify for PR nor sufficient increase to qualify for PD, taking as reference the smallest sum of diameters while on study.

As used herein, the term "best overall response" (BOR) is the best response recorded from the start of the study treatment until the earliest of objective progression or start of new anti-cancer therapy, taking into account any requirement for confirmation. The patient's best overall response assignment will depend on the findings of both target and non-target disease and will also take into consideration the appearance of new lesions. The best overall response is calculated via an algorithm using the assessment responses provided by an investigator over the course of a trial.

As used herein, the term "not evaluable" (NE) refers to when an incomplete radiologic assessment of target lesions is performed or there is a change in the method of measurement from baseline that impacts the ability to make a reliable evaluation of response.

As used herein, the term "objective response rate" (ORR) is equal to the proportion of patients achieving a best overall response of partial or complete response (PR+CR) according to RECIST 1.1.

As used herein, the term "overall survival" (OS) refers to the percentage of patients remaining alive for a defined period of time, such as 1 year, 5 years, etc. from the time of diagnosis or treatment. Overall survival is evaluated by the Kaplan-Meier method, and a 95% confidence interval (CI) is provided for the median OS in each treatment arm.

As used herein, the term "progression-free survival" (PFS) refers to the patient remaining alive without the cancer progressing or getting worse. PFS may be defined as the time from selection for treatment until the first radiographic documentation of objective progression as defined by RECIST (Version 1.1), or death from any cause.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time, or where the administration of one therapeutic agent falls within a short period of time (e.g., within one day) relative to administration of the other therapeutic agent. For example, the two or more therapeutic agents are administered with a time separation of no more than about a specified number of minutes.

The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes.

As used herein, "in conjunction with" refers to administration of one treatment modality in addition to another treatment modality. As such, "in conjunction with" refers to administration of one treatment modality before, during, or after administration of the other treatment modality to the individual.

The terms "label" and "detectable label" mean a moiety attached to a polynucleotide or polypeptide to render a reaction (for example, polynucleotide amplification or antibody binding) detectable. The polynucleotide or polypeptide comprising the label may be referred to as "detectably labeled." Thus, the term "labeled binding protein" refers to a protein with a label incorporated that provides for the identification of the binding protein. The term "labeled oligonucleotide," "labeled primer," "labeled probe," etc. refers to a polynucleotide with a label incorporated that provides for the identification of nucleic acids that comprise or are hybridized to the labeled oligonucleotide, primer, or probe. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels include, but are not limited to, the following: radioisotopes or radionuclides (for example, $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; pre-determined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In some embodiments, the moiety itself may not be detectably labeled but may become detectable upon reaction with yet another moiety.

The term "conjugate" refers to an antibody that is chemically linked to a second chemical moiety, such as a therapeutic or cytotoxic agent. The term "agent" includes a chemical compound, a mixture of chemical compounds, a biological macromolecule, or an extract made from biological materials. In some embodiments, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

As used herein, the term "flow cytometry" generally refers to a technique for characterizing biological particles, such as whole cells or cellular constituents, by flow cytometry. Methods for performing flow cytometry on samples of immune cells are well known in the art (see e.g., Jaroszeski et al., Method in Molecular Biology (1998), vol. 91: Flow Cytometry Protocols, Humana Press; Longobanti Givan, (1992) Flow Cytometry, First Principles, Wiley Liss). All known forms of flow cytometry are intended to be included, particularly fluorescence activated cell sorting (FACS), in which fluorescent labeled molecules are evaluated by flow cytometry.

The term "amplification" refers to the process of producing one or more copies of a nucleic acid sequence or its complement. Amplification may be linear or exponential (e.g., PCR).

The technique of "polymerase chain reaction" or "PCR" as used herein generally refers to a procedure wherein a specific region of nucleic acid, such as RNA and/or DNA, is amplified as described, for example, in U.S. Pat. No. 4,683, 195. Generally, oligonucleotide primers are designed to hybridize to opposite strands of the template to be amplified, a desired distance apart. PCR can be used to amplify specific RNA sequences, specific DNA sequences from total genomic DNA, and cDNA transcribed from total cellular RNA, bacteriophage or plasmid sequences, etc.

"Quantitative real time PCR" or "qRT-PCR" refers to a form of PCR wherein the PCR is performed such that the amounts, or relative amounts of the amplified product can be quantified. This technique has been described in various publications including Cronin et al., Am. J. Pathol. 164(1): 35-42 (2004); and Ma et al., Cancer Cell 5:607-616 (2004).

The term "target sequence," "target nucleic acid," or "target nucleic acid sequence" refers generally to a polynucleotide sequence of interest, e.g., a polynucleotide sequence that is targeted for amplification using, for example, qRT-PCR.

The term "detection" includes any means of detecting, including direct and indirect detection.

II. Therapeutic Methods

The invention provides methods of treating cancer in patients in need of such treatment. The methods include (i) administering one or more dosages of one or more anti-cancer therapies to the patients, (ii) obtaining one or more peripheral blood test samples from the patients, (iii) measuring ICOS and/or T-bet levels of CD4+ T cells present in the one or more peripheral blood test samples, (iv) determining if there is a population of the CD4+ T cells in any of the one or more peripheral blood test samples having elevated ICOS and/or T-bet levels when compared to a control, and (v) administering (a) one or more additional dosages of the one or more anti-cancer therapies, or (b) an anti-ICOS agonist (e.g., an anti-ICOS agonist antibody) in the absence of one or more additional dosages of the one or more anti-cancer therapies, to the patients if any of the one or more peripheral blood test samples is determined to include a population of CD4+ T cells having elevated ICOS and/or T-bet levels. Optionally, anti-ICOS agonist antibodies are also administered to patients determined to have CD4+ T cells having elevated ICOS and/or T-bet levels, and who are being administered one or more additional dosages of the one or more anti-cancer therapies, when the one or more anti-cancer therapies is not anti-ICOS agonist antibody therapy.

The invention also provides methods for determining whether a subject may benefit from continued treatment with one or more anti-cancer therapies. The methods include determining ICOS and/or T-bet levels of peripheral CD4+ T cells of a sample of blood of the subject, wherein detection of increased ICOS and/or T-bet levels relative to a control indicates that the subject may benefit from (a) the continued treatment, optionally in combination with treatment with an anti-ICOS antibody agonist when the one or more anti-cancer therapies does not include anti-ICOS antibody agonist treatment, or (b) anti-ICOS agonist (e.g., anti-ICOS agonist antibody) treatment in the absence of continued treatment with the one or more anti-cancer therapies.

Patients that can be treated as described herein are patients having a cancer. The type of cancer can be any type of cancer listed herein or otherwise known in the art. Exemplary types of cancer include, but are not limited to, gastric cancer, breast cancer (e.g., triple negative breast cancer (TNBC)), lung cancer (e.g., non-small cell lung cancer (NSCLC)), melanoma, renal cell carcinoma (RCC), bladder cancer, endometrial cancer, diffuse large B-cell lymphoma (DLBCL), Hodgkin's lymphoma, ovarian cancer, and head and neck squamous cell cancer (HNSCC). Also see the definition of cancer, above, for additional cancer types that can be treated according to the methods of the invention.

Patients that can be treated as described herein include patients who have not previously received an anti-cancer therapy and patients who have received previous (e.g., 1, 2, 3, 4, 5, or more) doses or cycles of one or more (e.g., 1, 2, 3, 4, 5, or more) anti-cancer therapies.

Any of the anti-cancer therapies listed herein and others known in the art can be used in connection with the methods of the invention. In some embodiments, the one or more anti-cancer therapies is two or more anti-cancer therapies. In some embodiments, the one or more anti-cancer therapies is three or more anti-cancer therapies. Specific, non-limiting examples of anti-cancer therapies that can be used in the invention including, e.g., immunotherapies, chemotherapies, and cancer vaccines, among others, are provided below.

In some embodiments, the one or more anti-cancer therapies is administered one time prior to obtaining the one or more peripheral blood test samples from the patient. In some embodiments, the one or more anti-cancer therapies is administered more than once prior to obtaining the one or more peripheral blood test samples from the patient. In some embodiments, the one or more anti-cancer therapies is administered two or more (e.g., three or more, four or more, or five or more) times prior to obtaining the one or more peripheral blood test samples from the patient.

In some embodiments, the one or more anti-cancer therapies is administered to the patient multiple times at regular intervals. These multiple administrations can also be referred to as administration cycles or therapy cycles. In some embodiments, the one or more anti-cancer therapies is administered to the patient for more than two cycles, more than three cycles, more than four cycles, more than five cycles, more than ten cycles, more than fifteen cycles, or more than twenty cycles.

In some embodiments, the regular interval is a dosage every week, a dosage every two weeks, a dosage every three weeks, a dosage every four weeks, a dosage every five weeks, a dosage every six weeks, a dosage every seven weeks, a dosage every eight weeks, a dosage every nine weeks, a dosage every ten weeks, a dosage every eleven weeks, or a dosage every twelve weeks.

In some instances the one or more peripheral blood test samples is obtained from the patient fewer than four weeks (e.g., fewer than three weeks, fewer than two weeks, or less than one week) after the administration of the one or more anti-cancer therapies.

In some embodiments, the one or more peripheral blood test samples are obtained as multiple samples obtained at a time concurrent with one or more of the administrations. In some embodiments, the one or more peripheral blood test samples are obtained as multiple samples obtained during a time intervening the multiple administrations.

In some embodiments, the control sample is a peripheral blood sample obtained from the same patient prior to the administration of a first dosage (e.g., the prior to the first cycle) of the one or more anti-cancer therapies. In some embodiments, the control sample is a peripheral blood sample obtained from the same patient prior to the administration of a second or further (e.g., third, fourth, fifth, or further) dosage of the one or more anti-cancer therapies preceding collection of the peripheral blood test sample. In some embodiments, the control sample is a peripheral blood sample obtained from a healthy patient not receiving anti-cancer therapies. In some embodiments, the control is a level known or determined to correspond to the level in a control sample as described herein.

In some embodiments, the method further includes storing a portion of the one or more peripheral blood test samples. In some embodiments, wherein a portion of the CD4+ T cells from the peripheral blood test sample is determined to have elevated ICOS and/or T-bet levels relative to CD4+ T cells from a control sample, the method further involves isolating the CD4+ T cells having elevated ICOS and/or T-bet levels and storing the CD4+ T cells under conditions suitable for maintaining the viability of the CD4+ T cells. Any method of storage known in the art suitable for maintaining viability of CD4+ T cells may be used. In some embodiments, the stored CD4+ T cells are stored in a cell culture medium. In some embodiments, the stored CD4+ T cells are stored at a concentration of greater than 100,000 cells/mL. In some embodiments, the stored CD4+ T cells are stored at a concentration between 100,000 cells/mL and 100 million cells/mL. In some embodiments, the invention provides a suspension of stored CD4+ T cells obtained, accordingly.

In some embodiments, the method further includes administering a therapeutic anti-ICOS agonist antibody to the patient if any of the one or more peripheral blood test samples is determined to comprise a population of CD4+ T cells having elevated ICOS and/or T-bet levels. In some embodiments, a detected population of CD4+ T cells having elevated ICOS and/or T-bet levels is or includes a new, separate CD4+ T cell population, which was induced by the one or more anti-cancer therapies. Information regarding therapeutic anti-ICOS agonist antibodies is provided below.

In some embodiments, the method further includes halting the administration of the one or more anti-cancer therapies if a population of CD4+ T cells having elevated ICOS and/or T-bet levels relative to a control sample is not observed after a pre-determined number of administration cycles. The predetermined number of administration cycles may be four or more cycles (e.g., five or more cycles, six or more cycles, or seven or more cycles, eight or more cycles, nine or more cycles, or ten or more cycles). In some embodiments, the method further includes halting the administration of the one or more anti-cancer therapies before the pre-determined number of administration cycles (e.g., four or more cycles) if a population of CD4+ T cells having elevated ICOS and/or T-bet levels relative to a control sample is not observed and, optionally, the patient is determined to have progressive disease by a routine method known in the art (e.g., progressive disease identified by radiographic progression per RECIST 1.1 criteria; see, e.g., the criteria listed above).

III. Exemplary Anti-Cancer Therapies for Use in the Methods of the Invention As examples, any anti-cancer therapy listed herein or otherwise known in the art, can be used in connection with the methods described herein. Exemplary anti-cancer therapies are described below.

a. Immunotherapies

In some embodiments, the one or more anti-cancer therapies is an immunotherapy. The interaction between cancer and the immune system is complex and multifaceted. See de Visser et al., Nat. Rev. Cancer (2006) 6:24-37. While many cancer patients appear to develop an anti-tumor immune response, cancers also develop strategies to evade immune detection and destruction. Recently, immunotherapy has been developed for the treatment and prevention of cancer and other disorders. Immunotherapy provides the advantage of cell specificity that other treatment modalities lack. As such, methods for enhancing the efficacy of immune based therapies can be clinically beneficial.

i. Therapeutic Anti-ICOS Antibodies

Therapeutic anti-ICOS antibodies that can be used in the invention include, but are not limited to, humanized antibodies, chimeric antibodies, human antibodies, and antibodies comprising any of the heavy chain and/or light chain CDRs discussed herein. In some embodiments, the antibody is an isolated antibody. In some embodiments, the antibody is a monoclonal antibody. In some embodiments, the anti-ICOS antibody is an anti-ICOS agonist antibody. See WO 2016/154177 and WO 2017/070423, which are each specifically incorporated herein by reference.

In some embodiments, the therapeutic anti-ICOS agonist antibody includes at least one, two, there, four, five, or all six CDRs selected from (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7; (d) LCDR1 comprising the amino acid sequence of SEQ ID NO: 8; (e) LCDR2 comprising the amino acid sequence of SEQ ID NO: 9; and (f) LCDR3 comprising the amino acid sequence of SEQ ID NO: 10. In various embodiments, one or more of the CDRs includes a substitution or deletion that does not destroy specific binding to ICOS. In some embodiments, one or more of the CDRs includes 1, 2, 3, or more substitutions, which may optionally comprise substitutions with conservative amino acids. In some embodiments, one or more of the CDRs includes 1, 2, 3, or more deletions.

In some embodiments, the therapeutic anti-ICOS antibody comprises six CDRs including (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7; (d) LCDR1 comprising the amino acid sequence of SEQ ID NO: 8; (e) LCDR2 comprising the amino acid sequence of SEQ ID NO: 9; and (f) LCDR3 comprising the amino acid sequence of SEQ ID NO: 10.

In some embodiments, a therapeutic anti-ICOS antibody comprises a heavy chain variable region and a light chain variable region. In some embodiments, a therapeutic anti-ICOS antibody comprises at least one heavy chain comprising a heavy chain variable region and at least a portion of a heavy chain constant region, and at least one light chain comprising a light chain variable region and at least a portion of a light chain constant region. In some embodiments, a therapeutic anti-ICOS antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some embodiments, the heavy chain is the region of the anti-ICOS antibody that comprises the three heavy chain CDRs. In some embodiments, the light chain is the region of the therapeutic anti-ICOS antibody that comprises the three light chain CDRs.

In some embodiments, the therapeutic anti-ICOS antibody comprises at least one, at least two, or all three VH CDR sequences selected from (a) HCDR1 comprising the amino acid sequence of SEQ ID NO: 5; (b) HCDR2 comprising the amino acid sequence of SEQ ID NO: 6; and (c) HCDR3 comprising the amino acid sequence of SEQ ID NO: 7.

In some embodiments, the therapeutic antibody comprises at least one, at least two, or all three VL CDR sequences selected from (a) LCDR1 comprising the amino acid sequence of SEQ ID NO: 8; (b) LCDR2 comprising the amino acid sequence of SEQ ID NO: 9; and (c) LCDR3 comprising the amino acid sequence of SEQ ID NO: 10.

In some embodiments, the therapeutic anti-ICOS antibody comprises (I) a VH domain comprising at least one, at least two, or all three VH CDR sequences selected from (a) HCDR1 comprising the amino acid sequence of SEQ ID NO: 5; (b) HCDR2 comprising the amino acid sequence of SEQ ID NO: 6; and (c) HCDR3 comprising the amino acid sequence of SEQ ID NO: 7; and (II) a VL domain comprising at least one, at least two, or all three VL CDR sequences selected from (d) LCDR1 comprising the amino acid sequence of SEQ ID NO: 8; (e) LCDR2 comprising the amino acid sequence of SEQ ID NO: 9; and (f) LCDR3 comprising the amino acid sequence of SEQ ID NO: 10.

In some embodiments, a therapeutic anti-ICOS antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 3. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, but an anti-ICOS antibody comprising that sequence retains the ability to bind to ICOS. In some embodiments, a total of 1 to 10 amino acids have been substituted, inserted, and/or deleted in SEQ ID NO: 3. In some embodiments, substitutions, insertions, or deletions occur in regions outside the CDRs (that is, in the FRs). Optionally, the therapeutic anti-ICOS antibody comprises the VH sequence in SEQ ID NO: 3, including post-translational modifications of that sequence.

In some embodiments, the VH comprises: (a) HCDR1 comprising the amino acid sequence of SEQ ID NO: 5; (b) HCDR2 comprising the amino acid sequence of SEQ ID NO: 6; and (c) HCDR3 comprising the amino acid sequence of SEQ ID NO: 7.

In some embodiments, a therapeutic anti-ICOS antibody is provided, wherein the antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 4. In some embodiments, a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-ICOS antibody comprising that sequence retains the ability to bind to ICOS. In some embodiments, a total of 1 to 10 amino acids have been substituted, inserted, and/or deleted in SEQ ID NO: 4. In some embodiments, the substitutions, insertions, or deletions occur in regions outside the CDRs (that is, in the FRs). Optionally, the therapeutic anti-ICOS antibody comprises the $V_L$ sequence in SEQ ID NO: 4, including post-translational modifications of that sequence.

In some embodiments, the VL comprises: (a) LCDR1 comprising the amino acid sequence of SEQ ID NO: 8; (b) LCDR2 comprising the amino acid sequence of SEQ ID NO: 9; and (c) LCDR3 comprising the amino acid sequence of SEQ ID NO: 10.

In some embodiments, a therapeutic anti-ICOS antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 3 and a light chain variable domain (VL) having at least 90%, 91%, 92%, 93%, 94%, 95%, 96%, 97%, 98%, 99%, or 100% sequence identity to the amino acid sequence of SEQ ID NO: 4. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, and a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-ICOS antibody comprising that sequence retains the ability to bind to ICOS. In some embodiments, a total of 1 to 10 amino acids have been substituted, inserted, and/or deleted in SEQ ID NO: 3. In some embodiments, a total of 1 to 10 amino acids have been substituted, inserted, and/or deleted in SEQ ID NO: 4. In some embodiments, substitutions, insertions, or deletions occur in regions outside the CDRs (that is, in the FRs). Optionally, the therapeutic anti-ICOS antibody comprises the VH sequence in SEQ ID NO: 3 and the VL sequence of SEQ ID NO: 4, including post-translational modifications of one or both sequence.

In some embodiments, the therapeutic anti-ICOS antibody comprises (I) a VH domain comprising: (a) HCDR1 comprising the amino acid sequence of SEQ ID NO: 5; (b) HCDR2 comprising the amino acid sequence of SEQ ID NO: 6; and (c) HCDR3 comprising the amino acid sequence of SEQ ID NO: 7; and (II) a VL domain comprising: (d) LCDR1 comprising the amino acid sequence of SEQ ID NO: 8; (e) LCDR2 comprising the amino acid sequence of SEQ ID NO: 9; and (f) LCDR3 comprising the amino acid sequence of SEQ ID NO: 10.

In some embodiments, a therapeutic anti-ICOS antibody comprises a VH as in any of the embodiments provided herein, and a VL as in any of the embodiments provided herein. In some embodiments, the antibody comprises the VH and VL sequences in SEQ ID NO: 3 and SEQ ID NO: 4, respectively, including post-translational modifications of those sequences.

In some embodiments, a therapeutic anti-ICOS antibody comprises a heavy chain comprising the amino acid sequence of SEQ ID NO: 1, or a variant thereof.

In some embodiments, a therapeutic anti-ICOS antibody comprises a light chain comprising the amino acid sequence of SEQ ID NO: 2, or a variant thereof.

In some embodiments, a therapeutic anti-ICOS antibody comprises a heavy chain comprising the amino acid sequence of SEQ ID NO: 1 and a light chain comprising the amino acid sequence of SEQ ID NO: 2, or variants thereof.

In some embodiments, the therapeutic anti-ICOS antibody comprises the six CDRs as described above and binds to ICOS. In some embodiments, the therapeutic anti-ICOS antibody comprises the six CDRs as described above, binds to ICOS and increases the number of Teff cells and/or activates Teff cells and/or decreases the number of Treg cells and/or increases the ratio of Teff cells to Treg cells in a mammal, such as a human. In some embodiments, the Treg cells are CD4+ FoxP3+ T cells. In some embodiments, the Teff cells are CD8+ T cells. In some embodiments, the Teff cells are CD4+ FoxP3− T cells and/or CD8+ T cells.

Exemplary therapeutic anti-ICOS antibodies include, but are not limited to, JTX-2011 (vopratelimab; Jounce Therapeutics; US 2016/0304610; WO 2016/154177; WO 2017/070423) and BMS-986226 (Bristol-Myers Squibb).

In general, therapeutic anti-ICOS antibodies can be administered in an amount in the range of about 10 µg/kg body weight to about 100 mg/kg body weight per dose. In some embodiments, therapeutic anti-ICOS antibodies may be administered in an amount in the range of about 50 µg/kg body weight to about 5 mg/kg body weight per dose. In some embodiments, therapeutic anti-ICOS antibodies may be administered in an amount in the range of about 100 µg/kg body weight to about 10 mg/kg body weight per dose. In some embodiments, therapeutic anti-ICOS antibodies may be administered in an amount in the range of about 100 µg/kg body weight to about 20 mg/kg body weight per dose. In some embodiments, therapeutic anti-ICOS antibodies may be administered in an amount in the range of about 0.5 mg/kg body weight to about 20 mg/kg body weight per dose. In some embodiments, anti-ICOS antibodies may be administered in an amount in the range of about 0.05 mg/kg body weight to about 10 mg/kg body weight per dose. In some embodiments, anti-ICOS antibodies may be administered in an amount in the range of about 5 mg/kg body weight or lower, for example less than 4, less than 3, less than 2, or less than 1 mg/kg of the antibody. In specific examples, therapeutic anti-ICOS antibodies are administered at 0.1 mg/kg, 0.3 mg/kg, or 1.0 mg/kg, once every 3, 6, 9, or 12 weeks.

ii. Anti-CTLA-4 Antagonist Antibodies

In some embodiments, the one or more anti-cancer therapies is an anti-CTLA-4 antagonist antibody. An anti-CTLA-4 antagonist antibody refers to an agent capable of inhibiting the activity of cytotoxic T-lymphocyte-associated protein 4 (CTLA-4), thereby activating the immune system. The CTLA-4 antagonist may bind to CTLA-4 and reverse CTLA-4-mediated immunosuppression. A non-limiting exemplary anti-CTLA-4 antibody is ipilimumab (YERVOY®, BMS), which may be administered according to methods known in the art, e.g., as approved by the US FDA. For example, ipilimumab may be administered in the amount of 3 mg/kg intravenously over 90 minutes every three weeks for a total of 4 doses (unresectable or metastatic melanoma); or at 10 mg/kg intravenously over 90 minutes every three weeks for a total of 4 doses, followed by 10 mg/kg every 12 weeks for up to 3 years or until documented recurrence or unacceptable toxicity (adjuvant melanoma).

iii. OX40 Agonist Antibodies

In some embodiments, the one or more anti-cancer therapies is an agonist anti-OX40 antibody. An OX40 agonist antibody refers to an agent that induces the activity of OX40, thereby activating the immune system and enhancing anti-tumor activity. Non-limiting, exemplary agonist anti-OX40 antibodies are Medi6469, MedImmune, and MOXR0916/RG7888, Roche. These antibodies may be administered according to methods and in regimens determined to be appropriate by those of skill in the art.

iv. PD-1 Therapies

In some embodiments, the one or more anti-cancer therapies is a PD-1 therapy. A PD-1 therapy encompasses any therapy that modulates PD-1 binding to PD-L1 and/or PD-L2. PD-1 therapies may, for example, directly interact with PD-1 and/or PD-L1. In some embodiments, a PD-1 therapy includes a molecule that directly binds to and/or influences the activity of PD-1. In some embodiments, a PD-1 therapy includes a molecule that directly binds to and/or influences the activity of PD-L1. Thus, an antibody that binds to PD-1 or PD-L1 and blocks the interaction of PD-1 to PD-L1 is a PD-1 therapeutic. When a desired subtype of PD-1 therapy is intended, it will be designated by the phrase "PD-1 specific" for a therapy involving a molecule that interacts directly with PD-1, or "PD-L1 specific" for a molecule that interacts directly with PD-L1, as appropriate. Unless designated otherwise, all disclosure contained herein regarding PD-1 therapy applies to PD-1 therapy generally, as well as PD-1 specific and/or PD-L1 specific therapies.

Non-limiting, exemplary PD-1 therapies include nivolumab (OPDIVO®, BMS-936558, MDX-1106, ONO-4538); pidilizumab, lambrolizumab/pembrolizumab (KEYTRUDA, MK-3475); BGB-A317, tislelizumab (BeiGene/Celgene); durvalumab (anti-PD-L1 antibody, MEDI-4736; AstraZeneca/MedImmune); RG-7446; avelumab (anti-PD-L1 antibody; MSB-0010718C; Pfizer); AMP-224; BMS-936559 (anti-PD-L1 antibody); AMP-514; MDX-1105; A B-011; anti-LAG-3/PD-1; spartalizumab (CoStim/Novartis); anti-PD-1 antibody (Kadmon Pharm.); anti-PD-1 antibody (Immunovo); anti-TEVI-3/PD-I antibody (AnaptysBio); anti-PD-L1 antibody (CoStim/Novartis); RG7446/MPDL3280A (anti-PD-L1 antibody, Genentech/Roche); KD-033 (Kadmon Pharm.); AGEN-2034 (Agenus); STI-A1010; STI-A1110; TSR-042; atezolizumab (TECENTRIQ™); and other antibodies that are directed against programmed death-1 (PD-1) or programmed death ligand 1 (PD-L1).

PD-1 therapies are administered according to regimens that are known in the art, e.g., US FDA-approved regimens. In one example, nivolumab is administered as an intravenous infusion over 60 minutes in the amount of 240 mg every two weeks (unresectable or metastatic melanoma, adjuvant treatment for melanoma, non-small cell lung cancer (NSCLC), advanced renal cell carcinoma, locally advanced renal cell carcinoma, MSI-H or dMMR metastatic colorectal cancer, and hepatocellular carcinoma) or in the amount of 3 mg/kg every three weeks (classical Hodgkin lymphoma; recurrent or metastatic squamous cell carcinoma of the head and neck). In another example, pembrolizumab is administered by intravenous infusion over 30 minutes in the amount of 200 mg, once every three weeks. In another example, atezolizumab is administered by intravenous infusion over 60 minutes in the amount of 1200 mg every three weeks. In another example, avelumab is administered by intravenous infusion over 60 minutes in the amount of 10 mg/kg every two weeks. In another example, durvalumab is administered by intravenous infusion over 60 minutes in the amount of 10 mg/kg every two weeks.

v. TIGIT Antagonists

In some embodiments, the one or more anti-cancer therapies is TIGIT antagonist. A TIGIT antagonist refers to an agent capable of antagonizing or inhibiting the activity of T-cell immunoreceptor with Ig and ITIM domains (TIGIT), thereby reversing TIGIT-mediated immunosuppression. A non-limiting exemplary TIGIT antagonist is BMS-986207 (Bristol-Myers Squibb/Ono Pharmaceuticals). These agents may be administered according to methods and in regimens determined to be appropriate by those of skill in the art.

vi. IDO Inhibitors

In some embodiments, the one or more anti-cancer therapies is an IDO inhibitor. An IDO inhibitor refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. A reversible IDO inhibitor is a compound that reversibly inhibits IDO enzyme activity either at the catalytic site or at a non-catalytic site while an irreversible IDO inhibitor is a compound that irreversibly inhibits IDO enzyme activity by forming a covalent bond with the enzyme. Non-limiting exemplary IDO inhibitors are described, e.g., in US 2016/0060237; and US 2015/0352206. Non-limiting exemplary IDO inhibitors include Indoximod (New Link Genetics), INCB024360 (Incyte Corp), 1-methyl-D-tryptophan (New Link Genetics), and GDC-0919/navoximod (Genentech/New Link Genetics). These agents may be administered according to methods and in regimens determined to be appropriate by those of skill in the art.

vii. RORγ Agonists

In some embodiments, the one or more anti-cancer therapies is a RORγ agonist. RORγ agonists refer to an agent capable of inducing the activity of retinoic acid-related orphan receptor gamma (RORγ), thereby decreasing immunosuppressive mechanisms. Non-limiting exemplary RORγ agonists include, but are not limited to, LYC-55716 (Lycera/Celgene) and INV-71 (Innovimmune). These agents may be administered according to methods and in regimens determined to be appropriate by those of skill in the art.

b. Chemotherapies

In some embodiments, the one or more anti-cancer therapies is a chemotherapeutic agent. Exemplary chemotherapeutic agents that can be used include, but are not limited to, capecitabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, ABRAXANE® (protein-bound paclitaxel), pemetrexed, vinorelbine, vincristine, erlotinib, afatinib, gefitinib, crizotinib, dabrafenib, trametinib, vemurafenib, and cobimetanib. These agents may be administered according to methods and in regimens determined to be appropriate by those of skill in the art.

c. Cancer Vaccines

In some embodiments, the one or more anti-cancer therapies is a cancer vaccine. Cancer vaccines have been investigated as a potential approach for antigen transfer and activation of dendritic cells. In particular, vaccination in combination with immunologic checkpoints or agonists for co-stimulatory pathways have shown evidence of overcoming tolerance and generating increased anti-tumor response. A range of cancer vaccines have been tested that employ different approaches to promoting an immune response against the tumor (see, e.g., Emens L A, Expert Opin Emerg Drugs 13(2): 295-308 (2008)). Approaches have been designed to enhance the response of B cells, T cells, or professional antigen-presenting cells against tumors. Exemplary types of cancer vaccines include, but are not limited to, peptide-based vaccines that employ targeting distinct tumor antigens, which may be delivered as peptides/proteins or as genetically-engineered DNA vectors, viruses, bacteria, or the like; and cell biology approaches, for example, for cancer vaccine development against less well-defined targets, including, but not limited to, vaccines developed from patient-derived dendritic cells, autologous tumor cells or tumor cell lysates, allogeneic tumor cells, and the like.

Exemplary cancer vaccines include, but are not limited to, dendritic cell vaccines, oncolytic viruses, tumor cell vaccines, etc. In some embodiments, such vaccines augment the anti-tumor response. Examples of cancer vaccines also include, but are not limited to, MAGES vaccine (e.g., for melanoma and bladder cancer), MUC1 vaccine (e.g., for breast cancer), EGFRv3 (such as Rindopepimut, e.g., for brain cancer, including glioblastoma multiforme), or ALVAC-CEA (e.g., for CEA+ cancers).

Non-limiting exemplary cancer vaccines also include Sipuleucel-T, which is derived from autologous peripheral-blood mononuclear cells (PBMCs) that include antigen-presenting cells (see, e.g., Kantoff P W et al., N Engl J Med. 363:411-22 (2010)). In Sipuleucel-T generation, the patient's PBMCs are activated ex vivo with PA2024, a recombinant fusion protein of prostatic acid phosphatase (a prostate antigen) and granulocyte-macrophage colony-stimulating factor (an immune-cell activator). Another approach to a candidate cancer vaccine is to generate an immune response against specific peptides mutated in tumor tissue, such as melanoma (see, e.g., Carreno et al., Science 348:6236, 2015). Such mutated peptides may, in some embodiments, be referred to as neoantigens. As a non-limiting example of the use of neoantigens in tumor vaccines, neoantigens in the tumor predicted to bind the major histocompatibility complex protein HLA-A*02:01 are identified for individual patients with a cancer, such as melanoma. Dendritic cells from the patient are matured ex vivo, then incubated with neoantigens. The activated dendritic cells are then administered to the patient. In some embodiments, following administration of the cancer vaccine, robust T-cell immunity against the neoantigen is detectable.

In some such embodiments, the cancer vaccine is developed using a neoantigen. In some embodiments, the cancer vaccine is a DNA vaccine. In some embodiments, the cancer vaccine is an engineered virus comprising a cancer antigen, such as PROSTVAC (rilimogene galvacirepvec/rilimogene glafolivec). In some embodiments, the cancer vaccine comprises engineered tumor cells, such as GVAX, which is a granulocyte-macrophage colony-stimulating factor (GM-CSF) gene-transfected tumor cell vaccine (see, e.g., Nemunaitis, Expert Rev. Vaccines 4:259-274, 2005).

The vaccines may be administered according to methods and in regimens determined to be appropriate by those of skill in the art.

d. Additional Exemplary Anti-Cancer Therapies

Further non-limiting, exemplary anti-cancer therapies include Luspatercept (Acceleron Pharma/Celgene); Motolimod (Array BioPharma/CelgeneNentiRx Pharmaceuticals/Ligand); GI-6301 (Globelmmune/Celgene/NantWorks); GI-6200 (Globelmmune/Celgene/NantWorks); BLZ-945 (Celgene/Novartis); ARRY-382 (Array BioPharma/Celgene), or any of the anti-cancer therapies provided in Table 2. These agents may be administered according to methods and in regimens determined to be appropriate by those of skill in the art. In some embodiments, the one or more anti-cancer therapies includes surgery and/or radiation therapy. Accordingly, the anti-cancer therapies can optionally be utilized in the adjuvant or neoadjuvant setting.

e. Combinations

In various embodiments, the anti-cancer treatment administered to a patient is a combination of one or more (e.g., two, three, or more) anti-cancer treatments including, e.g., one or more of the anti-cancer treatments listed above or elsewhere herein.

In various examples, an anti-ICOS agonist antibody (e.g., an antibody described above, such as JTX-2011) is administered in combination with another immunotherapy (see, e.g., above). In one example, an anti-ICOS agonist antibody (e.g., an antibody described above, such as JTX-2011) is administered in combination with a PD-1 therapy (e.g., a PD-1 therapy listed above). Thus, the invention includes, in various examples, administration of an anti-ICOS agonist antibody (e.g., JTX-2011) in combination with one or more of nivolumab, pidilizumab, lambrolizumab/pembrolizumab, BGB-A317, tislelizumab, durvalumab, RG-7446, avelumab, AMP-224, BMS-936559, AMP-514, MDX-1105, A B-011, anti-LAG-3/PD-1, spartalizumab (CoStim/Novartis); anti-PD-1 antibody (Kadmon Pharm.); anti-PD-1 antibody (Immunovo); anti-TEVI-3/PD-1 antibody (AnaptysBio); anti-PD-L1 antibody (CoStim/Novartis); RG7446/MPDL3280A, KD-033 (Kadmon Pharm.); AGEN-2034 (Agenus), STI-A1010, STI-A1110, TSR-042, atezolizumab, and other antibodies that are directed against programmed death-1 (PD-1) or programmed death ligand 1 (PD-L1). In one specific example, JTX-2011 is administered with nivolumab.

Optionally, the combinations noted above further include one or more additional anti-cancer agents (e.g., immunotherapies). Accordingly, the combinations noted above can optionally include one or more of an anti-CTLA-4 antagonist antibody (e.g., ipilimumab), an anti-OX40 antibody (e.g., Medi6469), or MOXR0916/RG7888), a TIGIT antagonist (e.g., BMS-986207), an IDO inhibitor (e.g., indoximod, INCB024360, 1-methyl-D-tryptophan, or GDC-0919/navoximod), an RORγ agonist (e.g., LYC-55716 and INV-71), or a chemotherapeutic agent (see, e.g., above), or a cancer vaccine (see, e.g., above).

In other examples, a combination of the invention includes an anti-ICOS agonist antibody (e.g., an antibody described above, such as JTX-2011) and one or more of an anti-CTLA-4 antagonist antibody (e.g., ipilimumab), an anti-OX40 antibody (e.g., Medi6469), or MOXR0916/RG7888), a TIGIT antagonist (e.g., BMS-986207), an IDO inhibitor (e.g., indoximod, INCB024360, 1-methyl-D-tryptophan, or GDC-0919/navoximod), an RORγ agonist (e.g., LYC-55716 and INV-71), or a chemotherapeutic agent (see, e.g., above), or a cancer vaccine (see, e.g., above).

In various examples, the components of a combination are administered according to dosing regimens described herein (e.g., US FDA-approved dosing regimens; see above), or using other regimens determined to be appropriate by those of skill in the art.

IV. Pharmaceutical Compositions and Dosing

Compositions including one or more anti-cancer therapies are provided in formulations with a wide variety of pharmaceutically acceptable carriers, as determined to be appropriate by those of skill in the art (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, $7^{th}$ ed., Lippincott, Williams and Wilkins (2004); Kibbe et al., Handbook of Pharmaceutical Excipients, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

Anti-cancer therapies are administered in the practice of the methods of the present invention as is known in the art (e.g., according to FDA-approved regimens) or as indicated elsewhere herein (see, e.g., above). In some embodiments, anti-cancer therapies of the invention are administered in amounts effective for treatment of cancer. The therapeutically effective amount is typically dependent on the weight of the subject being treated, his or her physical or health condition, the extensiveness of the condition to be treated, the age of the subject being treated, pharmaceutical formulation methods, and/or administration methods (e.g., administration time and administration route).

In some embodiments, anti-cancer therapies can be administered in vivo by various routes, including, but not limited to, intravenous, intra-arterial, parenteral, intratumoral, intraperitoneal, or subcutaneous. The appropriate formulation and route of administration can be selected by those of skill in the art according to the intended application.

V. Exemplary Methods for Detection of Total ICOS and/or T-Bet Expression Levels

Provided herein are methods of assessing patient responsiveness to one or more anti-cancer therapies. In some embodiments, methods of identifying a subject who may benefit from continued treatment with one or more anti-cancer therapies, optionally in combination with an anti-ICOS agonist antibody, are provided.

a. Exemplary Antibody-Based Detection Methods

In some embodiments, the methods include determining whether a patient treated with one or more anti-cancer therapies has CD4+ T cells in peripheral blood that have elevated expression of ICOS and/or T-bet using, e.g., an anti-ICOS and/or anti-T-bet antibody, polypeptide, or polynucleotide. In some embodiments, the methods of detection include contacting a patient sample (e.g., a peripheral blood sample, or a fraction thereof) with an antibody, polypeptide, or polynucleotide, and determining whether the level of binding differs from that of a control. In some embodiments, CD4+ T cells from the peripheral blood test sample are contacted with an anti-ICOS detection antibody and/or an anti-T-bet detection antibody and binding between the antibody (or antibodies) and the CD4+ T cells is determined. When CD4+ T cells from a test sample are shown to have an increase in binding activity to the antibody (or antibodies), as compared to CD4+ T cells from a control sample, continued treatment with the one or more anti-cancer therapies is indicated, optionally in combination with anti-ICOS agonist antibody treatment, as described herein.

Various methods known in the art for detecting specific antibody-antigen binding can be used. These assays include, but are not limited to, flow cytometry (including, for example, fluorescent activating cell sorting (FACS)), indirect immune-fluorescence, solid phase enzyme-linked immunosorbent assay (ELISA), ELISpot assays, fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), western blotting (including in cell western), immunofluorescent staining, microengraving (see Han et al., Lab Chip 10(11):1391-1400, 2010), Quant-iT and Qubit protein assay kits, NanoOrange protein quantitation kit, CBQCA protein quantitation kits, EZQ protein quantitation kit, Click-iT reagents, Pro-Q Diamond phosphoprotein stain, Pro-Q glycoprotein stain kits, peptide and protein sequencing, N-terminal amino acid analysis (LifeScience Technologies, Grand Island, N.Y.), chemiluminescence or colorimetric based ELISA cytokine Arrays (Signosis) Intracellular Cytokine Staining (ICS), BD Phosflow™ and BD™ Cytometric Bead Arrays (BD Sciences, San Jose, Calif.); CyTOF Mass Cytometer (DVS Sciences, Sunnyvale Calif.); Mass Spectrometry, Microplate capture and detection assay (Thermo Scientific, Rockland, Ill.), Multiplex Technologies (for example Luminex, Austin, Tex.); FlowCellect™ T-cell Activation Kit (EMD Millipore); Surface Plasmon Resonance (SPR)-based technologies (for example Biacore, GE Healthcare Life Sciences, Uppsala, Sweden); CD4+ Effector Memory T-cell Isolation Kit and CD8+ CD45RA+ Effector T-cell Isolation Kit (Miltenyi Biotec Inc., CA); The EasySep™ Human T-cell Enrichment Kit (StemCells, Inc., Vancouver, Canada); HumanThl/Th2/Thl7 Phenotyping Kit (BD Biosciences, CA); immunofluorescent staining of incorporated bromodeoxyuridine (BrdU) or 7-aminoactinomycin D. See also, Current Protocols in Immunology (2004) sections 3.12.1-3.12.20 by John Wiley & Sons, Inc., or Current Protocols in Immunology (2013) or by John Wiley & Sons, Inc., the contents of which are herein incorporated by reference in their entirety.

An indicator moiety, or label group, can be attached to the subject antibodies and is selected so as to meet the needs of various uses of the method which are often dictated by the availability of assay equipment and compatible immunoassay procedures.

Appropriate labels include, without limitation, radionuclides (for example $^{125}I$, $^{131}I$, $^{35}S$, $^{3}H$, or $^{32}P$), enzymes (for example, alkaline phosphatase, horseradish peroxidase, luciferase, or β-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

In some instances, the anti-ICOS detection antibodies need not be labeled, and the presence thereof can be detected using a second labeled antibody which binds to the first anti-ICOS antibody.

In some instances, the anti-T-bet detection antibodies need not be labeled, and the presence thereof can be detected using a second labeled antibody which binds to the first anti-T-bet antibody.

In some embodiments, the CD4+ cells from the peripheral blood test sample are contacted with an anti-ICOS detection antibody and/or an anti-T-bet detection antibody and the binding between the antibody (or antibodies) and the CD4+ cells is determined. In some embodiments, the level of total ICOS and/or T-bet expression in CD4+ T cells is determined using a fluorescence activated cell sorter. Fluorescence activated cell sorters can have varying degrees of sophistication, such as multiple color channels, low angle and obtuse light scattering detecting channels, impedance channels, etc. Cells may be selected against dead cells by employing dyes associated with dead cells (e.g., propidium iodide). The FACS apparatus commonly includes a light source, usually a laser, and several detectors for the detection of cell particles or subpopulations of cells in a mixture using light scatter or light emission parameters. The underlying mechanisms of FACS are well known in the art, and essentially involve scanning (e.g., counting, sorting by size or fluorescent label) single particles are they flow in a liquid medium past an excitation light source. Light is scattered and fluorescence is emitted as light from the excitation source strikes the moving particle. Forward scatter (FSC, light scattered in the forward direction, i.e., the same direction as the beam) provides basic morphological information about the particles, such as cell size and morphology. Light that is scattered at 90° to the incident beam is due to refracted or reflected light, and is referred to as side angle scatter (SSC). This parameter measures the granularity and cell surface topology of the particles. Collectively, scatter signals in both the forward and wide angle direction are used to identify subpopulations of cells based on cell size, morphology, and granularity. This information is used to distinguish various cellular populations in a heterogeneous sample.

Exemplary anti-ICOS antibodies for use in the detection aspects of the methods described herein are antibodies that recognize an internal (i.e., intracellular) epitope of ICOS. While ICOS can be expressed on the surface of T cells, it is estimated that a large proportion of total cellular ICOS (e.g., about 80%) is present in intracellular stores. While exemplary therapeutic anti-ICOS antibodies, such as JTX-2011, recognize extracellular epitopes of ICOS, the use of an anti-ICOS detection antibody that specifically binds to an intracellular ICOS epitope allows for the determination of total ICOS expression levels. Examples of antibodies that recognize intracellular ICOS epitopes, and thus which can be used in methods to detect total ICOS, include 2M13 and 2M19 (see WO 2017/070423; also see Table 3, below), and variants thereof. In addition, antibodies that compete with 2M13 and 2M19 for binding to ICOS can be used to detect ICOS according to the methods of the invention.

b. Exemplary Nucleic Acid-Based Detection Methods

In some embodiments, the methods provided herein include measuring an mRNA level. In some embodiments, the methods provided herein comprise measuring an ICOS and/or T-bet mRNA.

Any suitable method of determining mRNA levels may be used. Methods for the evaluation of mRNAs include, for example, hybridization assays using complementary DNA probes (such as in situ hybridization using labeled riboprobes specific for target sequences, Northern blot and related techniques) and various nucleic acid amplification assays (such as RT-PCR using complementary primers specific for target sequences and other amplification type detection methods, such as, for example, branched DNA, SISBA, TMA and the like).

In some embodiments, the mRNA level is determined by quantitative RT-PCR. In some embodiments, the mRNA level is determined by digital PCR. In some embodiments, the mRNA level is determined by RNA-Seq. In some embodiments, the mRNA level is determined by RNase Protection Assay (RPA). In some embodiments, the mRNA level is determined by Northern blot. In some embodiments, the mRNA level is determined by in situ hybridization (ISH). In some embodiments, the mRNA level is determined by a method selected from quantitative RT-PCR, microarray, digital PCR, RNA-Seq, RNase Protection Assay (RPA), Northern blot, and in situ hybridization (ISH).

In some embodiments, for example when quantitative RT-PCR is used, the threshold cycle number is compared between two mRNAs, and the lower threshold indicates a higher level of the respective mRNA. As a non-limiting example, in some embodiments, if levels of ICOS mRNA and at least one reference mRNA are analyzed and the threshold cycle number (Ct) for ICOS is 28 and the Ct for the reference mRNA is 30, then ICOS is at a higher level compared to the reference. In various embodiments, similar comparisons may be carried out for any type of quantitative or semi-quantitative analytical method.

In some embodiments, the level of at least one mRNA is normalized. In some embodiments, the level of at least two mRNAs are normalized and compared to each other. In some embodiments, such normalization may allow comparison of mRNA levels when the levels are not determined simultaneously and/or in the same assay reaction. One skilled in the art can select a suitable basis for normalization, such as at least one reference mRNA or other factor, depending on the assay.

In some embodiments, the at least one reference mRNA comprises a housekeeping gene. In some embodiments, the at least one reference mRNA comprises one or more of RPLPO, PPIA, TUBB, ACTB, YMHAZ, B2M, UBC, TBP, GUSB, HPRT1, or GAPDH.

VI. Examples

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Examination of Total ICOS Expression in CD4+ T Cells of Cancer Patients Receiving JTX-2011 Monotherapy or Combination Therapy of JTX-2011 and Nivolumab Study Design Total ICOS expression in CD4+ T cells from 44 patients with gastric cancer, non-small cell lung cancer (NSCLC), or triple negative breast cancer (TNBC) receiving a JTX-2011 monotherapy (at 0.3 mg/kg q3w) or a combination therapy of JTX-2011 (at 0.1 mg/kg or 0.3 mg/kg q3w) and nivolumab (at 240 mg q3w) was evaluated using multi-color flow cytometry as described below. Of these patients, 4 had a confirmed partial response (cPR), 3 had an unconfirmed partial response (PR), 17 had stable disease (SD), and 20 had progressive disease (PD) as the best overall response (BOR) in response to the therapies.

Assessment of Total ICOS Expression in CD4+ T Cells by Flow Cytometry

Peripheral blood mononuclear cells (PBMCs) were obtained from patient whole blood samples through a density gradient separation using BD Vacutainer CPT Mononuclear Cell Preparation. Isolated PBMC samples were then frozen and stored at −80° C. until use in a flow cytometry application. At the time of analysis, PBMC sample tubes were thawed in a 37° C. water bath for approximately 2 minutes. Each sample was then transferred to a 15 mL conical tube with FACS buffer (1×PBS, 2% FBS, 0.01% sodium azide, 2 mM EDTA), and the cells enumerated. Staining was performed on 1×10$^6$ PBMCs per sample. Following enumeration, PBMCs were centrifuged at 500×g for 3 minutes to obtain a cell pellet. Excess buffer was aspirated and the cell pellet was re-suspended in FACS buffer. The cell pellet re-suspension was divided equally into the wells of a 96-well round bottom plate, and each well was then Fc blocked using 5 μL of Fc block (Human TruStain FcX, BioLegend Cat #422302) per 1×10$^5$ PBMCs for 20 minutes at room temperature. Following blocking, the plate was centrifuged at 500×g for 3 minutes and excess buffer was removed.

Wells designated for the primary staining cocktail to assess total ICOS levels received 100 μL of master staining mix containing anti-human CD3 (clone: UCHT1), anti-human CD4 (clone: OKT4), and JTX-2011 Dylight 650. Wells designated for the isotype staining cocktail received 100 μL of master staining mix containing anti-human CD-3 (clone: UCHT1), anti-human CD4 (clone: OKT4), and anti-RSV Dylight 650. Staining cocktails were incubated at 4° C. for 30 minutes and then were centrifuged at 500×g for 3 minutes, two times with FACS buffer to wash. All wells were then fixed and permeabilized for 30 minutes (eBioscience FOXP3/Transcription Factor Staining Buffer Set ref. #00-5523-00 Life Technologies). Following permeabilization, the plate was centrifuged at 500×g for 3 minutes and excess buffer was removed. Wells designated for the primary staining cocktail received 100 μL of master staining mix diluted in 1× permeabilization buffer (eBioscience FOXP3/Transcription Factor Staining Buffer Set ref. #00-5523-00 Life Technologies) containing anti-T-bet (clone: 4610), streptavidin PE (BioLegend Cat 405204), and biotinylated M13 anti-ICOS detection antibody (Jounce Therapeutics), which recognizes an internal epitope of ICOS (see FIG. 1).

Wells designated for the isotype control staining cocktail received 100 μL of master staining mix prepared in 1× permeabilization buffer (eBioscience FOXP3/Transcription Factor Staining Buffer Set ref. #00-5523-00 Life Technologies) containing Streptavidin PE alone.

Staining cocktails were incubated at 4° C. for 30 minutes. The plate was then centrifuged at 500×g for 3 minutes, two times with 1× permeabilization buffer to wash. The contents of the wells were then re-suspended in 150 μL of FACS buffer. Stained samples were immediately analyzed using a BD FACS Canto flow cytometer, with resulting data analyzed using FlowJo analysis software.

Figure 2:
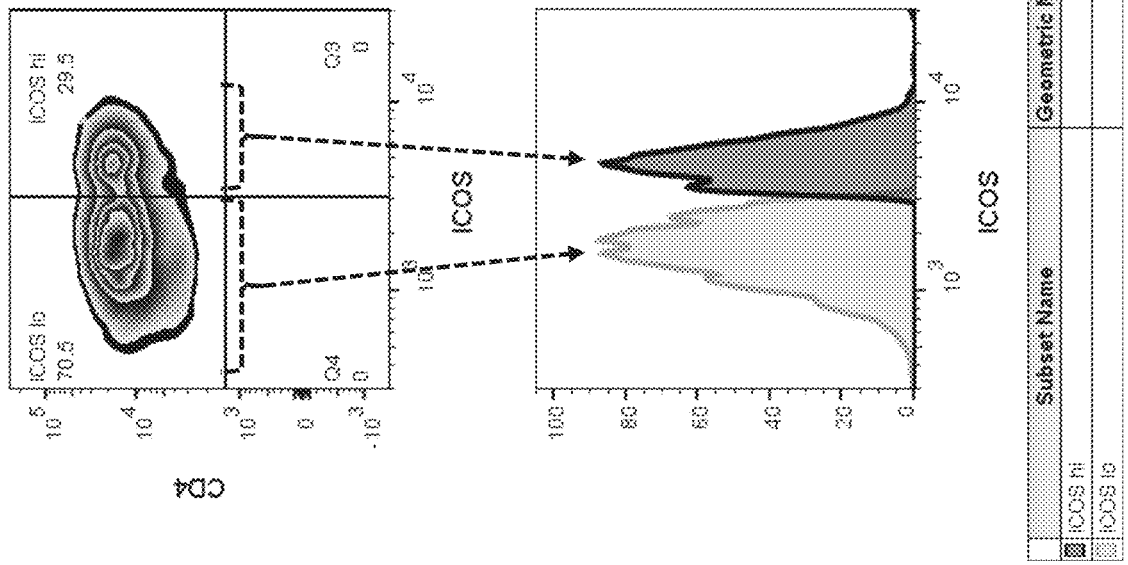
FIG. 2 is a schematic showing an approach to determining whether a sample includes a population of ICOS$^{HIGH}$ CD4+ T cells.

Analysis of a sample to determine whether it includes an ICOS$^{hi}$ population of CD4+ T cells is shown in FIG. 2. Gates are drawn to bisect ICOS$^{lo}$ and ICOS$^{hi}$ populations, and histograms of the ICOS$^{lo}$ and ICOS$^{hi}$ quadrants are overlaid with geometric mean fluorescent intensity calculated.

Results

Figure 3A:
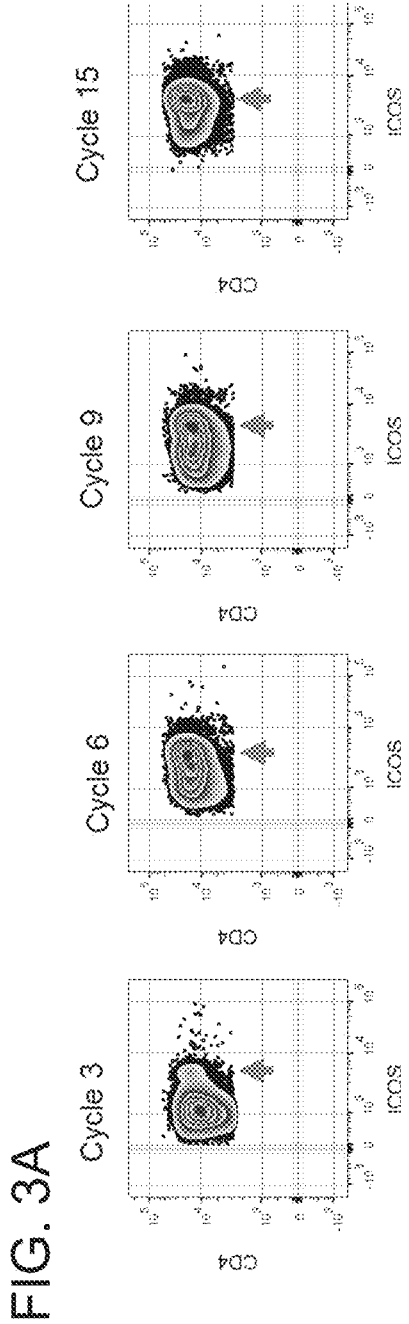
FIG. 3A is a series of contour plots showing ICOS expression in CD4+ T cells in a sample from a gastric cancer patient with a confirmed partial response (cPR) to monotherapy of JTX-2011 at 0.3 mg/kg, q3w over cycles 3-15.
Figure 3B:
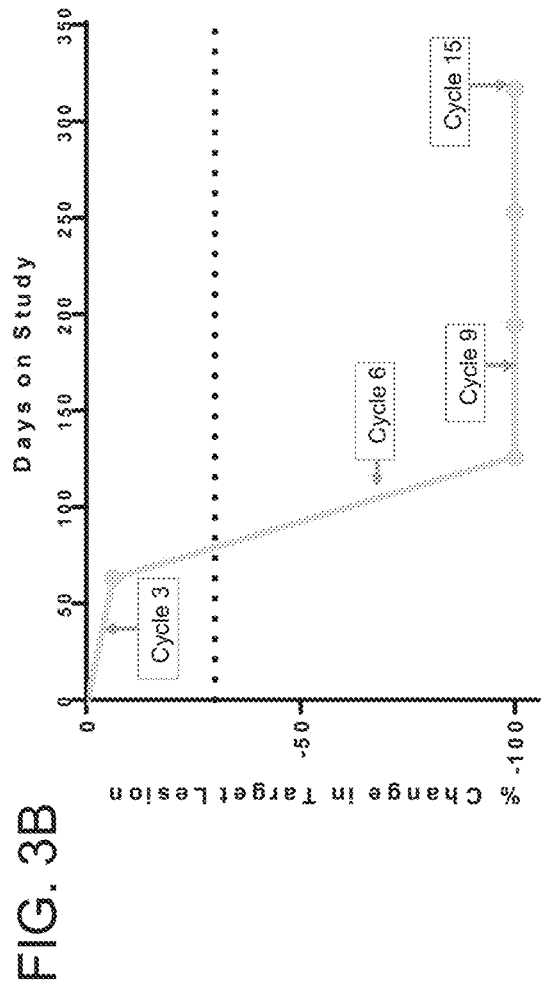
FIG. 3B is a plot showing the percent change in the size of a target lesion over time in a sample from a gastric cancer patient with a confirmed partial response (cPR) to monotherapy of JTX-2011 at 0.3 mg/kg, q3w over cycles 3-15.

The emergence and stabilization of an ICOS$^{hi}$ CD4+ T cell population was observed in a gastric cancer patient with a cPR to JTX-2011 (0.3 mg/kg, q3w) monotherapy. The population was detected as early as following cycle 3, expanded, and was stable following cycle 15 (FIG. 3A). The emergence and stabilization of the ICOS$^{hi}$ CD4+ T population correlated with evidence of clinical activity as demonstrated by a reduction in target lesion size evaluated according to RECIST 1.1 criteria (FIG. 3B).

Figure 4:
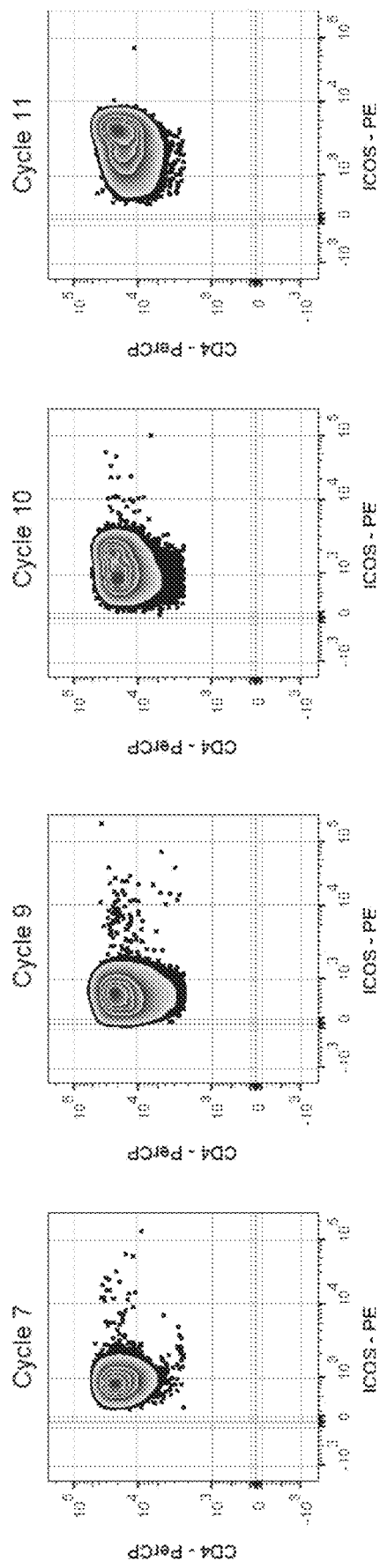
FIG. 4 is a series of contour plots showing ICOS expression in CD4+ T cells in a sample from a gastric cancer patient with a confirmed partial response to combination therapy of JTX-2011 at 0.1 mg/kg and nivolumab at 240 mg, q3w over cycles 7-11.

The emergence of a population of CD4+ T cells with elevated ICOS expression levels (ICOS$^{hi}$) was also observed in a sample from a gastric cancer patient with a cPR to a combination therapy of JTX-2011 (0.1 mg/kg, q3w) and nivolumab (240 mg, q3w). This population was detected following cycle 7, and there was a subsequent stabilization of the population through at least cycle 11 (FIG. 4).

Figure 5:
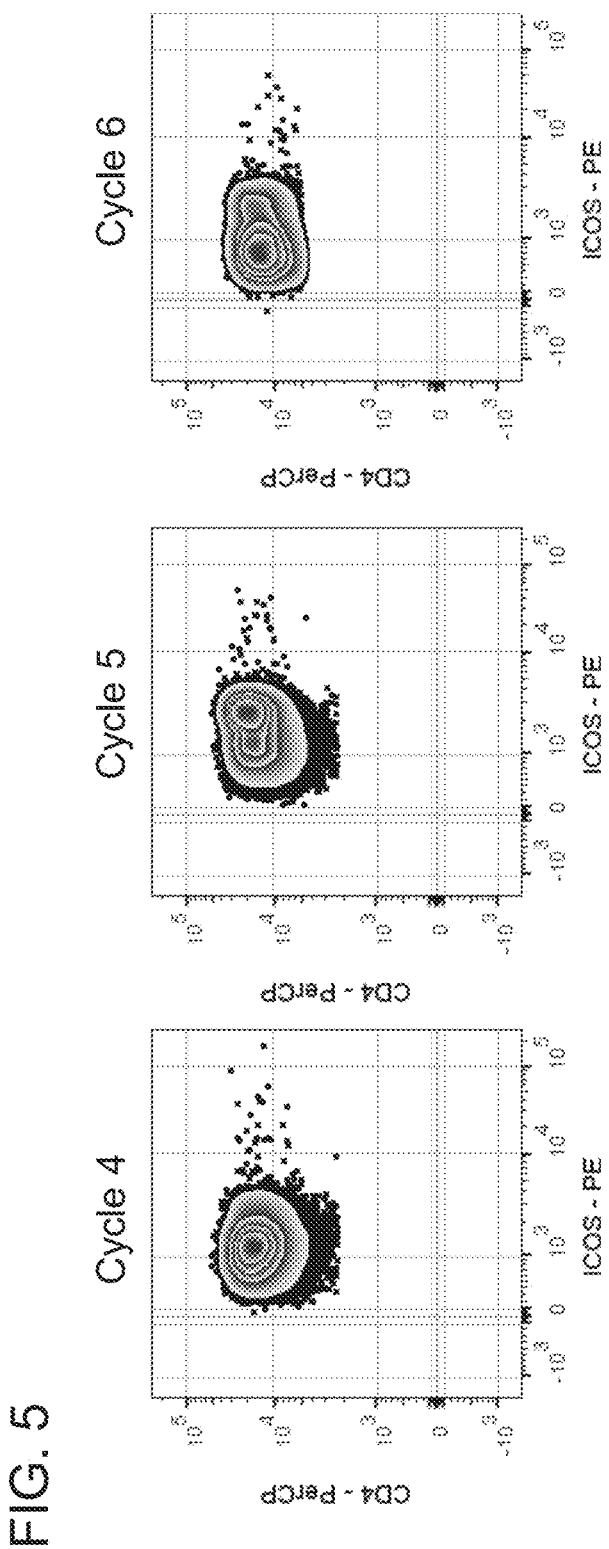
FIG. 5 is a series of contour plots showing ICOS expression in CD4+ T cells in a sample from a gastric cancer patient with stable disease receiving combination therapy of JTX-2011 at 0.3 mg/kg and nivolumab at 240 mg, q3w over cycles 4-6.

Transient populations of ICOS$^{hi}$ CD4+ T cells were observed in a sample from a gastric cancer patient who presented with stable disease in response to combination therapy of JTX-2011 (0.3 mg/kg, q3w) and nivolumab (240 mg, q3w) (FIG. 5). Populations of ICOS$^{hi}$ CD4+ T cells were observed following cycle 4 and expanded following cycle 5, but were diminished following cycle 6, prior to disease progression.

Figure 6:
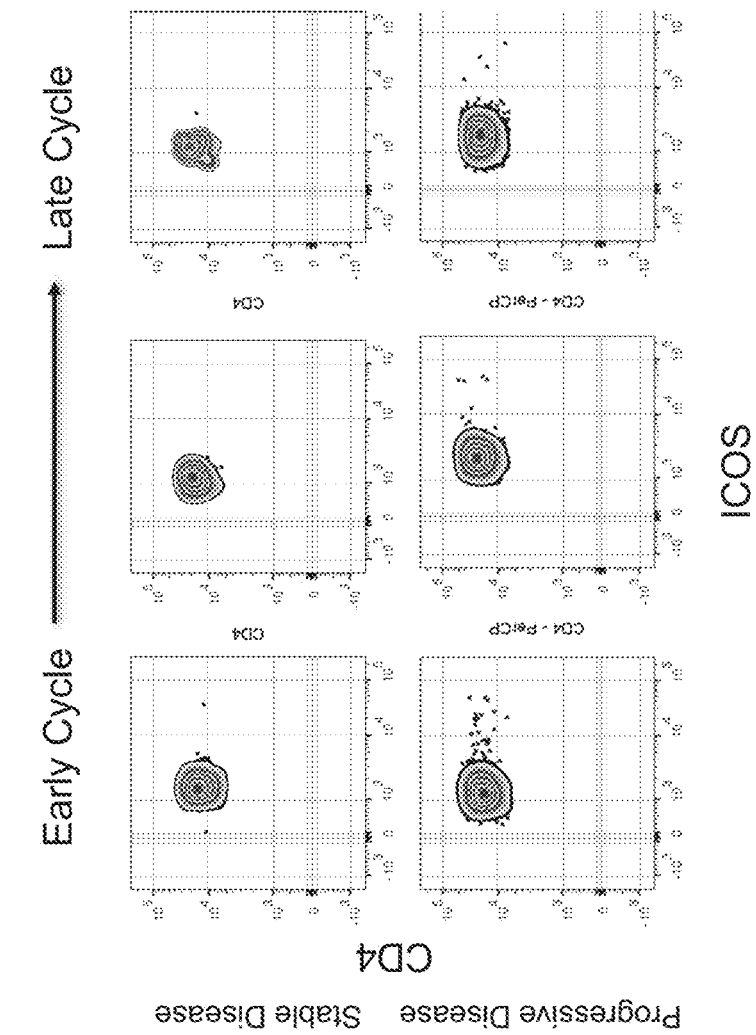
FIG. 6 is a series of contour plots showing ICOS expression in CD4+ T cells in samples from triple negative breast cancer (TNBC) patients with stable disease or progressive disease receiving a combination therapy of JTX-2011 at 0.3 mg/kg and nivolumab at 240 mg, q3w.

Populations of ICOS$^{hi}$ CD4+ T cells were not observed in TNBC patients who exhibited SD or PD in response to combination therapy of JTX-2011 (0.3 mg/kg, q3w) and nivolumab (240 mg, q3w) (FIG. 6).

Conclusion

Figure 7B:
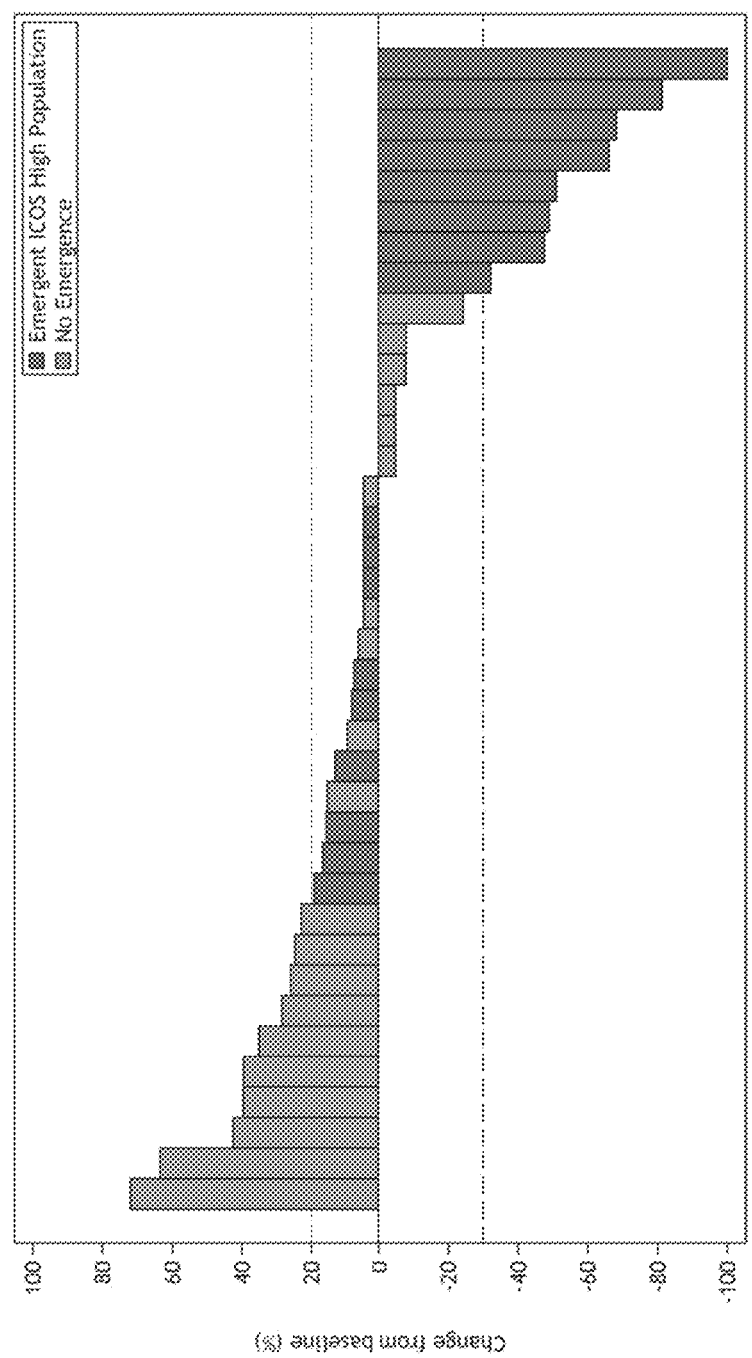
FIG. 7B is a waterfall plot comparing the percent change from baseline in target lesion with the emergence of an ICOS$^{hi}$ CD4+ T cell population in cancer patients receiving a JTX-2011 monotherapy or a combination therapy of JTX-2011 and nivolumab.
Figure 7C:
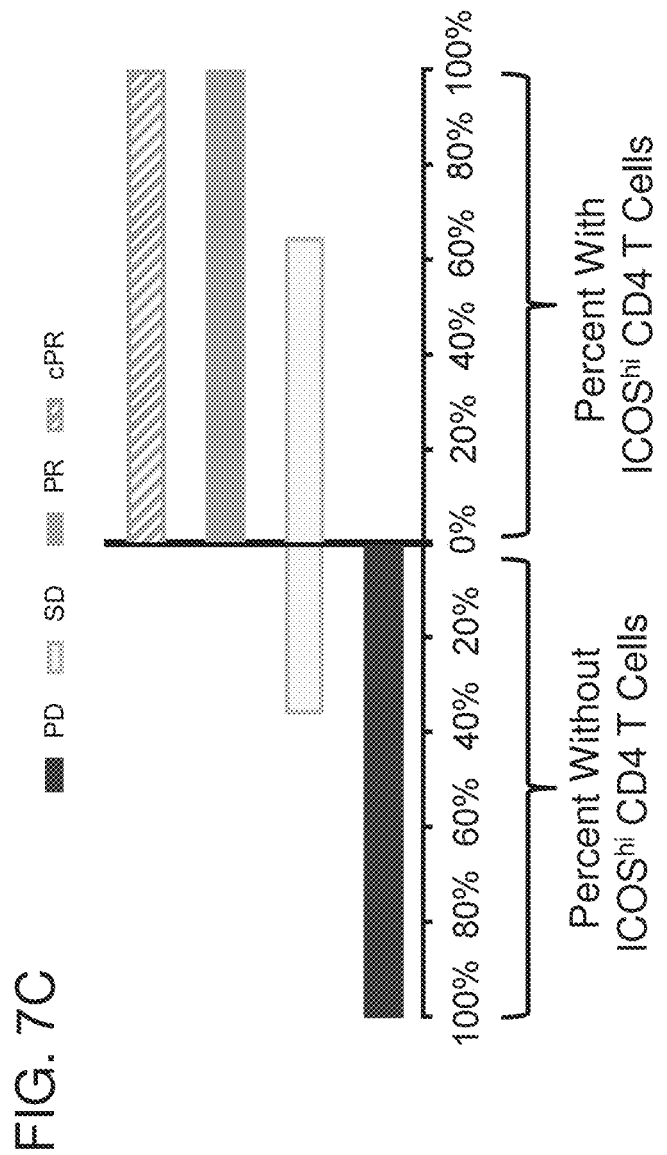
FIG. 7C is a graph showing the percent of cancer patients having progressive disease (PD), stable disease (SD), unconfirmed positive response (PR), and confirmed positive response (cPR) to JTX-2011 monotherapy or a combination therapy of JTX-2011 and nivolumab, with and without CD4+ T cells having increased ICOS expression.

An ICOS$^{hi}$ CD4+ T cell population was observed in all patients with cPR and PR, and in 11 out of 17 patients with stable disease as BOR in response to therapy. This population was not observed in the remaining 6 patients with stable disease, nor in the 20 patients with progressive disease in response to therapy (FIGS. 7A-7C). The emergence of this population correlated with evidence of biological activity corresponding to percent change from baseline of the target lesion size (FIGS. 7A-7C).

Example 2: Examination of Total ICOS Expression in CD4+ T Cells in Sa1/N Tumor-Bearing Mice Receiving JTX-1011-mG2a Study Design Mice bearing Sa1/N fibrosarcomas (Ostrand-Rosenberg, 2001, Curr. Protoc. Immunol., Chapter 20) received a once weekly dose of 0.25 mg/kg JTX-1011-mG2a. Whole blood samples were collected 1 hour and 48 hours following administration of the second dose of the antibody, and were analyzed for total ICOS expression in CD4+ T cell as described below.

Assessment of Total ICOS Expression in CD4+ T Cells by Flow Cytometry

Peripheral blood samples were collected via tail vein into BD NaEDTA Microtainer tubes and were stained fresh for flow analysis. 100 μL of whole blood was allocated to an appropriate well in a 96-well round bottom plate, and each well was then Fc blocked for 15 minutes at 4° C. Fc blocking was performed using TruStain fcX (anti-mouse CD16/32) antibody (BioLegend, Cat #101320).

Wells designated for the primary staining cocktail to assess total ICOS levels received 100 μL of master staining mix containing anti-CD3 (clone 145-2C11), anti-CD4 (clone GK1.5), anti-CD8 (clone 53-6.7), anti-ICOS (JTX-2011 DyLight650, Jounce Therapeutics). Wells designated for the isotype staining cocktail received 100 μL of master staining mix containing species and fluorochrome-specific isotype controls. Staining cocktails were incubated at 4° C. for 30 minutes, and then centrifuged at 500×g for 3 minutes, two times with FACS buffer to wash. All wells were then fixed and permeabilized for 30 minutes (eBioscience FOXP3/Transcription Factor Staining Buffer Set ref. #00-5523-00 Life Technologies). Following permeabilization, the plate was centrifuged at 500×g, for 3 min, and excess buffer was removed. Wells designated for primary staining cocktail received 100 μL of master staining mix prepared in 1× permeabilization buffer (eBioscience FOXP3/Transcription Factor Staining Buffer Set ref.#00-5523-00 Life Technologies) containing anti-FoxP3 (clone FJK-16s).

Wells designated for the isotype control staining cocktail received 100 μL of master staining mix prepared in 1× permeabilization buffer (eBioscience FOXP3/Transcription Factor Staining Buffer Set ref.#00-5523-00 Life Technologies) containing a rat IgG2a, kappa isotype control antibody.

Staining cocktails were incubated at 4° C. for 30 minutes. The plate was then centrifuged at 500×g for 3 minutes, two times with 1× permeabilization buffer to wash. Wells were then re-suspended in 150 μL of FACS buffer. Stained samples were immediately analyzed on a BD FACS Canto flow cytometer, with resulting data analyzed using FlowJo analysis software.

Results and Conclusion

An increase in ICOS staining was observed at 48 hours post-dose of the second cycle of JTX-1011-mG2a relative to 1 hour post-dose (FIG. 8A). This increase in staining corresponded to a rapid emergence of a distinct ICOS$^{hi}$ CD4+ T cell population at 48 hours post administration of JTX-1011-mG2a (FIG. 8B).

Example 3: Examination of Total ICOS and T-Bet Expression in CD4+ T Cells of Cancer Patients Receiving JTX-2011 Monotherapy or Combination Therapy of JTX-2011 and Nivolumab Study Design Total ICOS and T-bet expression in CD4+ T cells from patients with gastric cancer, triple negative breast cancer (TNBC), or endometrial cancer receiving a JTX-2011 monotherapy (at 0.3 mg/kg q3w) or a combination therapy of JTX-2011 (at 0.1 mg/kg or 0.3 mg/kg, q3w) and nivolumab (at 240 mg q3w) was evaluated using multi-color flow cytometry as described below.

Assessment of Total ICOS and T-bet Expression in CD4+ T Cells by Flow Cytometry

Peripheral blood mononuclear cells (PBMCs) were obtained from patient whole blood samples through a density gradient separation using BD Vacutainer CPT Mononuclear Cell Preparation. At the time of analysis, PBMC sample tubes were thawed in a 37° C. water bath for approximately 2 minutes.

Each sample was then transferred to a 15 mL conical tube with FACS buffer (1×PBS, 2% FBS, 0.01% sodium azide, 2 mM EDTA), and the cells enumerated. Staining was performed on 1×10$^6$ PBMCs per sample. Following enumeration, PBMCs were centrifuged at 500×g for 3 minutes to obtain a cell pellet. Excess buffer was aspirated and the cell pellet was re-suspended in FACS buffer. The cell pellet re-suspension was divided equally into the wells of a 96-well round bottom plate, and each well was then Fc blocked using 5 μL of Fc block (Human TruStain FcX, BioLegend Cat #422302) per 1×10$^5$ PBMCs for 20 minutes at room temperature. Following blocking, the plate was centrifuged at 500×g for 3 minutes and excess buffer was removed.

Wells designated for the primary staining cocktail to assess total ICOS levels received 100 μL of master staining mix containing anti-human CD3 (clone: UCHT1), anti-human CD4 (clone: OKT4), and JTX-2011 Dylight 650. Wells designated for the isotype staining cocktail received 100 μL of master staining mix containing anti-human CD-3 (clone: UCHT1), anti-human CD4 (clone: OKT4), and anti-RSV Dylight 650. Staining cocktails were incubated at 4° C. for 30 minutes and were then centrifuged at 500×g for 3 minutes, two times, with FACS buffer to wash. All wells were then fixed and permeabilized for 30 minutes (eBioscience FOXP3/Transcription Factor Staining Buffer Set ref. #00-5523-00 Life Technologies). Following permeabilization, the plate was centrifuged at 500×g for 3 minutes and excess buffer was removed. Wells designated for the primary staining cocktail received 100 μL of master staining mix diluted in 1× permeabilization buffer (eBioscience FOXP3/Transcription Factor Staining Buffer Set ref. #00-5523-00 Life Technologies) containing anti-T-bet (clone: 4610), streptavidin PE, and biotinylated M13 anti-ICOS detection antibody, which recognizes an internal epitope of ICOS (see FIG. 1).

Wells designated for the isotype control staining cocktail received 100 μL of master staining mix prepared in 1× permeabilization buffer (eBioscience FOXP3/Transcription Factor Staining Buffer Set ref. #00-5523-00 Life Technologies) containing Streptavidin PE alone.

Staining cocktails were incubated at 4° C. for 30 minutes. The plate was then centrifuged at 500×g for 3 minutes, two times, with 1× permeabilization buffer to wash. The contents of the wells were then re-suspended in 150 µL of FACS buffer. Stained samples were immediately analyzed using a BD FACS Canto flow cytometer, with resulting data analyzed using FlowJo analysis software.

Results and Conclusion

Figure 9:
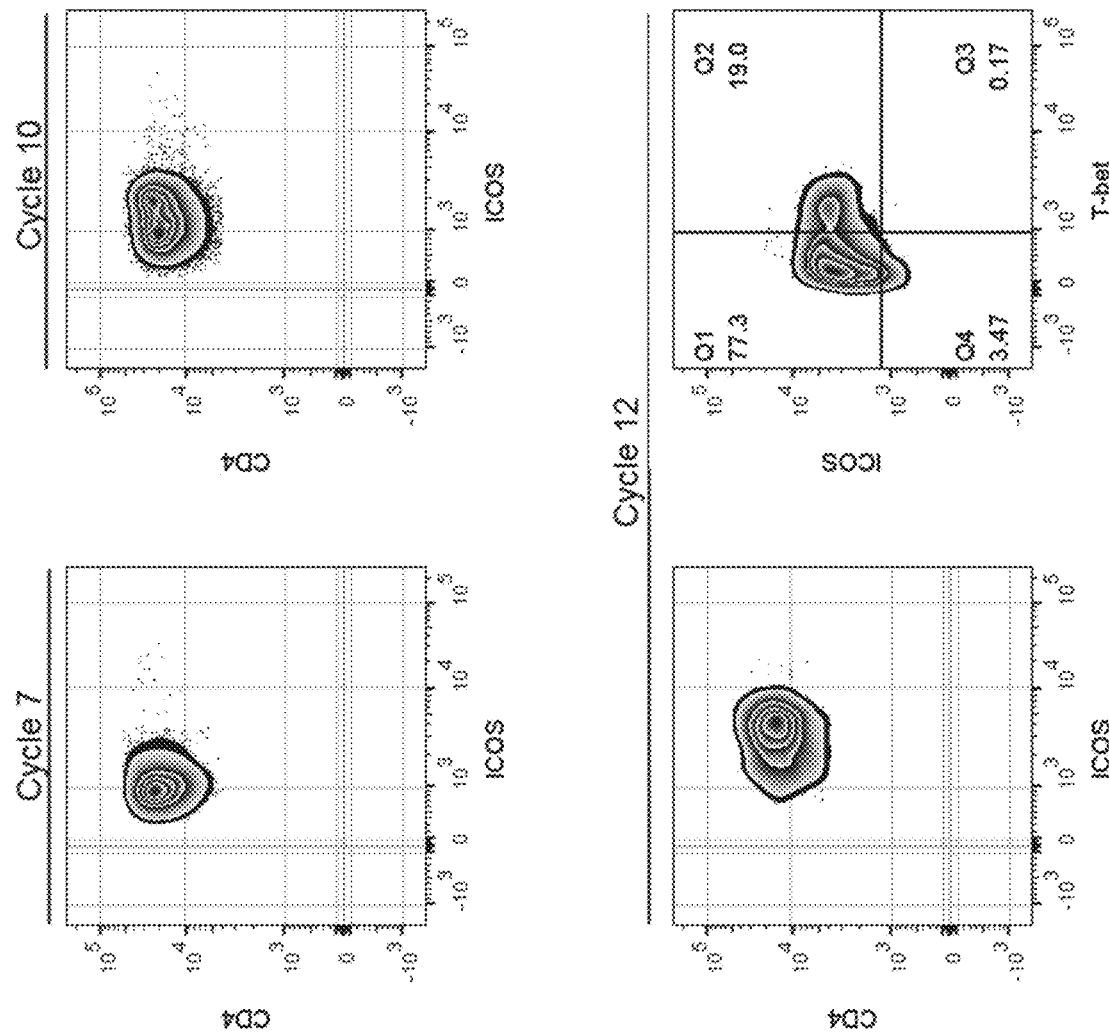
FIG. 9 is a series of contour plots showing ICOS expression in CD4+ T cells in a sample from a gastric cancer patient with a confirmed partial response (cPR) to combination therapy with JTX-2011 at 0.1 mg/kg and nivolumab at 240 mg, q3w over cycles 7-12. At cycle 12, T-bet expression was assessed on ICOS+ CD4+ T cells.

The emergence and stabilization of an $ICOS^{hi}$ CD4+ T cell population was observed in a PBMC sample from a gastric cancer patient with a cPR to a combination therapy of JTX-2011 (0.1 mg/kg, q3w) and nivolumab (240 mg, q3w). This population was detected as early as cycle 10, and was further identified to contain a sub-population of $ICOS^{hi}$ CD4+ T cells with elevated T-bet levels ($T\text{-bet}^{hi}$) (FIG. 9).

Figure 10:
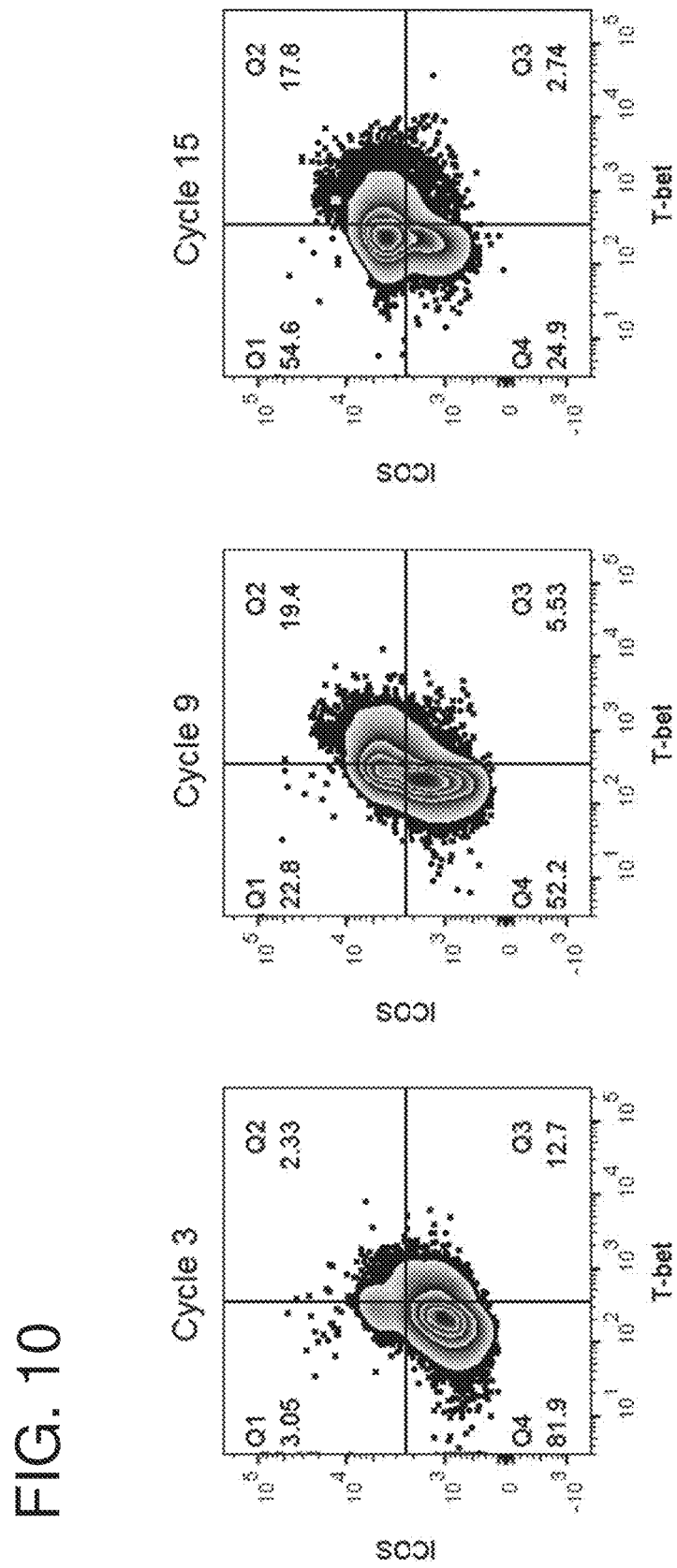
FIG. 10 is a series of contour plots showing ICOS and T-bet expression in CD4+ T cells in a sample from a gastric cancer patient with a confirmed partial response (cPR) to monotherapy with JTX-2011 at 0.3 mg/kg, q3w over cycles 3-15.

The emergence of a population of $ICOS^{hi}/T\text{-bet}^{hi}$ CD4+ T cells was also observed in a sample from a gastric cancer patient with a cPR to a JTX-2011 (0.3 mg/kg, q3w) monotherapy. This population was detected following cycle 3, and there was a subsequent stabilization of the population through at least cycle 15 (FIG. 10).

Figure 11:
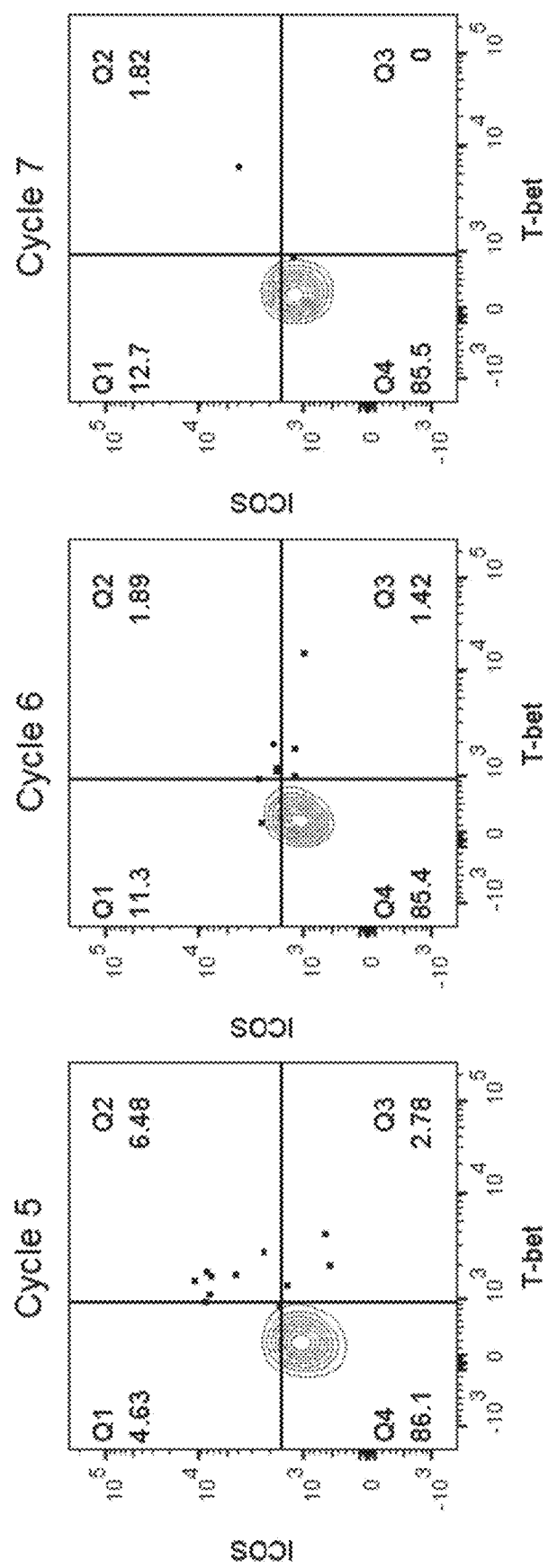
FIG. 11 is a series of contour plots showing ICOS and T-bet expression in CD4+ T cells in a sample from a TNBC patient with stable disease treated with combination therapy of JTX-2011 at 0.3 mg/kg and 240 mg nivolumab, q3w over cycles 5-7.
Figure 12:
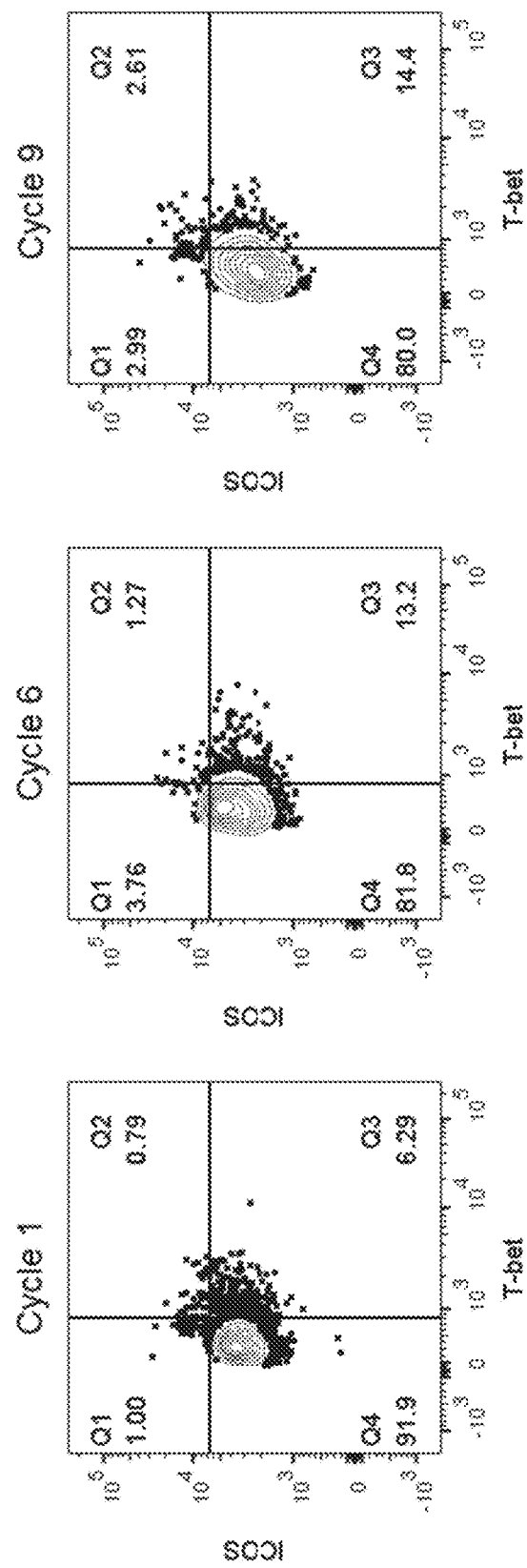
FIG. 12 is a series of contour plots showing ICOS and T-bet expression in CD4+ T cells in a sample from a TNBC patient with stable disease treated with combination therapy of JTX-2011 at 0.3 mg/kg and 240 mg nivolumab, q3w over cycles 1-9.

Populations of $ICOS^{hi}/T\text{-bet}^{hi}$ CD4+ T cells were not observed in TNBC and endometrial cancer patients who exhibited SD in response to combination therapy of JTX-2011 (0.3 mg/kg, q3w) and nivolumab (240 mg, q3w) (FIGS. 11 and 12).

Example 4: Expansion of $ICOS^{hi}$ CD4+ T Cell Populations 4.1

Healthy donor PBMCs were distributed to the wells of a 48-well plate at a density of approximately $3 \times 10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by OKT-3+IL-2 to induce ICOS expression among CD4+ T cells. All supplements were delivered in soluble format.

Cells were incubated for 3 days at 37° C., then transferred to new wells containing fresh media and all supplements used for initial stimulation. Media was further supplemented by Nivolumab (anti-PD-1) to maintain ICOS expression and prevent exhaustion among CD4+ T cells. All supplements were delivered in soluble format.

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.2

Healthy donor PBMCs were distributed to the wells of a 48-well plate at a density of approximately $3 \times 10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by OKT-3+IL-2+ICOS-L to induce ICOS expression among CD4+ T cells. All supplements were delivered in soluble format, with the exception of ICOS-L which was previously coated onto the culture plate (plate-bound format).

Cells were incubated for 3 days at 37° C., then transferred to new wells containing fresh media and all supplements used for initial stimulation. Media was further supplemented by Nivolumab (anti-PD-1) to maintain ICOS expression and prevent exhaustion among CD4+ T cells. All supplements were delivered in soluble format, with the exception of ICOS-L which was previously coated onto the culture plate (plate-bound format).

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.3

Healthy donor PBMCs were distributed to the wells of a 48-well plate at a density of approximately $3 \times 10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by IL-2+IL-12+anti-IL-4+Stemcell ImmunoCult human CD3/CD28 T cell activator (Cat #10971) to induce ICOS expression among CD4+ T cells. All supplements were delivered in soluble format.

Cells were incubated for 3 days at 37° C., then transferred to new wells containing fresh media and all supplements used for initial stimulation. Media was further supplemented by Nivolumab (anti-PD-1) to maintain ICOS expression and prevent exhaustion among CD4+ T cells. All supplements were delivered in soluble format.

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.4

Healthy donor PBMCs were distributed to the wells of a 48-well plate at a density of approximately $3 \times 10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by IL-2+IL-12+anti-IL-4+Stemcell ImmunoCult human CD3/CD28 T cell activator (Cat #10971)+ICOS-L to induce ICOS expression among CD4+ T cells. All supplements were delivered in soluble format, with the exception of ICOS-L which was previously coated onto the culture plate (plate-bound format).

Cells were incubated for 3 days at 37° C., then transferred to new wells containing fresh media and all supplements used for initial stimulation. Media was further supplemented by Nivolumab (anti-PD-1) to maintain ICOS expression and prevent exhaustion among CD4+ T cells. All supplements were delivered in soluble format, with the exception of ICOS-L which was previously coated onto the culture plate (plate-bound format).

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.5

Healthy donor PBMCs were distributed to the wells of a 48-well plate at a density of approximately $3 \times 10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by OKT-3+IL-2 to induce ICOS expression among CD4+ T cells. All supplements were delivered in soluble format.

Cells were incubated for 3 days at 37° C., then transferred to new wells containing fresh media and all supplements used for initial stimulation. Media was further supplemented by Ipilimumab (anti-CTLA-4) to maintain ICOS expression and prevent exhaustion among CD4+ T cells. All supplements were delivered in soluble format.

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.6

Healthy donor PBMCs were distributed to the wells of a 48-well plate at a density of approximately $3\times10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by OKT-3+IL-2+ICOS-L to induce ICOS expression among CD4+ T cells. All supplements were delivered in soluble format, with the exception of ICOS-L which was previously coated onto the culture plate (plate-bound format).

Cells were incubated for 3 days at 37° C., then transferred to new wells containing fresh media and all supplements used for initial stimulation. Media was further supplemented by Ipilimumab (anti-CTLA-4) to maintain ICOS expression and prevent exhaustion among CD4+ T cells. All supplements were delivered in soluble format, with the exception of ICOS-L which was previously coated onto the culture plate (plate-bound format).

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.7

Healthy donor PBMCs were distributed to the wells of a 48-well plate at a density of approximately $3\times10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by IL-2+IL-12+anti-IL-4+Stemcell ImmunoCult human CD3/CD28 T cell activator (Cat #10971) to induce ICOS expression among CD4+ T cells. All supplements were delivered in soluble format.

Cells were incubated for 3 days at 37° C., then transferred to new wells containing fresh media and all supplements used for initial stimulation. Media was further supplemented by Ipilimumab (anti-CTLA-4) to maintain ICOS expression and prevent exhaustion among CD4+ T cells. All supplements were delivered in soluble format.

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.8

Healthy donor PBMCs were distributed to the wells of a 48-well plate at a density of approximately $3\times10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by IL-2+IL-12+anti-IL-4+Stemcell ImmunoCult human CD3/CD28 T cell activator (Cat #10971)+ICOS-L to induce ICOS expression among CD4+ T cells. All supplements were delivered in soluble format, with the exception of ICOS-L which was previously coated onto the culture plate (plate-bound format).

Cells were incubated for 3 days at 37° C., then transferred to new wells containing fresh media and all supplements used for initial stimulation. Media was further supplemented by Ipilimumab (anti-CTLA-4) to maintain ICOS expression and prevent exhaustion among CD4+ T cells. All supplements were delivered in soluble format, with the exception of ICOS-L which was previously coated onto the culture plate (plate-bound format).

Cells were incubated for another 4 days at 37° C., then transferred to new wells containing fresh media and all supplements used for initial stimulation and ICOS maintenance. Cells were then incubated for another 3 days at 37° C., then stained and fixed. At the end of 10 total days of incubation, cells had expanded by a minimum of 24-fold.

4.9

Healthy donor PBMCs were distributed to the wells of a 48-well plate at a density of approximately $3\times10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by OKT-3+IL-2 to induce ICOS expression among CD4+ T cells. All supplements were delivered in soluble format.

Cells were incubated for 3 days at 37° C., then transferred to new wells containing fresh media and all supplements used for initial stimulation, except OKT-3, to maintain ICOS expression and prevent exhaustion among CD4+ T cells. All supplements were delivered in soluble format.

Cells were incubated for another 4 days at 37° C., then transferred to new wells containing fresh media and all supplements used for initial stimulation and ICOS maintenance, including OKT-3. Cells were then incubated for another 3 days at 37° C., then stained and fixed. At the end of 10 total days of incubation, cells had expanded by a minimum of 24-fold.

4.10

Healthy donor PBMCs were distributed to the wells of a 48-well plate at a density of approximately $3\times10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by OKT-3+IL-2+ICOS-L to induce ICOS expression among CD4+ T cells. All supplements were delivered in soluble format, with the exception of ICOS-L which was previously coated onto the culture plate (plate-bound format).

Cells were incubated for 3 days at 37° C., then transferred to new wells containing fresh media and all supplements used for initial stimulation, except OKT-3, to maintain ICOS expression and prevent exhaustion among CD4+ T cells. All supplements were delivered in soluble format, with the exception of ICOS-L which was previously coated onto the culture plate (plate-bound format).

Cells were incubated for another 4 days at 37° C., then transferred to new wells containing fresh media and all supplements used for initial stimulation and ICOS maintenance, including OKT-3. Cells were then incubated for another 3 days at 37° C., then stained and fixed. At the end of 10 total days of incubation, cells had expanded by a minimum of 24-fold.

4.11

Healthy donor PBMCs were distributed to the wells of a 48-well plate at a density of approximately $3 \times 10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by IL-2+IL-12+anti-IL-4+Stemcell ImmunoCult human CD3/CD28 T cell activator (Cat #10971) to induce ICOS expression among CD4+ T cells. All supplements were delivered in soluble format.

Cells were incubated for 3 days at 37° C., then transferred to new wells containing fresh media and all supplements used for initial stimulation, except Stemcell ImmunoCult human CD3/CD28 T cell activator, to maintain ICOS expression and prevent exhaustion among CD4+ T cells. All supplements were delivered in soluble format.

Cells were incubated for another 4 days at 37° C., then transferred to new wells containing fresh media and all supplements used for initial stimulation and ICOS maintenance, including Stemcell ImmunoCult human CD3/CD28 T cell activator. Cells were then incubated for another 3 days at 37° C., then stained and fixed. At the end of 10 total days of incubation, cells had expanded by a minimum of 24-fold.

4.12

Healthy donor PBMCs were distributed to the wells of a 48-well plate at a density of approximately $3 \times 10^5$ cells per well in 500 uL AIM-V medium (Thermo A3830801) supplemented with 5% human AB serum (Sigma H4522) and 1% antibiotic antimycotic solution (Sigma A5955).

Culture media was further supplemented by IL-2+IL-12+anti-IL-4+Stemcell ImmunoCult human CD3/CD28 T cell activator (Cat #10971)+ICOS-L to induce ICOS expression among CD4+ T cells. All supplements were delivered in soluble format, with the exception of ICOS-L which was previously coated onto the culture plate (plate-bound format).

Cells were incubated for 3 days at 37° C., then transferred to new wells containing fresh media and all supplements used for initial stimulation, except Stemcell ImmunoCult human CD3/CD28 T cell activator, to maintain ICOS expression and prevent exhaustion among CD4+ T cells. All supplements were delivered in soluble format, with the exception of ICOS-L which was previously coated onto the culture plate (plate-bound format).

Cells were incubated for another 4 days at 37° C., then transferred to new wells containing fresh media and all supplements used for initial stimulation and ICOS maintenance, including Stemcell ImmunoCult human CD3/CD28 T cell activator. Cells were then incubated for another 3 days at 37° C., then stained and fixed. At the end of 10 total days of incubation, cells had expanded by a minimum of 24-fold.

Example 5: Evaluation of the Cytokine Response in Antigen-Specific ICOS$^{hi}$ and ICOS$^{lo}$ CD4+ T Cells Study Design PBMCs from healthy donors were stimulated to induce an ICOS$^{hi}$ CD4+ T cell population using tetanus toxoid as a model recall antigen. Following 24 hours of stimulation with antigen, cells were washed to remove stimulus and to rest the CD4+ T cells. Following washing, soluble JTX-2011 was added and intracellular cytokine production was assessed by flow cytometry following a 6 hour incubation in the presence of brefeldin A.

Results and Conclusion

Figure 13:
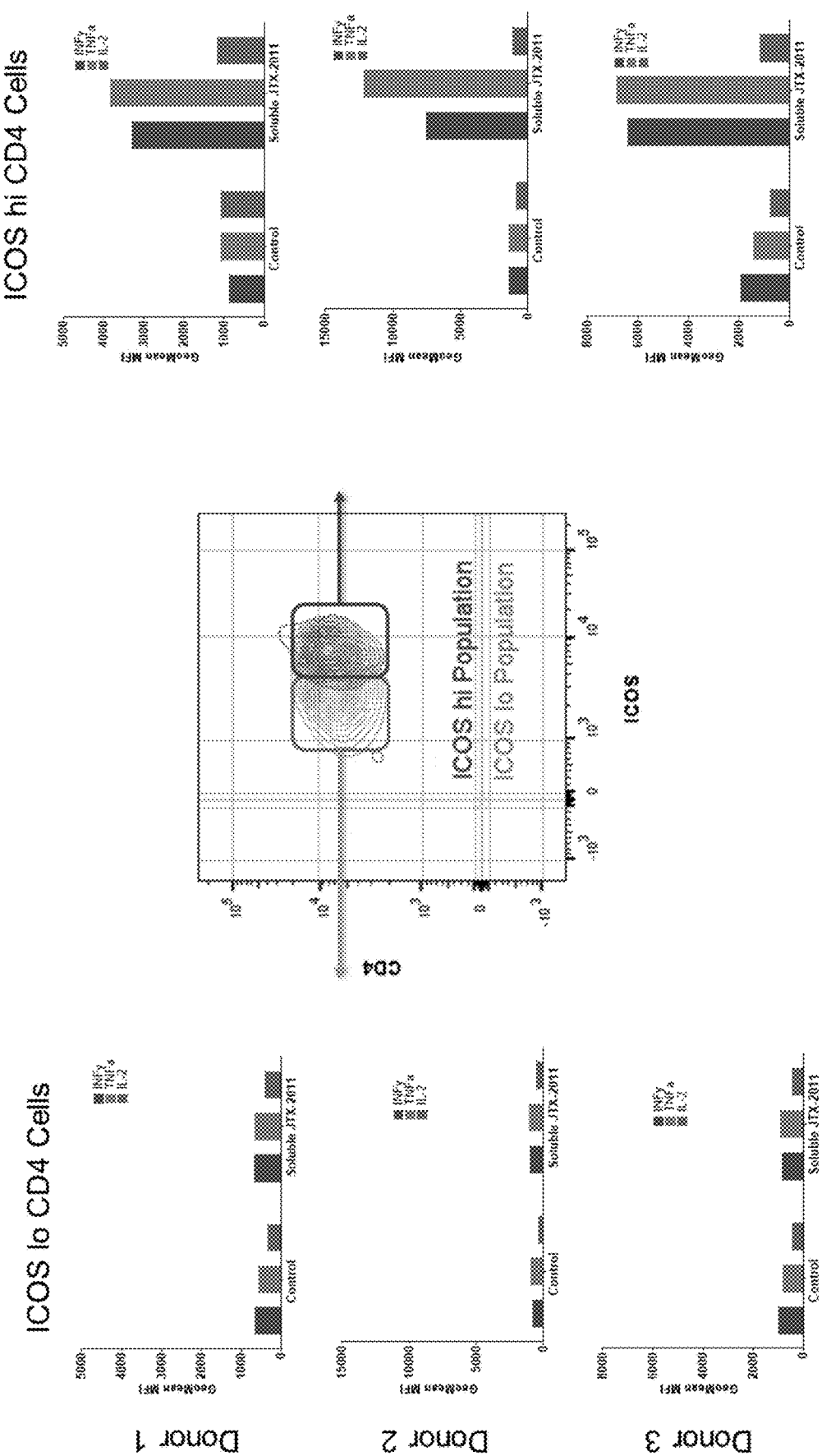
FIG. 13 is a series of graphs showing levels of IFNγ, TNFα, and IL-2 in ICOS$^{lo}$ and ICOS$^{hi}$ CD4+ T cells following stimulation with tetanus toxoid. A representative contour plot highlighting the two cell populations is shown in the inset. The first bar of each set of three is IFNγ, the second bar of each set of three is TNF-a, and the third bar of each set of three is IL-2.

Ex vivo stimulation by soluble JTX-2011 was active only if ICOS$^{hi}$ CD4+ T cells were already present. JTX-2011 induced potent polyfunctional cytokine responses characterized by a 4-fold average increase in both IFNγ and TNFα in antigen-specific ICOS$^{hi}$, but not in ICOS$^{lo}$ CD4+ T cells (FIG. 13).

Figure 14A:
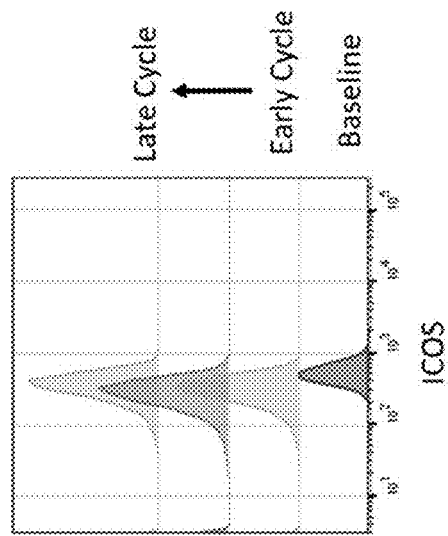
FIG. 14A is a table showing a summary of samples examined for ICOS expression by flow cytometry profiling.

Example 6: Evaluation of the Effect of PD-1 Inhibition on the Emergence of ICOS$^{hi}$ CD4+ T Cells Study Design Samples from subjects receiving standard of care PD-1 inhibitor treatment were obtained from a commercial biorepository. In total, PBMCs from 77 subjects, primarily those with lung cancer or melanoma, were assessed for the emergence of a population of CD4+ T cells by flow cytometry profiling (FIG. 14A).

Results and Conclusion

Figure 14B:
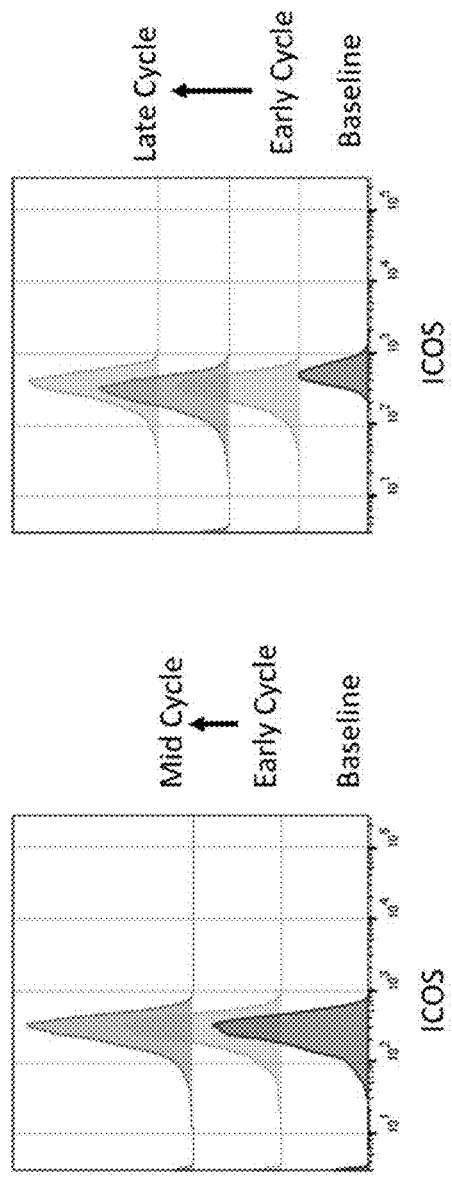
FIG. 14B is a pair of overlaid histograms showing ICOS levels of CD4+ T cells in a NSCLC patient who responded to nivolumab (left panel) and in a NSCLC patient who responded to pembrolizumab (right panel) at various time points. Histograms are arranged in chronological order, starting with baseline profiles for each responder.

Longitudinal flow profiles of a NSCLC subject who responded to nivolumab and a NSCLC subject who responded to pembrolizumab showed no induction of ICOS$^{hi}$ CD4+ T cells (FIG. 14B). Accordingly, the emergence of a population of ICOS$^{hi}$ CD4+ T cells is correlated with JTX-2011 activity, rather than with PD-1 inhibition.

Example 7: Transcriptional and Phenotypic Profiling of ICOS$^{hi}$ and ICOS$^{lo}$ CD4+ T Cells Study Design Transcriptional analysis of purified CD4+ T cells from subjects with treatment-emergent ICOS$^{hi}$ cells vs CD4+ T cells from reference cancer patients not displaying the cell population was performed using a Nanostring human immunology panel. In addition, the immunophenotype of peripheral blood T cells was assessed by flow cytometry at various time points pre- and post-treatment with JTX-2011 alone, or in combination with nivolumab.

Results and Conclusion

Figure 15B:
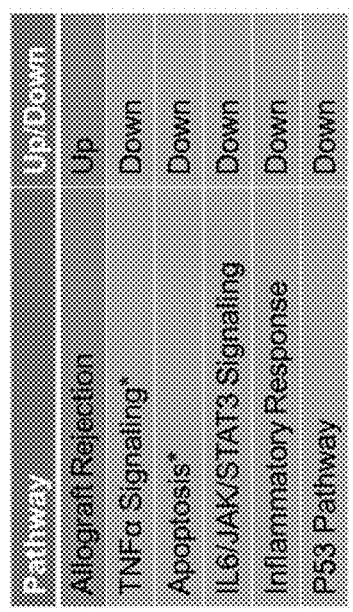
FIG. 15B is a table summarizing major effector pathway modulation in ICOS$^{hi}$ versus ICOS$^{lo}$ CD4+ T cell populations. Pathways with overall FDR corrected q-values below 0.5 are shown.
Figure 15A:
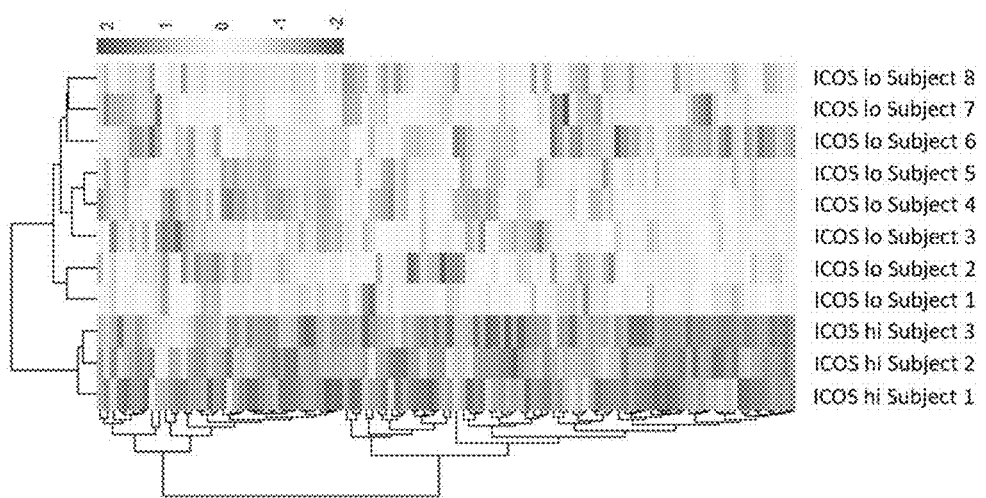
FIG. 15A is a gene expression heat map showing genes that are significantly differentially expressed (FDR adjusted p value<0.05) and define key components of transcriptional differences across ICOS$^{hi}$ and ICOS$^{lo}$ CD4+ T cells.
Figure 15C:
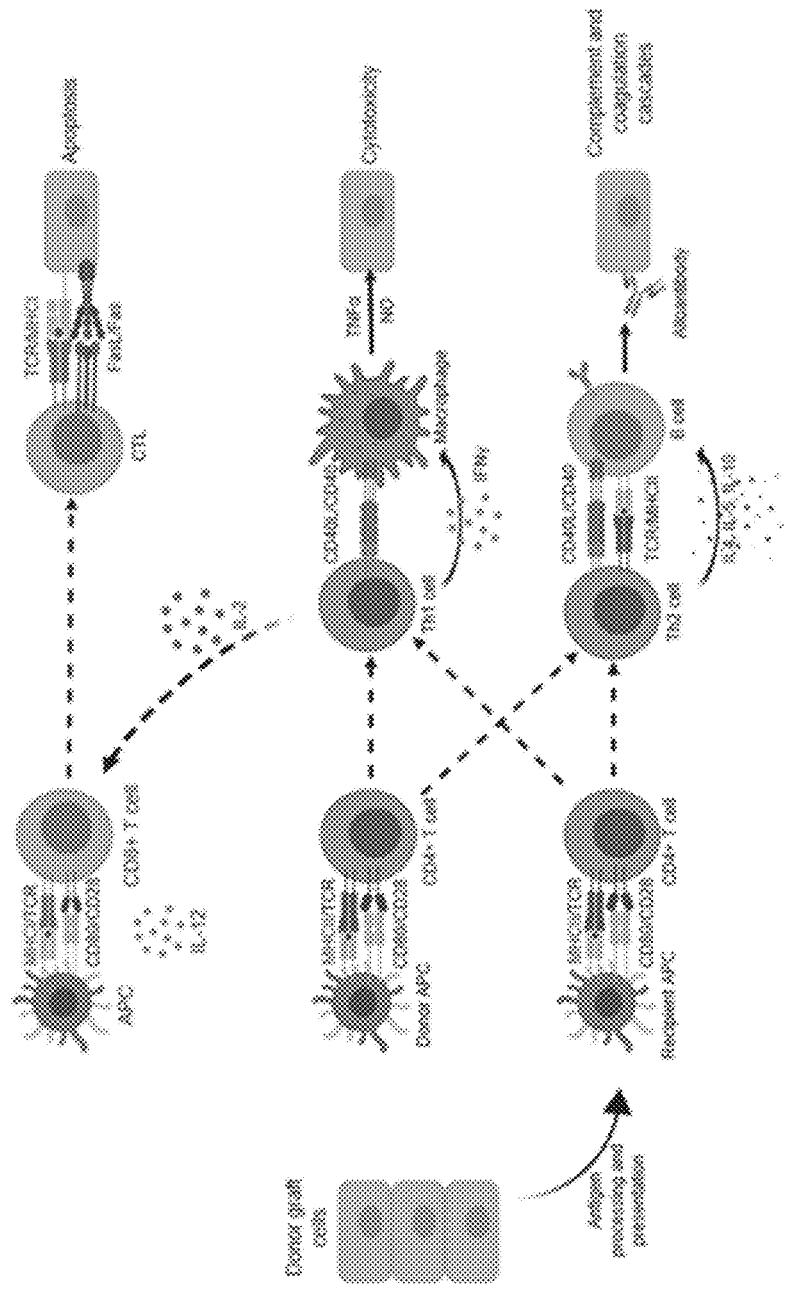
FIG. 15C is a schematic outlining the allograft rejection pathway.

ICOS$^{hi}$ CD4+ T cells were found to be distinct from ICOS$^{lo}$ cells as demonstrated by both transcriptional profiling and immunophenotype assessment by flow cytometry. Patient and donor CD4+ T cell samples formed distinct clusters when applying unsupervised clustering using Pearson's correlation coefficient (FIG. 15A). Gene set enrichment analysis demonstrated trends towards modulation of several pathways (FIG. 15B), and ICOS$^{hi}$ CD4+ T cells, in particular, were found to be enriched in effector pathways. Specifically, allograft rejection pathway components (depicted in FIG. 15C) were found to be upregulated in ICOS$^{hi}$ CD4+ T cells, as compared to ICOS$^{lo}$ CD4+ T cells.

Figure 16A:
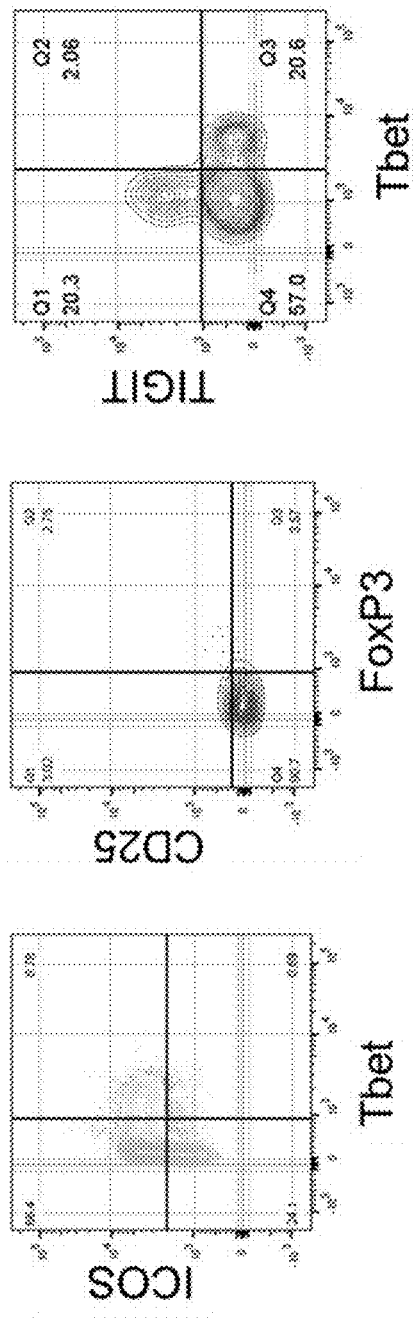
FIG. 16A is a series of contour plots showing Tbet, CD25, FoxP3, and TIGIT expression in a late-cycle uniform ICOS$^{hi}$ T cell population.
Figure 16B:
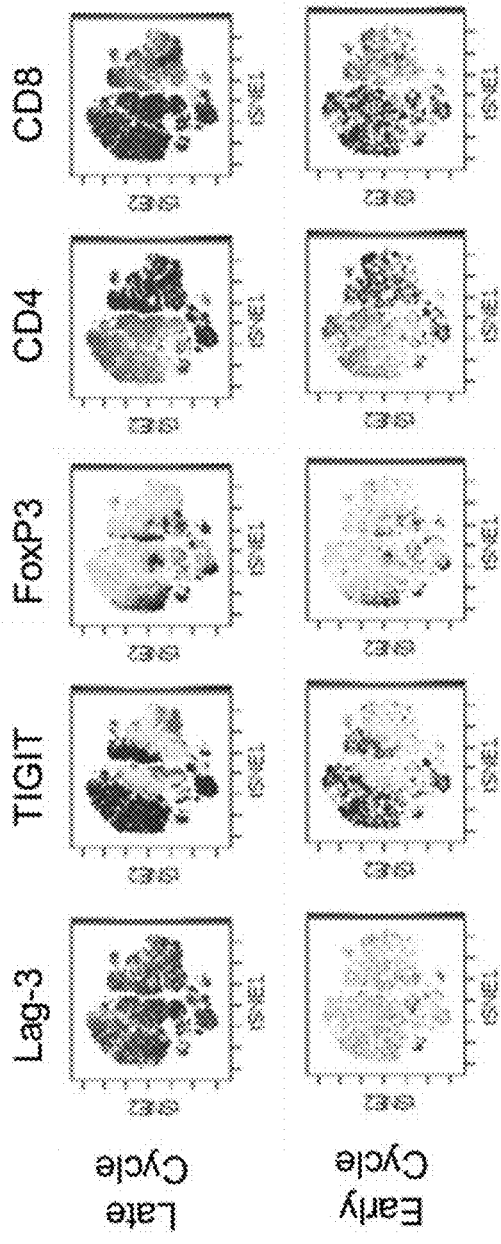
FIG. 16B is a series of plots showing Lag-3, TIGIT, FoxP3, CD4, and CD8 expression in a patient with gastric cancer with a cPR at two time points.

Evaluation of lineage and activation markers in a subject with a late-cycle uniform ICOS$^{hi}$ population revealed ICOS$^{hi}$ CD4+ T cells as T effector cells of primarily the Th1 lineage (FIG. 16A). ICOS$^{hi}$ CD4+ T cells were not enriched in Tregs. Baseline and on-treatment analysis of a gastric cancer subject with a cPR using a T-distributed Stochastic Neighbor Embedding (tSNE) clustering algorithm demonstrated a global reduction in LAG-3 expression and an increase in TIGIT expression on non-Treg cells (FoxP3−) following JTX-2011 treatment (FIG. 16B). Overall, an increase in activation, but not exhaustion, in Tbet+ non-Treg CD4+ and CD8+ T cells was observed in subjects with an emergent ICOS$^{hi}$ population.

Figure 17:
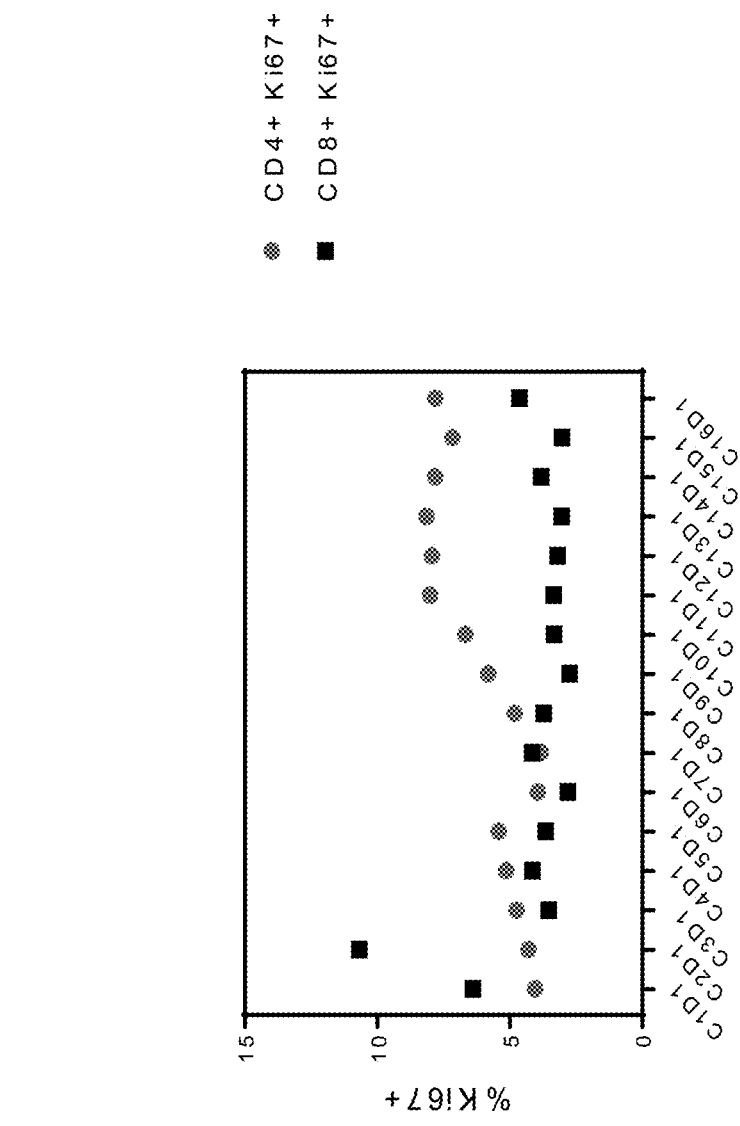
FIG. 17 is a plot showing early and late proliferation of CD8+ and CD4+ T cells in subjects with confirmed PRs to JTX-2011 treatment. Means of 4 subjects profiled longitudinally are shown.

Longitudinal analysis of average Ki-67 staining in subjects with confirmed PRs to JTX-2011 treatment demonstrate early and late proliferation of CD8+ and CD4+ T cells, respectively, characterized by bi-phasic proliferation in subjects with an emergent ICOS$^{hi}$ population (FIG. 17).

Example 8: Examination of T Cell Receptor Repertoire Clonality Following Treatment with JTX-2011

Study Design

T cell receptor repertoire clonality was assessed on peripheral T cells and archival tumor tissue using the Adaptive Biotechnologies ImmunoSeq assay.

Results and Conclusion

Figure 18:
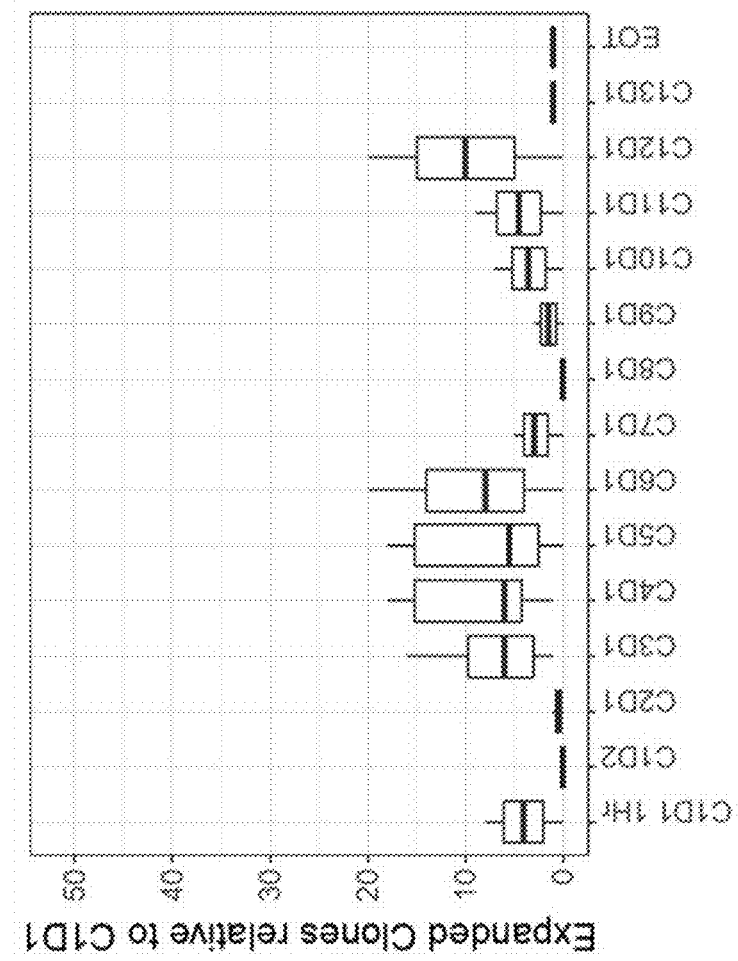
FIG. 18 is a plot showing polyclonal expansion of the TCR repertoire following treatment with JTX-2011. An average of 22 subjects is shown.

Analysis of changes in clonal abundance in the peripheral blood T cell receptor (TCR) repertoire identified significant on-treatment expansion of clones in 18/22 (~82%) of subjects following JTX-2011 treatment, including those from monotherapy. Longitudinal profiling of JTX-2011-induced changes in peripheral clonality demonstrate bi-phasic expansion of the circulating repertoire (FIG. 18). Longitudinal profiling of bystander and tumor-associated clones demonstrates indiscriminate polyclonal expansion of TCR clones in a representative subject without ICOS$^{hi}$ CD4+ T cell emergence (FIG. 19A). Clonal expansion was also observed, but with greater expansion of tumor-associated clones relative to bystander, in a subject with ICOS$^{hi}$ CD4+ T cell emergence (FIG. 19B). Expanded clones detected in the periphery were tumor-associated clones present in archival tumor samples, suggesting that JTX-2011 may function to enhance cell-mediated anti-tumor immunity.

Overall, TCR clonality assessment on-treatment demonstrates clonal expansion, with greater expansion of tumor associated clones in subjects displaying an ICOS$^{hi}$ CD4+ T cell phenotype, while JTX-2011 treatment results in expansion of de novo T cell clones regardless of ICOS$^{hi}$ CD4+ T cell emergence.

Example 9: Analysis of Responding Patient PBMCs

Study Design

PBMCs from a subject with a confirmed PR with a uniform ICOS$^{hi}$ CD4+ T cell population were selected for assessment of antigen-specificity. Stimulation of PBMCs was performed, with IFNγ secretion detected using an ELISPOT reader. Peptides were tested as a pool containing 2 µg/mL of each mutant peptide.

Results and Conclusion

Figures 20A, 20B:
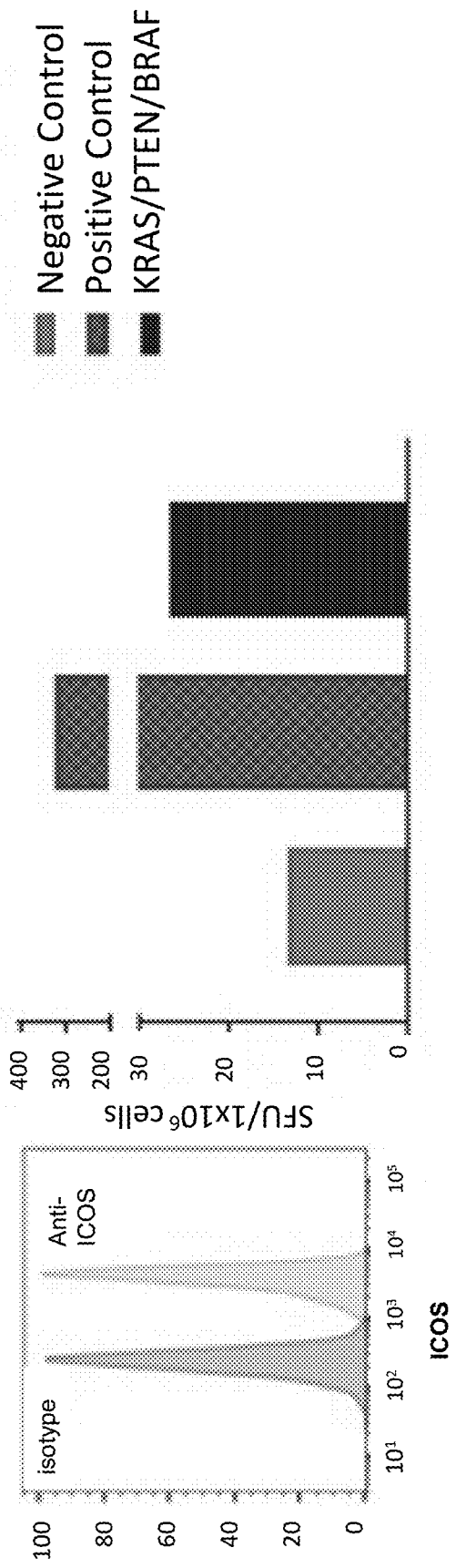
FIG. 20A is a histogram showing uniformity of an ICOS$^{hi}$ CD4+ T cell population of a patient with a cPR by flow cytometry.
FIG. 20B is a graph showing an antigen-specific response, as measured by ELISPOT of PBMCs isolated from a patient with a known mutational status. The first bar is a negative control, the second bar is a positive control, and the third bar is KRAS/PTEN/BRAF. The mutations tested were KRAS G12D, PTEN R173C, and BRAF E26D. Peptides were 15 amino acids in length. The mutation was in the center of the peptide flanked by 7 amino acids of wild-type sequence on each side. The three peptides were pooled with 2 µg/mL each. Positive control was 2 µg/mL of CEF peptide pool consisting of common CMV, EBV, and influenza antigens. Negative control was vehicle.

Flow cytometric analysis demonstrated uniformity of an ICOS$^{hi}$ CD4+ T cell population at a selected time point (FIG. 20A). Analysis of responding patient PBMCs suggests that tumor antigen-specific immune responses can be observed on-treatment (FIG. 20B).

Example 10: Examination of ICOS$^{hi}$ Emergence and Survival

Study Design

Ad hoc flow cytometry phenotyping on PBMCs from a subset of 50 patients from the ICONIC study with evaluable samples was performed. Clinical characteristics and outcomes were analyzed, including unadjusted p-values for post-hoc statistical analyses.

Results and Conclusion

Figure 21:
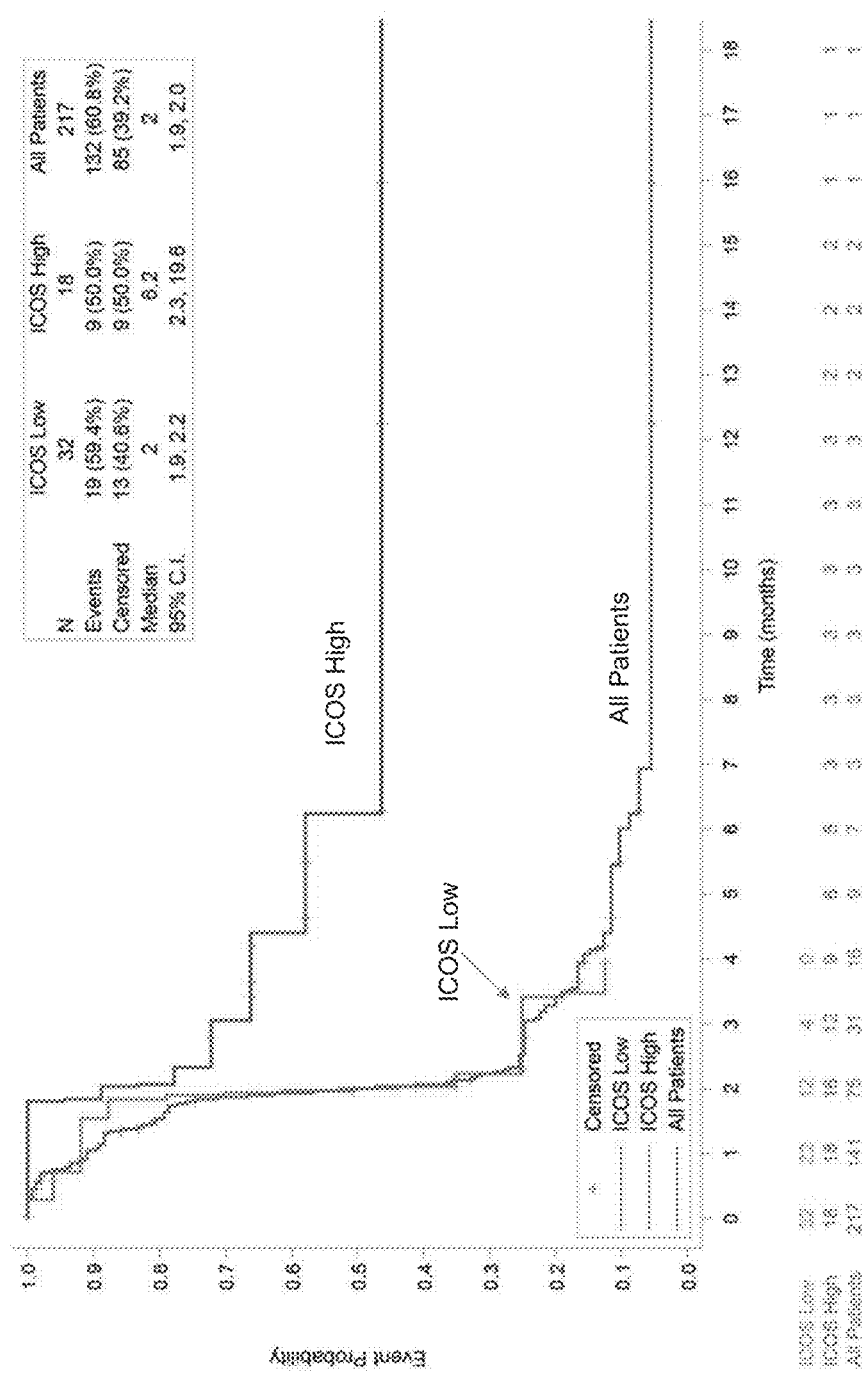
FIG. 21 is a plot showing the six-month median PFS for patients with ICOS$^{hi}$ T cell emergence.
Figure 22:
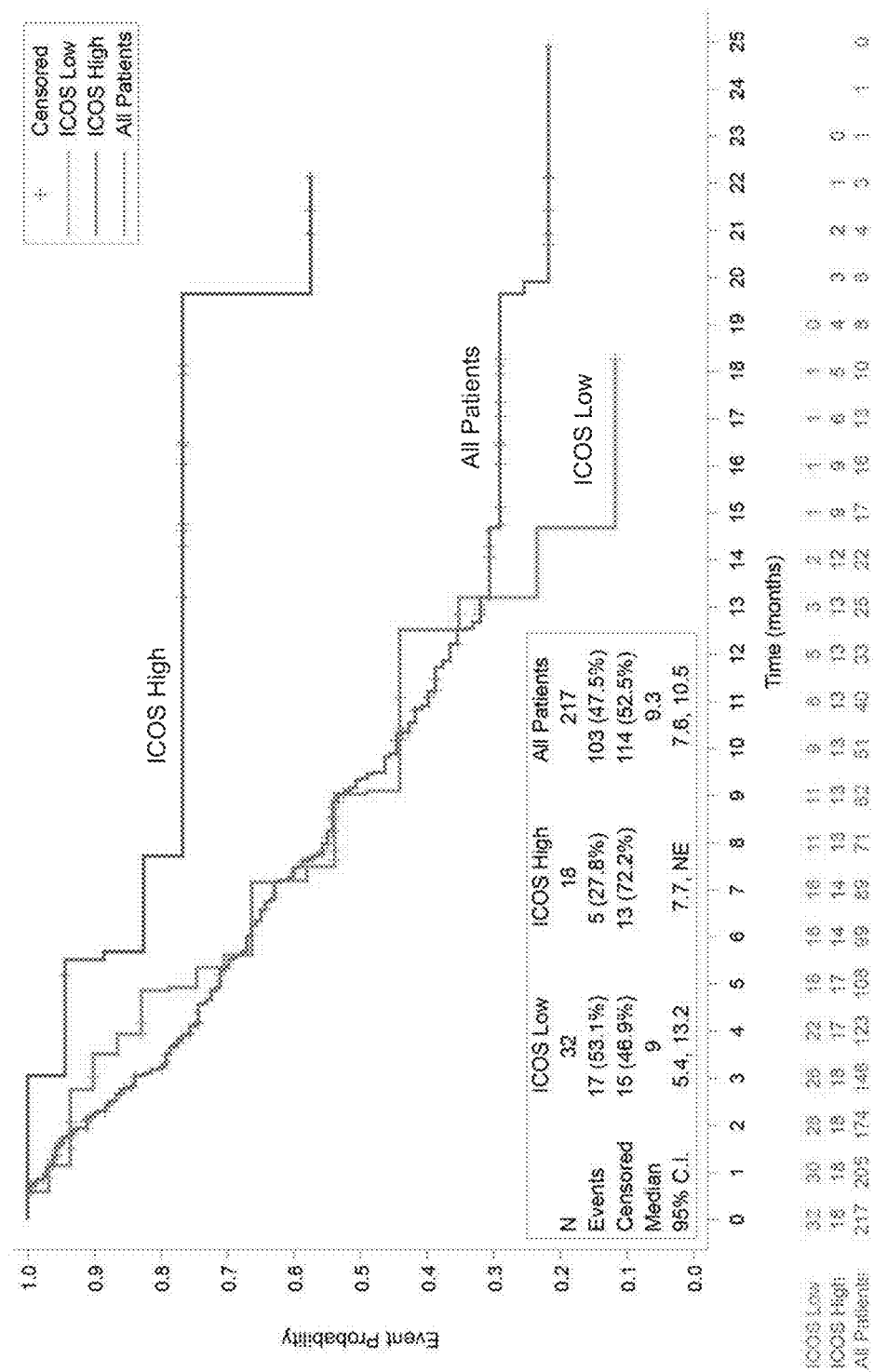
FIG. 22 is a plot showing the median OS for patients with ICOS$^{hi}$ T cell emergence not yet reached.

Emergence of a distinct and persistent population of ICOS$^{hi}$ peripheral CD4+ T cells was associated with improved survival, both with JTX-2011 monotherapy and combination therapy with nivolumab, with improved PFS (FIG. 21) (median 6.2 months for patients with ICOS$^{hi}$ CD4+ T cells versus 2 months for both patients with only ICOS$^{lo}$ CD4+ T cells and all patients on study, including those for whom ICOS$^{hi}$ T cell emergence were not analyzed). Emergence of this distinct population of ICOS$^{hi}$ peripheral CD4+ T cells was also associated with improved OS (FIG. 22) (median not yet reached for patients with ICOS$^{hi}$ CD4+ T cells versus 9 months for patients with only ICOS$^{lo}$ CD4+ T cells and 9.3 months for all ICONIC study patients).

TABLE 2

| Anti-Cancer Therapeutic | Target Name | Anti-Cancer Therapeutic | Target Name |
| --- | --- | --- | --- |
| BMS-986179 | 5'-nucleotidase, ecto (CD73) | imalumab | macrophage migration inhibitory factor (glycosylation-inhibiting factor) |
| pTVG-HP | acid phosphatase, prostate | OSE-2101 | major histocompatibility complex, class I, A |
| sipuleucel-T | acid phosphatase, prostate | andecaliximab | matrix metallopeptidase 9 (gelatinase B, 92 kDa gelatinase, 92 kDa type IV collagenase) |
| CX-2009 | activated leukocyte cell adhesion molecule | anti-MAGE-A3 TOR, Kite Pharma | melanoma antigen family A, 3 |
| luspatercept | activin A receptor type II-like 1 | KITE-718 | melanoma antigen family A, 3 |
| CPI-444 | adenosine A2a receptor | biropepimut-S | melanoma antigen family A, 3 |
| NGR-TNF | alanyl (membrane) aminopeptidase | rituximab biosimilar, Pfizer | membrane-spanning 4-domains, subfamily A, member 1 |
| CB-1158 | arginase 1 arginase 2 | rituximab biosimilar, Dr. Reddy's | membrane-spanning 4-domains, subfamily A, member 1 |
| BA3011 | AXL receptor tyrosine kinase | rituximab biosimilar, Sandoz | membrane-spanning 4-domains, subfamily A, member 1 |

TABLE 2-continued

| Anti-Cancer Therapeutic | Target Name | Anti-Cancer Therapeutic | Target Name |
|---|---|---|---|
| AXL-107-MMAE | AXL receptor tyrosine kinase | rituximab biosimilar, Celltrion | membrane-spanning 4-domains, subfamily A, member 1 |
| CCT301-38 | AXL receptor tyrosine kinase RAR-related orphan receptor A | rituximab biosimilar, Archigen Biotech | membrane-spanning 4-domains, subfamily A, member 1 |
| SurVaxM | baculoviral IAP repeat containing 5 | rituximab biosimilar, Innovent Biologics | membrane-spanning 4-domains, subfamily A, member 1 |
| NY-ESO-1 TOR, Adaptimmune | cancer/testis antigen 1 | MB-106 | membrane-spanning 4-domains, subfamily A, member 1 |
| CDX-1401 | cancer/testis antigen 1 lymphocyte antigen 75 | ibritumomab tiuxetan | membrane-spanning 4-domains, subfamily A, member 1 |
| ETBX-011 | carcinoembryonic antigen-related cell adhesion molecule 5 | rituximab | membrane-spanning 4-domains, subfamily A, member 1 |
| GI-6207 | carcinoembryonic antigen-related cell adhesion molecule 5 | ublituximab | membrane-spanning 4-domains, subfamily A, member 1 |
| falimarev + inalimarev | carcinoembryonic antigen-related cell adhesion molecule 5 mucin 1, cell surface associated | rituximab biosimilar, Allergan/Amgen | membrane-spanning 4-domains, subfamily A, member 1 |
| labetuzumab govitecan | carcinoembryonic antigen-related cell adhesion molecule 5 topoisomerase (DNA) I | ofatumumab | membrane-spanning 4-domains, subfamily A, member 1 |
| coltuximab ravtansine | CD19 molecule | ocaratuzumab | membrane-spanning 4-domains, subfamily A, member 1 |
| denintuzumab mafodotin | CD19 molecule | veltuzumab | membrane-spanning 4-domains, subfamily A, member 1 |
| axicabtagene ciloleucel | CD19 molecule | obinutuzumab | membrane-spanning 4-domains, subfamily A, member 1 |
| CIK-CAR.CD19 | CD19 molecule | rituximab and hyaluronidase human | membrane-spanning 4-domains, subfamily A, member 1 |
| JCAR014 | CD19 molecule | anetumab ravtansine | mesothelin |
| lisocabtagene maraleucel | CD19 molecule | amatuximab | mesothelin |
| tisagenlecleucel | CD19 molecule | emibetuzumab | met proto-oncogene |
| MOR-208 | CD19 molecule | binimetinib | mitogen-activated protein kinase kinase 1 mitogen-activated protein kinase kinase 2 |
| inebilizumab | CD19 molecule | SAR566658 | mucin 1, cell surface associated |
| AUTO3, Autolus | CD19 molecule CD22 molecule | Cvac, Prima Biomed | mucin 1, cell surface associated |
| DT2219ARL | CD19 molecule CD22 molecule | TG4010 | mucin 1, cell surface associated interleukin 2 receptor, alpha |
| blinatumomab | CD19 molecule CD3e molecule, epsilon (CD3-TCR complex) | oregovomab | mucin 16, cell surface associated |
| samalizumab | CD200 molecule | methionine enkephalin based immunotherapy | opioid growth factor receptor |
| inotuzumab ozogamicin | CD22 molecule | olaratumab | platelet-derived growth factor receptor, alpha polypeptide |
| 90Y-epratuzumab tetraxetan | CD22 molecule | enfortumab vedotin | poliovirus receptor-related 4 |
| epratuzumab | CD22 molecule | ProstAtak, Advantagene | polymerase (DNA directed), alpha 1, catalytic subunit |
| ontuxizumab | CD248 molecule, endosialin | PancAtak, Advantagene | polymerase (DNA directed), alpha 1, catalytic subunit |
| varlilumab | CD27 molecule | aglatimagene besadenovec | polymerase (DNA directed), alpha 1, catalytic subunit |

TABLE 2-continued

| Anti-Cancer Therapeutic | Target Name | Anti-Cancer Therapeutic | Target Name |
|---|---|---|---|
| durvalumab | CD274 molecule | IMC-gp100 | premelanosome protein |
| avelumab | CD274 molecule | cemiplimab | programmed cell death 1 |
| atezolizumab | CD274 molecule | AGEN2034 | programmed cell death 1 |
| CX-072 | CD274 molecule | nivolumab | programmed cell death 1 |
| enoblituzumab | CD276 molecule | pembrolizumab | programmed cell death 1 |
| omburtamab | CD276 molecule | spartalizumab | programmed cell death 1 |
| AlloStim, Immunovative Therapies | CD28 molecule | BGB-A317 | programmed cell death 1 |
| gemtuzumab ozogamicin | CD33 molecule | genolimzumab | programmed cell death 1 |
| lintuzumab-Ac225 | CD33 molecule | JNJ-63723283 | programmed cell death 1 |
| BI 836858 | CD33 molecule | MEDI0680 | programmed cell death 1 |
| naratuximab emtansine | CD37 molecule | thymalfasin | prothymosin, alpha |
| lutetium (177Lu) lilotomab satetraxetan | CD37 molecule | LYC-55716 | RAR-related orphan receptor C |
| otlertuzumab | CD37 molecule | cirmtuzumab | receptor tyrosine kinase-like orphan receptor 1 |
| daratumumab | CD38 molecule | VX15/2503 | sema domain, immunoglobulin domain (Ig), transmembrane domain (TM) and short cytoplasmic domain, (semaphorin) 4D |
| isatuximab | CD38 molecule | elotuzumab | SLAM family member 7 |
| TAK-573 | CD38 molecule | indatuximab ravtansine | syndecan 1 |
| A-dmDT390-bisFv (UCHT1) | CD3e molecule, epsilon (CD3-TCR complex) | BMS-986207 | T-cell immunoreceptor with Ig and ITIM domains |
| APX005M | CD40 molecule, TNF receptor superfamily member 5 | tertomotide | telomerase reverse transcriptase |
| Hu5F9-G4 | CD47 molecule | Toca 511 + Toca FC | thymidylate synthetase |
| TI-061 | CD47 molecule | APS001F | thymidylate synthetase |
| milatuzumab | CD74 molecule, major histocompatibility complex, class II invariant chain | JCARH125 | TNF receptor superfamily member 17 |
| polatuzumab vedotin | CD79b molecule, immunoglobulin-associated beta | bb2121 | TNF receptor superfamily member 17 |
| mogamulizumab | chemokine (C-C motif) receptor 4 | AUTO2, Autolus | TNF receptor superfamily member 17 TNF receptor superfamily member 13B |
| BL-8040 | chemokine (C-X-C motif) receptor 4 | OPN-305 | toll-like receptor 2 |
| X4P-001 | chemokine (C-X-C motif) receptor 4 | rintatolimod | toll-like receptor 3 |
| ulocuplumab | chemokine (C-X-C motif) receptor 4 | poly-ICLC | toll-like receptor 3 |
| claudiximab | claudin 18 | ID-G100 | toll-like receptor 4 |
| ALT-836 | coagulation factor III (thromboplastin, tissue factor) | ID-CMB305 | toll-like receptor 4 cancer/testis antigen 1 |
| MCS110 | colony stimulating factor 1 (macrophage) | imiquimod (intravesical), Telormedix | toll-like receptor 7 |
| ARRY-382 | colony stimulating factor 1 (macrophage) colony stimulating factor 1 receptor | NKTR-262 | toll-like receptor 7 toll-like receptor 8 |
| BLZ-945 | colony stimulating factor 1 receptor | motolimod | toll-like receptor 8 |
| AMG 820 | colony stimulating factor 1 receptor | tilsotolimod | toll-like receptor 9 |
| cabiralizumab | colony stimulating factor 1 receptor | sacituzumab govitecan | topoisomerase (DNA) I tumor-associated calcium signal transducer 2 |
| gemogenovatucel-T | colony stimulating factor 2 (granulocyte-macrophage) | HPV-16 E6 TCR, Bluebird Bio/Kite Pharma | transforming protein E6, human papilloma virus-16 |
| GVAX | colony stimulating factor 2 (granulocyte-macrophage) | VGX-3100 | transforming protein E6, human papilloma virus-16 transforming protein E7, |

TABLE 2-continued

| Anti-Cancer Therapeutic | Target Name | Anti-Cancer Therapeutic | Target Name |
|---|---|---|---|
| | | MEDI0457 | human papilloma virus-16 E6 protein, human papilloma virus-18 E7 protein, human papilloma virus-18 transforming protein E6, human papilloma virus-16 transforming protein E7, human papilloma virus-16 E7 protein, human papilloma virus-18 E6 protein, human papilloma virus-18 |
| talimogene laherparepvec | colony stimulating factor 2 (granulocyte-macrophage) | | |
| pexastimogene devacirepvec | colony stimulating factor 2 (granulocyte-macrophage) | TVGV-1 | transforming protein E7, human papilloma virus-16 |
| sargramostim | colony stimulating factor 2 receptor, alpha, low-affinity (granulocyte-macrophage) | KITE-439 | transforming protein E7, human papilloma virus-16 |
| SV-BR-1-GM cancer vaccine | colony stimulating factor 2 receptor, alpha, low-affinity (granulocyte-macrophage) | ADXS-DUAL | transforming protein E7, human papilloma virus-16 |
| pamrevlumab | connective tissue growth factor | axalimogene filolisbac | transforming protein E7, human papilloma virus-16 |
| ipilimumab | cytotoxic T-lymphocyte-associated protein 4 | MVA-5T4 | trophoblast glycoprotein |
| tremelimumab | cytotoxic T-lymphocyte-associated protein 4 | oportuzumab monatox | tumor-associated calcium signal transducer 2 |
| BMS-986249 | cytotoxic T-lymphocyte-associated protein 4 | denosumab | tumour necrosis factor (ligand) superfamily, member 11 |
| rovalpituzumab tesirine | delta-like 3 (*Drosophila*) | BION-1301 | tumour necrosis factor (ligand) superfamily, member 13 |
| ABT-165 | delta-like 4 (*Drosophila*) vascular endothelial growth factor A | belimumab | tumour necrosis factor (ligand) superfamily, member 13b |
| BHQ880 | dickkopf WNT signaling pathway inhibitor 1 | INCAGN1876 | tumour necrosis factor receptor superfamily, member 18 |
| DKN-01 | dickkopf WNT signaling pathway inhibitor 1 | BMS-986156 | tumour necrosis factor receptor superfamily, member 18 |
| Ad-REIC vaccine, Momotaro-Gene | dickkopf WNT signaling pathway inhibitor 3 | INCAGN1949 | tumour necrosis factor receptor superfamily, member 4 |
| AGS-16C3F | ectonucleotide pyrophosphatase/phosphodiesterase 3 | PF-04518600 | tumour necrosis factor receptor superfamily, member 4 |
| carotuximab | endoglin | BMS-986178 | tumour necrosis factor receptor superfamily, member 4 |
| ifabotuzumab | EPH receptor A3 | brentuximab vedotin | tumour necrosis factor receptor superfamily, member 8 |
| CimaVax EGF | epidermal growth factor (beta-urogastrone) | urelumab | tumour necrosis factor receptor superfamily, member 9 |
| depatuxizumab mafodotin | epidermal growth factor receptor | utomilumab | tumour necrosis factor receptor superfamily, member 9 |
| RM-1929 | epidermal growth factor receptor | VBI-1901 | UL83, cytomegalovirus UL55, cytomegalovirus |
| AVID100 | epidermal growth factor receptor | bevacizumab biosimilar, Boehringer Ingelheim | vascular endothelial growth factor A |
| trastuzumab biosimilar, Henlius | epidermal growth factor receptor | bevacizumab-awwb | vascular endothelial growth factor A |
| cetuximab | epidermal growth factor receptor | bevacizumab biosimilar, Pfizer | vascular endothelial growth factor A |
| panitumumab | epidermal growth factor receptor | bevacizumab biosimilar, Oncobiologics | vascular endothelial growth factor A |
| necitumumab | epidermal growth factor receptor | bevacizumab biosimilar, Henlius Biopharmaceuticals | vascular endothelial growth factor A |

TABLE 2-continued

| Anti-Cancer Therapeutic | Target Name | Anti-Cancer Therapeutic | Target Name |
|---|---|---|---|
| nimotuzumab | epidermal growth factor receptor | bevacizumab biosimilar, Fujifilm Kyowa Kirin Biologies | vascular endothelial growth factor A |
| futuximab | epidermal growth factor receptor | aflibercept | vascular endothelial growth factor A |
| tomuzotuximab | epidermal growth factor receptor | bevacizumab | vascular endothelial growth factor A |
| doxorubicin, EDV nanocells, EnGeneIC | epidermal growth factor receptor | pritumumab | vimentin |
| pan-HER | epidermal growth factor receptor erb-b2 receptor tyrosine kinase 2 erb-b2 receptor tyrosine kinase 3 | pexidartinib | v-kit Hardy-Zuckerman 4 feline sarcoma viral oncogene homologue colony stimulating factor 1 receptor fms-related tyrosine kinase 3 |
| trastuzumab deruxtecan | erb-b2 receptor tyrosine kinase 2 | galinpepimut-S | Wilms tumour 1 |
| trastuzumab emtansine | erb-b2 receptor tyrosine kinase 2 | adegramotide/nelatimotide | Wilms tumour 1 |
| (vic-)trastuzumab duocarmazine | erb-b2 receptor tyrosine kinase 2 | JTCR016 | Wilms tumour 1 |
| nelipepimut-S | erb-b2 receptor tyrosine kinase 2 | levamisole | Unknown |
| trastuzumab biosimilar, Merck & Co./Samsung Bioepis | erb-b2 receptor tyrosine kinase 2 | ladiratuzumab vedotin | Unknown |
| trastuzumab biosimilar, Celltrion | erb-b2 receptor tyrosine kinase 2 | NSC-631570 | Unknown |
| trastuzumab biosimilar, Biocon | erb-b2 receptor tyrosine kinase 2 | LN-145 | Unknown |
| trastuzumab biosimilar, Allergan/Amgen | erb-b2 receptor tyrosine kinase 2 | INO-5401 | Unknown |
| trastuzumab biosimilar, Pfizer | erb-b2 receptor tyrosine kinase 2 | AN01, Anson Pharma | Unknown |
| AU101, Aurora Biopharma | erb-b2 receptor tyrosine kinase 2 | GALE-302 | Unknown |
| AU105, Aurora BioPharma | erb-b2 receptor tyrosine kinase 2 | MAGE-A3 TCR, Adaptimmune | Unknown |
| AE37 | erb-b2 receptor tyrosine kinase 2 | BTH-1677 | Unknown |
| trastuzumab | erb-b2 receptor tyrosine kinase 2 | lentinan | Unknown |
| pertuzumab | erb-b2 receptor tyrosine kinase 2 | Polysaccharide-K | Unknown |
| margetuximab | erb-b2 receptor tyrosine kinase 2 | Tice BCG, Organon | Unknown |
| ADXS31-164 | erb-b2 receptor tyrosine kinase 2 | IGEM-F | Unknown |
| ETBX-021 | erb-b2 receptor tyrosine kinase 2 | PV-10, Provectus | Unknown |
| seribantumab | erb-b2 receptor tyrosine kinase 3 | vitespen | Unknown |
| patritumab | erb-b2 receptor tyrosine kinase 3 | mifamurtide | Unknown |
| CDX-3379 | erb-b2 receptor tyrosine kinase 3 | melanoma vaccine, GSK | Unknown |
| elgemtumab | erb-b2 receptor tyrosine kinase 3 | Bacille Calmette-Guerin vaccine, ID Biomedical | Unknown |
| moxetumomab pasudotox | eukaryotic translation elongation factor 2 CD22 molecule | seviprotimut-I | Unknown |
| denileukin diftitox | eukaryotic translation elongation factor 2 interleukin 2 receptor, alpha | in situ autologous cancer vaccine, Immunophotonics | Unknown |
| MDNA55 | eukaryotic translation elongation factor 2 interleukin 4 receptor | IMA901 | Unknown |
| bemarituzumab | fibroblast growth factor receptor 2 | adagloxad simolenin | Unknown |

TABLE 2-continued

| Anti-Cancer Therapeutic | Target Name | Anti-Cancer Therapeutic | Target Name |
|---|---|---|---|
| DCVax-prostate, Northwest Biotherapeutics | folate hydrolase (prostate-specific membrane antigen) 1 | PVX-410 | Unknown |
| 177Lu-J591 | folate hydrolase (prostate-specific membrane antigen) 1 | viagenpumatucel-L | Unknown |
| tuberculosis vaccine (Mw), Cadila; Cadi-05 | folate hydrolase (prostate-specific membrane antigen) 1 | GALE-301 | Unknown |
| mirvetuximab soravtansine | folate receptor 1 (adult) | EP-302, EpiThany | Unknown |
| TPIV200 | folate receptor 1 (adult) | BI 1361849 | Unknown |
| farletuzumab | folate receptor 1 (adult) | DPV-001 | Unknown |
| IGEM-FR | folate receptor 1 (adult) | Bacille Calmette-Guerin vaccine, Sanofi | Unknown |
| G17DT | gastrin | LAMP-Vax + pp65 DC, Immunomic Therapeutics | Unknown |
| codrituzumab | glypican 3 | NKG2D-CAR | Unknown |
| EP-100, EpiThany | gonadotropin-releasing hormone 1 (luteinizing-releasing hormone) luteinizing hormone/chorio-gonadotropin receptor | BPX-501 | Unknown |
| naxitamab | growth differentiation factor 2 | NK-92 cells | Unknown |
| CDX-014 | hepatitis A virus cellular receptor 1 | LN-144 | Unknown |
| MBG453 | hepatitis A virus cellular receptor 2 | CLBS-23 | Unknown |
| histamine dihydrochloride | histamine receptor H2 | DCVax-Direct, Northwest Biotherapeutics | Unknown |
| entinostat | histone deacetylase 1 | melanoma vaccine, AVAX | Unknown |
| indoximod | indoleamine-pyrrole 2,3 dioxygenase | stapuldencel-T | Unknown |
| epacadostat | indoleamine-pyrrole 2,3 dioxygenase | dendritic cancer vaccine, DanDrit Biotech | Unknown |
| BMS-986205 | indoleamine-pyrrole 2,3 dioxygenase | DCVax-Brain brain cancer vaccine, Northwest Biotherapeutics | Unknown |
| JTX-2011 | inducible T-cell co-stimulator | tumor lysate particle-loaded dendritic cell vaccine, Perseus | Unknown |
| BMS-986226 | inducible T-cell co-stimulator | ERC1671 | Unknown |
| ADC W0101 | insulin-like growth factor 1 receptor | BSK01 TAPA pulsed DC vaccine | Unknown |
| ganitumab | insulin-like growth factor 1 receptor | Oncoquest-CLL vaccine | Unknown |
| istiratumab | insulin-like growth factor 1 receptor erb-b2 receptor tyrosine kinase 3 | rocapuldencel-T | Unknown |
| dusigitumab | insulin-like growth factor 1 receptor insulin-like growth factor 2 receptor | ATIR-101 | Unknown |
| EP-201, EpiThany | insulin-like growth factor binding protein 2, 36 kDa | TVI-Kidney-1 | Unknown |
| citoplurikin | interferon gamma receptor 1 tumor necrosis factor receptor superfamily, member 1A | TVAX cancer vaccine, TVAX Biomedical | Unknown |
| MABp1 | interleukin 1, alpha | atezolizumab, companion diagnostic | Unknown |

TABLE 2-continued

| Anti-Cancer Therapeutic | Target Name | Anti-Cancer Therapeutic | Target Name |
|---|---|---|---|
| pegilodecakin | interleukin 10 | tumour infiltrating lymphocytes, lovance Biotherapeutics-2 | Unknown |
| Ad-RTS-hIL-12 + veledimex | interleukin 12 receptor, beta 1 | MAGE A-10 TCR, Adaptimmune | Unknown |
| tavokinogene telsaplasmid | interleukin 12 receptor, beta 1 interleukin 12 receptor, beta 2 | IMA101 | Unknown |
| EGEN-001 | interleukin 12A (natural killer cell stimulatory factor 1, cytotoxic lymphocyte maturation factor 1, p35) interleukin 12B (natural killer cell stimulatory factor 2, cytotoxic lymphocyte maturation factor 2, p40) | algenpantucel-L | Unknown |
| SL-701 | interleukin 13 receptor, alpha 2 EPH receptor A2 baculoviral IAP repeat containing 5 | Tumor Necrosis Therapy, Peregrine | Unknown |
| ALT-803 | interleukin 15 receptor, alpha | imiquimod | Unknown |
| Multikine, Cel-Sci | interleukin 2 receptor, alpha | LOAd703 | Unknown |
| ALT-801 | interleukin 2 receptor, alpha | CG0070 | Unknown |
| high-affinity Natural Killer (haNK) cells, NantKwest | interleukin 2 receptor, alpha | dinutuximab | Unknown |
| interleukin-2, Roche | interleukin 2 receptor, alpha | bavituximab | Unknown |
| aldesleukin | interleukin 2 receptor, alpha | ensituximab | Unknown |
| NKTR-214 | interleukin 2 receptor, beta | pidilizumab | Unknown |
| talacotuzumab | interleukin 3 receptor, alpha (low affinity) | BMS-986218 | Unknown |
| SL-401 | interleukin 3 receptor, alpha (low affinity) | BMS-986012 | Unknown |
| siltuximab | interleukin 6 (interferon, beta 2) | ADXS31-142 | Unknown |
| HuMax-IL8 | interleukin 8 | GI-6301 | Unknown |
| PSA/IL-2/GM-CSF | kallikrein-related peptidase 3 | GI-4000 | Unknown |
| rilimogene galvacirepvec | kallikrein-related peptidase 3 CD80 molecule intercellular adhesion molecule 1 CD58 molecule | JNJ-64041757 | Unknown |
| monalizumab | killer cell lectin-like receptor subfamily C, member 1 | HPV vaccine (Cervarix), GSK | Unknown |
| ramucirumab | kinase insert domain receptor | HPV vaccine (Gardasil), CSL | Unknown |
| ubenimex | leucotriene A4 hydrolase leucotriene B4 receptor | Sym015 | Unknown |
| IMP321 | lymphocyte-activation gene 3 | diphenylcyclopropenone | Unknown |
| LAG525 | lymphocyte-activation gene 3 | ISA101 | Unknown |
| relatlimab | lymphocyte-activation gene 3 | | |

TABLE 3

Sequences

| Name (Target, if applicable) | Region | SEQ ID NO | Sequence |
|---|---|---|---|
| JTX-2011 (ICOS) | Heavy Chain | 1 | EVQLVESGGGLVQPGGSLRLSCAASGFTFSDYWMDWVRQAPGKGLVWVSNI DEDGSITEYSPFVKGRFTISRDNAKNTLYLQMNSLRAEDTAVYYCTRWGRF GFDSWGQGTLVTVSSASTKGPSVFPLAPSSKSTSGGTAALGCLVKDYFPEP |

TABLE 3-continued

Sequences

| Name (Target, if applicable) | Region | SEQ ID NO | Sequence |
|---|---|---|---|
| | | | VTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISR TPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYS KLTVDKSRWQQGNVFSCSVMHEALHNHYTQKSLSLSPG |
| JTX-2011 (ICOS) | Light Chain | 2 | DIVMTQSPDSLAVSLGERATINCKSSQSLLSGSFNYLTWYQQKPGQ PPKLLIFYASTRHTGVPDRFSGSGSGTDFTLTISSLQAEDVAVYYC HHHYNAPPTFGPGTKVDIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSFNRGEC |
| JTX-2011 (ICOS) | Heavy Chain Variable Region | 3 | EVQLVESGGGLVQPGGSLRLSCAASGFTFSDYWMDWVRQAPGKGLVWVSNI DEDGSITEYSPFVKGRFTISRDNAKNTLYLQMNSLRAEDTAVYYCTRWGRF GFDSWGQGTLVTVSS |
| JTX-2011 (ICOS) | Light Chain Variable Region | 4 | DIVMTQSPDSLAVSLGERATINCKSSQSLLSGSFNYLTWYQQKPGQPPKLL IFYASTRHTGVPDRFSGSGSGTDFTLTISSLQAEDVAVYYCHHHYNAPPTF GPGTKVDIK |
| JTX-2011 (ICOS) | HCDR1 | 5 | GFTFSDYWMD |
| JTX-2011 (ICOS) | HCDR2 | 6 | NIDEDGSITEYSPFVK |
| JTX-2011 (ICOS) | HCDR3 | 7 | WGRFGFDS |
| JTX-2011 (ICOS) | LCDR1 | 8 | KSSQSLLSGSFNYLT |
| JTX-2011 (ICOS) | LCDR2 | 9 | YASTRHT |
| JTX-2011 (ICOS) | LCDR3 | 10 | HHHYNAPPT |
| Human ICOS precursor with signal sequence | | 11 | MKSGLWYFFLFCLRIKVLTGEINGSANYEMFIFHNGGVQILCKYPDIVQQF KMQLLKGGQILCDLTKTKGSGNTVSIKSLKFCHSQLSNNSVSFFLYNLDHS HANYYFCNLSIFDPPPPKVTLTGGYLHIYESQLCCQLKFWLPIGCAAFVVV CILGCILICWLTKKKYSSSVHDPNGEYMFMRAVNTAKKSRLTDVTL (Intracellular Region is underlined) |
| Human ICOS, mature | | 12 | EINGSANYEMFIFHNGGVQILCKYPDIVQQFKMQLLKGGQILCDLTKTKGS GNTVSIKSLKFCHSQLSNNSVSFFLYNLDHSHANYYFCNLSIFDPPPPKVT LTGGYLHIYESQLCCQLKFWLPIGCAAFVVVCILGCILICWLTKKKYSSSV HDPNGEYMFMRAVNTAKKSRLTDVTL (Intracellular Region is underlined) |
| Mouse (*Mus musculus*) ICOS precursor | | 13 | MKPYFCRVFVFCFLIRLLTGEINGSADHRMFSFHNGGVQISCKYPE TVQQLKMRLFREREVLCELTKTKGSGNAVSIKNPMLCYHLSNNSV SFFLNNPDSSQGSYYFCSLSIFDPPPPQERNLSGGYLHIYESQLCC QLKLWLPVGCAAFVVVLLFGCILIIWFSKKKYGSSVHDPNSEYMFM AAVNTNKKSRLAGVTS |
| Mouse (*Mus musculus*) ICOS, mature | | 14 | EINGSADHRMFSFHNGGVQISCKYPETVQQLKMRLFREREVLCELT KTKGSGNAVSIKNPMLCYHLSNNSVSFFLNNPDSSQGSYYFCSLS IFDPPPPQERNLSGGYLHIYESQLCCQLKLWLPVGCAAFVVVLLFG CILIIWFSKKKYGSSVHDPNSEYMFMAAVNTNKKSRLAGVTS |
| Rat (*Rattus norvegicus*) ICOS precursor | | 15 | MKPYFSCVFVFCFLIKLLTGELNDLANHRMFSFHDGGVQISCNYPE TVQQLKMQLFKDREVLCDLIKTKGSGNIVSIKNPMSCPYQLSNNSV SFFLDNADSSQGSYFLCSLSIFDPPPPQEKNLSGGYLLIYESQLCC QLKLWLPVGCAAFVAALLFGCIFIVWFAKKKYRSSVHDPNSEYMFM AAVNTNKKSRLAGMTS |
| Rat (*Rattus norvegicus*) ICOS, mature | | 16 | ELNDLANHRMFSFHDGGVQISCNYPETVQQLKMQLFKDREVLCDLTKTKGS GNTVSIKNPMSCPYQLSNNSVSFFLDNADSSQGSYFLCSLSIFDPPPPFQEK NLSGGYLLIYESQLCCQLKLWLPVGCAAFVAALLFGCIFIVWFAKKKYRSS VHDPNSEYMFMAAVNTNKKSRLAGMTS |

TABLE 3-continued

Sequences

| Name (Target, if applicable) | Region | SEQ ID NO | Sequence |
|---|---|---|---|
| Cynomolgus monkey (*Macaca fascicularis*) ICOS, precursor | | 17 | MKSGLWYFFLFCLHMKVLTGEINGSANYEMFIFHNGGVQILCKYPDIVQQF KMQLLKGGQILCDLTKTKGSGNKVSIKSLKFCHSQLSNNSVSFFLYNLDRS HANYYFCNLSIFDPPPFKVTLTGGYLHIYESQLCCQLKFWLPIGCATFVVV CIFGCILICWLTKKKYSSTVHDPNGEYMFMRAVNTAKKSRLTGTTP |
| Cynomolgus monkey (*Macaca fascicularis*) ICOS, mature | | 18 | EINGSANYEMFIFHNGGVQILCKYPDIVQQFKMQLLKGGQILCDLT KTKGSGNKVSIKSLKFCHSQLSNNSVSFFLYNLDRSHANYYFCNLS IFDPPPFKVTLTGGYLHIYESQLCCQLKFWLPIGCATFVVVCIFGC ILICWLTKKKYSSTVHDPNGEYMFMRAVNTAKKSRLTGTTP |
| JNC-1 (PD-1) | Heavy Chain Variable Region | 19 | QVQLVQSGAEVKKPGASVKVSCKASGYTFPSYYMHWVRQAPGQGLEWMGII NPEGGSTAYAQKFQGRVTMTRDTSTSTVYMELSSLRSEDTAVYYCARGGTY YDYTYWGQGTLVTVSS |
| JNC-1 (PD-1) | HCDR1 | 20 | YTFPSYYMH |
| JNC-1 (PD-1) | HCDR2 | 21 | IINPEGGSTAYAQKFQG |
| JNC-1 (PD-1) | HCDR3 | 22 | ARGGTYYDYTY |
| JNC-1 (PD-1) | Light Chain Variable Region | 23 | DIQMTQSPSTLSASVGDRVTITCRASQSISSWLAWYQQKPGKAPKLLIYEA SSLESGVPSRFSGSGSGTEFTLTISSLQPDDFATYYCQQYNSFPPTFGGGT KVEIK |
| JNC-1 (PD-1) | LCDR1 | 24 | RASQSISSWLA |
| JNC-1 (PD-1) | LCDR2 | 25 | EASSLES |
| JNC-1 (PD-1) | LCDR3 | 26 | QQYNSFPPT |
| 2M13 (ICOS intracellular) | Heavy Chain Variable Region | 27 | EVQLQQSGAELVRPGAVVKLSCKASGFDIKDYYMHWVQQRPEQGLEWIGWI DPENGNAVYDPQFQGKASITADTSSNTAYLQLSSLTSEDTAVYYCASDYYG SKGYLDVWGAGTTVTVSS |
| 2M13 (ICOS intracellular) | HCDR1 | 28 | DYYMH |
| 2M13 (ICOS intracellular) | HCDR2 | 29 | WIDPENGNAVYDPQFQG |
| 2M13 (ICOS intracellular) | HCDR3 | 30 | DYYGSKGYLDV |
| 2M13 (ICOS intracellular) | Light Chain Variable Region | 31 | QIVLTQSPTIMSASPGEKVTITCSASSSVSYMHWFQQKPGTSPKLWIYSTS NLASGVPARFGGSRSGTSYSLTISRMEAEDAATYYCQQRSSYPFTFGSGTK LEIK |
| 2M13 (ICOS intracellular) | LCDR1 | 32 | SASSSVSYMH |
| 2M13 (ICOS intracellular) | LCDR2 | 33 | STSNLAS |
| 2M13 (ICOS intracellular) | LCDR3 | 34 | QQRSSYPFT |
| 2M19 (ICOS intracellular) | Heavy Chain Variable Region | 35 | EVQLQQSGAELVRSGASVKLSCTTSAFNIIDYYMHWVIQRPEQGLEWIAWI DPENGDPEYAPKFQDKATMTTDTSSNTAYLQLSSLTSEDTAVYYCTAWRGF AYWGQGTLVTVSA |

TABLE 3-continued

Sequences

| Name (Target, if applicable) | Region | SEQ ID NO | Sequence |
|---|---|---|---|
| 2M19 (ICOS intra-cellular) | HCDR1 | 36 | DYYMH |
| 2M19 (ICOS intra-cellular) | HCDR2 | 37 | WIDPENGDPEYAPKFQD |
| 2M19 (ICOS intra-cellular) | HCDR3 | 38 | WRGFAY |
| 2M19 (ICOS intra-cellular) | Light Chain Variable Region | 39 | DVVMTQTPLSLPVSLGDQASISCRSSQSLVHSNGNTYLHWYLQKPGQSPKL LIYKVSNRFSGVPDRFSGSGSGTDFTLKISRVEAEDLGVYFCSQSIHVPPT FGGGTKLEIK |
| 2M19 (ICOS intra-cellular) | LCDR1 | 40 | RSSQSLVHSNGNTYLH |
| 2M19 (ICOS intra-cellular) | LCDR2 | 41 | KVSNRFS |
| 2M19 (ICOS intra-cellular) | LCDR3 | 42 | SQSIHVPPT |
| Human T-bet | | 43 | MGIVEPGCGDMLTGTEPMPGSDEGRAPGADPQHRYFYPEPGAQDADERRGG GSLGSPYPGGALVPAPPSRFLGAYAYPPRPQAAGFPGAGESFPPPADAEGY QPGEGYAAPDPRAGLYPGPREDYALPAGLEVSGKLRVALNNHLLWSKFNQH QTEMIITKQGRRMFPFLSFTVAGLEPTSHYRMFVDVVLVDQHHWRYQSGKW VQCGKAEGSMPGNRLYVHPDSPNTGAHWMRQEVSFGKLKLTNNKGASNNVT QMIVLQSLHKYQPRLHIVEVNDGEPEAACNASNTHIFTFQETQFIAVTAYQ NAEITQLKIDNNPFAKGFRENFESMYTSVDTSIPSPPGPNCQFLGGDHYSP LLPNQYPVPSRFYPDLPGQAKDVVPQAYWLGAPRDHSYEAEFRAVSMKPAF LPSAPGPTMSYYRGQEVLAPGAGWPVAPQYPPKMGPASWFRPMRTLPMEPG PGGSEGRGPEDQGPPLVWTEIAPIRPESSDSGLGEGDSKRRRVSPYPSSGD SSSPAGAPSPFDKEAEGQFYNYFPN |
| Mouse (*Mus musculus*) T-bet | | 44 | MGIVEPGCGDMLTGTEPMPSDEGRGPGADQQHRFFYPEPGAQDPTDRRAGS SLGTPYSGGALVPAAPGRFLGSFAYPPRAQVAGFPGPGEFFPPPAGAEGYP PVDGYPAPDPRAGLYPGPREDYALPAGLEVSGKLRVALSNHLLWSKFNQHQ TEMIITKQGRRMFPFLSFTVAGLEPTSHYRMFVDVVLVDQHHWRYQSGKWV QCGKAEGSMPGNRLYVHPDSPNTGAHWMRQEVSFGKLKLTNNKGASNNVTQ MIVLQSLHKYQPRLHIVEVNDGEPEAACSASNTHVFTFQETQFIAVTAYQN AEITQLKIDNNPFAKGFRENFESMYASVDTSVPSPPGPNCQLLGGDPFSPL LSNQYPVPSRFYPDLPGQPKDMISQPYWLGTPREHSYEAEFRAVSMKPTLL PSAPGPTVPYYRGQDVLAPGAGWPVAPQYPPKMSPAGWFRPMRTLPMDPGL GSSEEQGSSPSLWPEVTSLQPEPSDSGLGEGDTKRRRISPYPSSGDSSSPA GAPSPFDKETEGQFYNYFPN |

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein. Some embodiments of the invention are within the following numbered paragraphs.

1. A method of treating cancer in a subject in need thereof, the method comprising (i) administering one or more dosages of one or more anti-cancer therapies to the subject, (ii) after the administration, obtaining one or more peripheral blood test samples from the subject, (iii) measuring ICOS and/or T-bet levels of CD4+ T cells present in the one or more peripheral blood test samples, (iv) determining if there is a population of CD4+ T cells having elevated ICOS and/or T-bet levels in any of the one or more peripheral blood test samples when compared to a control, and (v) administering (a) one or more additional dosages of the one or more anti-cancer therapies, or (b) an anti-ICOS agonist, to the subject if any of the one or more peripheral blood test samples is determined to comprise a population of CD4+ T cells having elevated ICOS and/or T-bet levels.

2. The method of paragraph 1, wherein step (iii) comprises measuring ICOS levels of CD4+ T cells present in the one or more peripheral blood test samples, step (iv) comprises determining if there is a population of CD4+ T cells having elevated ICOS levels in any one of the one or more peripheral blood test samples when compared to a control, and step (v) comprises administering (a) one or more additional dosages of the one or more anti-cancer therapies, or (b) an anti-ICOS agonist, to the subject if any of the one or more peripheral blood test samples is determined to comprise a population of CD4+ T cells having elevated ICOS levels.

3. The method of paragraph 1 or 2, wherein step (iii) comprises measuring T-bet levels of CD4+ T cells present in the one or more peripheral blood test samples, step (iv) comprises determining if there is a population of CD4+ T cells having elevated T-bet levels in any one of the one or more peripheral blood test samples when compared to a control, and step (v) comprises administering (a) one or more additional dosages of the one or more anti-cancer therapies, or (b) an anti-ICOS agonist, to the subject if any of the one or more peripheral blood test samples is determined to comprise a population of CD4+ T cells having elevated T-bet levels.

4. The method of paragraph 1, wherein step (iii) comprises measuring ICOS and T-bet levels of CD4+ T cells present in the one or more peripheral blood test samples, step (iv) comprises determining if there is a population of CD4+ T cells having elevated ICOS and T-bet levels in any one of the one or more peripheral blood test samples when compared to a control, and step (v) comprises administering (a) one or more additional dosages of the one or more anti-cancer therapies, or (b) an anti-ICOS agonist, to the subject if any of the one or more peripheral blood test samples is determined to comprise a population of CD4+ T cells having elevated ICOS and/or T-bet levels.

5. The method of paragraph 1, wherein step (iii) comprises measuring ICOS and T-bet levels of CD4+ T cells present in the one or more peripheral blood test samples, step (iv) comprises determining if there is a population of CD4+ T cells having elevated ICOS and T-bet levels in any one of the one or more peripheral blood test samples when compared to a control, and step (v) comprises (a) administering one or more additional dosages of the one or more anti-cancer therapies, or (b) an anti-ICOS agonist, to the subject if any of the one or more peripheral blood test samples is determined to comprise a population of CD4+ T cells having elevated ICOS and T-bet levels.

6. A method for determining whether a subject may benefit from (a) continued treatment with one or more anti-cancer therapies or (b) treatment with an anti-ICOS agonist, the method comprising determining ICOS and/or T-bet levels of peripheral CD4+ T cells of a sample of blood of the subject, wherein detection of increased ICOS and/or T-bet levels relative to a control indicates that the subject may benefit from the continued treatment, optionally in combination with an anti-ICOS antibody agonist, or treatment with an anti-ICOS agonist, when the one or more anti-cancer therapies does not comprise anti-ICOS antibody agonist treatment.

7. The method of paragraph 6, wherein the method comprises determining ICOS levels of peripheral CD4+ T cells of a sample of blood of the subject, wherein detection of increased ICOS levels relative to a control indicates that the subject may benefit from the continued treatment, optionally in combination with an anti-ICOS antibody agonist, or treatment with an anti-ICOS agonist, when the one or more anti-cancer therapies does not comprise anti-ICOS antibody agonist treatment.

8. The method of paragraph 6 or 7, wherein the method comprises determining T-bet levels of peripheral CD4+ T cells of a sample of blood of the subject, wherein detection of increased T-bet levels relative to a control indicates that the subject may benefit from the continued treatment, optionally in combination with an anti-ICOS antibody agonist, or treatment with an anti-ICOS agonist, when the one or more anti-cancer therapies does not comprise anti-ICOS antibody agonist treatment.

9. The method of paragraph 6, wherein the method comprises determining ICOS and T-bet levels of peripheral CD4+ T cells of a sample of blood of the subject, wherein detection of increased ICOS or T-bet levels relative to a control indicates that the subject may benefit from the continued treatment, optionally in combination with an anti-ICOS antibody agonist, or treatment with an anti-ICOS agonist, when the one or more anti-cancer therapies does not comprise anti-ICOS antibody agonist treatment.

10. The method of any one of paragraphs 1 to 9, wherein the one or more anti-cancer therapies comprises an immunotherapy.

11. The method of any one of paragraphs 1 to 10, wherein the one or more anti-cancer therapies comprises an anti-CTLA-4 antagonist antibody.

12. The method of paragraph 11, wherein the anti-CTLA-4 antagonist antibody is selected from the group consisting of ipilimumab, tremelimumab, and BMS-986249.

13. The method of paragraph 12, wherein the anti-CTLA-4 antagonist antibody is ipilimumab.

14. The method of any one of paragraphs 1 to 13, wherein the one or more anti-cancer therapies comprises an anti-PD-1 or anti-PD-L1 antagonist antibody.

15. The method of paragraph 14, wherein the anti-PD-1 or anti-PD-L1 antagonist antibody is selected from the group consisting of avelumab, atezolizumab, CX-072, pembrolizumab, nivolumab, cemiplimab, spartalizumab, tislelizumab, JNJ-63723283, genolimzumab, AMP-514, AGEN2034, durvalumab, and JNC-1.

16. The method of paragraph 15, wherein the anti-PD-1 or anti-PD-L1 antagonist antibody is selected from the group consisting of pembrolizumab, nivolumab, atezolizumab, avelumab, and duravalumab.

17. The method of any one of paragraphs 1 to 16, wherein the one or more anti-cancer therapies, or the anti-ICOS agonist, comprises an anti-ICOS agonist antibody.

18. The method of paragraph 17, wherein the anti-ICOS agonist antibody is selected from the group consisting of JTX-2011, BMS-986226, and GSK3359609.

19. The method of any one of paragraphs 1 to 18, wherein the one or more anti-cancer therapies comprises one or more of the therapies listed in Table 2.

20. The method of any one of paragraphs 1 to 19, wherein the one or more anti-cancer therapies comprises a chemotherapy.

21. The method of paragraph 20, wherein the chemotherapy is selected from the group consisting of capecitabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, pemetrexed, vinorelbine, vincristine, erlotinib, afatinib, gefitinib, crizotinib, dabrafenib, trametinib, vemurafenib, and cobimetanib.

22. The method of any one of paragraphs 1 to 21, wherein the one or more anti-cancer therapies comprises radiation therapy.

23. The method of any one of paragraphs 1 to 5 and 10 to 22, wherein step (v) comprises administration of an anti-ICOS antibody agonist to the subject if any of the one or more peripheral blood test samples is determined to comprise a population of CD4+ T cells having elevated ICOS and/or T-bet levels.

24. The method of any one of paragraphs 6 to 23, wherein the anti-ICOS antibody agonist comprises at least one CDR selected from the group consisting of: (a) an HCDR1 comprising the amino acid sequence of SEQ ID NO: 5; (b) an HCDR2 comprising the amino acid sequence of SEQ ID NO: 6; (c) an HCDR3 comprising the amino acid sequence of SEQ ID NO: 7; (d) an LCDR1 comprising the amino acid sequence of SEQ ID NO: 8; (e) an LCDR2 comprising the amino acid sequence of SEQ ID NO: 9; and (f) an LCDR3 comprising the amino acid sequence of SEQ ID NO: 10, wherein one or more of the CDRs comprises 1 or 2 amino acid substitutions.

25. The method of paragraph 24, wherein the anti-ICOS antibody agonist comprises (a) an HCDR1 comprising the amino acid sequence of SEQ ID NO: 5; (b) an HCDR2 comprising the amino acid sequence of SEQ ID NO: 6; (c) an HCDR3 comprising the amino acid sequence of SEQ ID NO: 7; (d) an LCDR1 comprising the amino acid sequence of SEQ ID NO: 8; (e) an LCDR2 comprising the amino acid sequence of SEQ ID NO: 9; and (f) an LCDR3 comprising the amino acid sequence of SEQ ID NO: 10.

26. The method of any one of paragraphs 6 to 25, wherein the anti-ICOS antibody agonist comprises (a) a heavy chain comprising the amino acid sequence of SEQ ID NO: 1 and/or (b) a light chain comprising the amino acid sequence of SEQ ID NO: 2.

27. The method of any one of paragraphs 1 to 26, wherein the one or more anti-cancer therapies comprises any combination of at least two of: (i) an anti-CTLA-4 antagonist antibody, (ii) an anti-PD-1 or anti-PD-L1 antagonist antibody, (iii) an anti-ICOS agonist antibody, (iv) a therapy of Table 2, (v) a chemotherapy, and (vi) radiation therapy.

28. The method of any one of paragraphs 1 to 27, wherein the one or more anti-cancer therapies comprises any combination of at least three of: (i) an anti-CTLA-4 antagonist antibody, (ii) an anti-PD-1 or anti-PD-L1 antagonist antibody, (iii) an anti-ICOS agonist antibody, (iv) a therapy of Table 2, (v) a chemotherapy, and (vi) radiation therapy.

29. The method of any one of paragraphs 1 to 5 and 10 to 28, wherein the one or more anti-cancer therapies is administered two or more times prior to obtaining the one or more peripheral blood test samples.

30. The method of paragraph 29, wherein the one or more anti-cancer therapies is administered three or more times prior to obtaining the one or more peripheral blood test samples.

31. The method of paragraph 30, wherein the one or more anti-cancer therapies is administered four or more times prior to obtaining the one or more peripheral blood test samples.

32. The method of paragraph 31, wherein the one or more anti-cancer therapies is administered five or more times prior to obtaining the one or more peripheral blood test samples.

33. The method of any one of paragraphs 1 to 5 and 10 to 32, wherein the obtaining of the one or more peripheral blood test samples is performed fewer than 4 weeks after the one or more administrations of the dosages of the one or more anti-cancer therapies.

34. The method of paragraph 33, wherein the obtaining of the one or more peripheral blood test samples is performed fewer than 3 weeks after the one or more administrations of the dosages of the one or more anti-cancer therapies.

35. The method of paragraph 34, wherein the obtaining of the one or more peripheral blood test samples is performed fewer than 2 weeks after the one or more administrations of the dosages of the one or more anti-cancer therapies.

36. The method of paragraph 35, wherein the obtaining of the one or more peripheral blood test samples is performed less than one week after the one or more administrations of the dosages of the one or more anti-cancer therapies.

37. The method of any one of paragraphs 1 to 5 and 10 to 36, wherein the dosage of the one or more anti-cancer therapies is administered multiple times at regular intervals.

38. The method of paragraph 37, wherein the regular intervals are selected from the group consisting of a dosage every week, a dosage every two weeks, a dosage every three weeks, a dosage every four weeks, a dosage every six weeks, a dosage every nine weeks, and a dosage every twelve weeks.

39. The method of paragraph 37 or 38, wherein the obtaining of the one or more peripheral blood test samples comprises the obtaining of multiple peripheral blood test samples, with test samples being obtained concurrent with one or more of the administrations.

40. The method of paragraph 37 or 38, wherein the obtaining of the one or more peripheral blood test samples comprises the obtaining of multiple peripheral blood test samples, with test samples being obtained during a time intervening the multiple administrations.

41. The method of any one of paragraphs 37 to 40, wherein the method further comprises halting the administration of the one or more anti-cancer therapies if, after the one or more anti-cancer therapies is administered for four or more intervals, a population of CD4+ T cells having elevated ICOS and/or T-bet levels compared to a control is not detected in any one of the peripheral blood test samples.

42. The method of paragraph 41, wherein the method further comprises halting the administration of the one or more anti-cancer therapies if, after of the one or more anti-cancer therapies is administered for five or more, six or more, seven or more, eight or more, nine or more, or ten or more intervals, a peripheral blood test sample is obtained based on which it is determined that there is not a population of CD4+ T cells having elevated ICOS and/or T-bet levels compared to a control.

43. The method of any one of paragraphs 1 to 42, wherein the method further comprises storing a portion of one or more of the peripheral blood test samples.

44. The method of any one of paragraphs 1 to 43, wherein a portion of the CD4+ T cells having elevated ICOS and/or T-bet levels is isolated from one or more of the peripheral blood test samples and stored under conditions suitable for maintaining the viability of the CD4+ T cells.

45. The method of paragraph 44, wherein the stored CD4+ T cells are stored in a cell culture medium.

46. The method of paragraph 44 or 45, wherein the stored CD4+ T cells are stored at a concentration of greater than 100,000 cells/mL.

47. The method of paragraph 46, wherein the stored CD4+ T cells are stored at a concentration between 100,000 cells/mL and 100 million cells/mL.

48. A suspension of CD4+ T cells obtained according to the method of any one of paragraphs 44 to 47.

49. The method of any one of paragraphs 1 to 47, wherein the control comprises a peripheral blood test sample, which is optionally obtained from the subject before one or more of the administrations of the one or more anti-cancer therapies to the subject.

50. The method of any one of paragraphs 1 to 47, wherein the control comprises a peripheral blood sample obtained from a healthy individual not receiving the one or more anti-cancer therapies.

51. The method of any one of paragraphs 1 to 47, 49, and 50, wherein determining of ICOS and/or T-bet levels comprises the use of an immunoassay.

52. The method of paragraph 51, wherein the immunoassay comprises the use of an antibody that binds to an intracellular domain of ICOS to detect ICOS.

53. The method of paragraph 52, wherein the antibody comprises a heavy chain variable region sequence of SEQ ID NO: 27 and a light chain variable region sequence of SEQ ID NO: 31; or the antibody comprises a heavy chain variable region sequence of SEQ ID NO: 35 and a light chain variable region sequence of SEQ ID NO: 39.

54. The method of paragraph 52, wherein the antibody cross-competes with an antibody comprising a heavy chain variable region sequence of SEQ ID NO: 27 and a light chain variable region sequence of SEQ ID NO: 31; or cross-competes with an antibody comprising a heavy chain variable region sequence of SEQ ID NO: 35 and a light chain variable region sequence of SEQ ID NO: 39.

55. The method of any one of paragraphs 1 to 47 and 49 to 54, further comprising measuring ICOS and/or T-bet levels of CD8+ T cells present in the one or more peripheral blood test samples, wherein a population of CD8+ T cells having elevated ICOS and/or T-bet levels relative to a control is not detected in the samples.

56. The method of any one of paragraphs 1 to 47 and 49 to 55, wherein the cancer is selected from gastric cancer, breast cancer, which optionally is triple negative breast cancer (TNBC), non-small cell lung cancer (NSCLC), melanoma, renal cell carcinoma (RCC), bladder cancer, endometrial cancer, diffuse large B-cell lymphoma (DLBCL), Hodgkin's lymphoma, ovarian cancer, and head and neck squamous cell cancer (HNSCC).

57. The method of any one of paragraphs 1 to 47 and 49 to 56, wherein the subject is a human patient.

58. The method of any one of paragraphs 1 to 5, 10 to 47, and 49 to 57, wherein the population of CD4+ T cells having elevated ICOS and/or T-bet levels comprises a new, separate population of CD4+ T cells, which was induced by the one or more anti-cancer therapies.

59. A method of generating an expanded population of CD4+ T cells having elevated ICOS expression, said method comprising culturing the suspension of CD4+ T cells of paragraph 48 under initial culture conditions suitable for expanding said population of CD4+ T cells.

60. The method of paragraph 59, wherein said initial conditions suitable for expanding said population of CD4+ T cells comprises contacting said suspension of CD4+ T cells with a CD3 agonist.

61. The method of paragraph 60, wherein said CD3 agonist is an anti-CD3 antibody (e.g., OKT3).

62. The method of any one of paragraphs 59-61, wherein said initial conditions suitable for expanding said population of CD4+ T cells comprises contacting said suspension with one or more of an anti-PD-1 antibody antagonist, an anti-CTLA-4 antibody, and an ICOS agonist.

63. The method of any one of paragraphs 59-62, wherein said initial conditions suitable for expanding said population of CD4+ T cells comprises contacting said suspension with one or more compounds (e.g., two or more, or all three) selected from the group consisting of IL-2, IL-12 and anti-IL-4.

64. The method of any one of paragraphs 59-62, wherein said initial conditions suitable for expanding said population of CD4+ T cells comprises contacting said suspension with an anti-CD28 antibody agonist.

65. The method of any one of paragraphs 61-64, wherein said CD3 agonist and anti-CD28 agonist are present in a tetrameric antibody complex.

66. The method of any one of paragraphs 59-65, wherein said suspension of CD4+ T cells are incubated under said initial culture conditions for a period between one and five days (e.g., approximately 1, 2, 3, 4, or five days).

67. The method of paragraph 66, further comprising incubating said suspension of CD4+ T cells under a second culture condition suitable for expanding said population of CD4+ T cells.

68. The method of paragraph 67, wherein said cells are washed prior to the application of said second culture condition.

69. The method of paragraph 67 or 68, wherein said second culture condition comprises contacting said suspension of cells with one or more of an anti-PD-1 antibody antagonist, an anti-CTLA-4 antibody, and an ICOS agonist.

70. The method of any one of paragraphs 67-69, wherein said second culture condition comprises contacting said suspension of cells with one or more compounds (e.g., two or more, or all three) selected from the group consisting of IL-2, IL-12 and anti-IL-4.

71. The method of any one of paragraphs 67-70, wherein said second culture condition comprises contacting said suspension of cells with an anti-CD28 antibody agonist.

72. The method of any one of paragraphs 67-70, wherein said second culture conditions does not comprise contacting said suspension of cells with a CD3 agonist and/or CD28 agonist.

73. The method of any one of paragraphs 67-72, wherein said second culture condition is maintained for between 1 and 5 days (e.g., for 1, 2, 3, 4, or 5 days).

74. A suspension of cells generated by any one of the methods of paragraphs 59-73.

75. A method of treating cancer in a subject in need thereof, the method comprising administering to said patient the suspension of cells of paragraph 74, wherein optionally the suspension of T-cells of paragraph 48 were isolated from said subject.

Other embodiments are within the following claims.

What is claimed is:

1. A method of treating cancer in a subject in need thereof, the method comprising (i) administering one or more dosages of an ICOS agonist to the subject, (ii) after the administration, obtaining one or more peripheral blood test samples from the subject, (iii) measuring ICOS and/or T-bet levels of CD4+T cells present in the one or more peripheral blood test samples, (iv) identifying a population of CD4+T cells having elevated ICOS and/or T-bet levels in any of the one or more peripheral blood test samples when compared to a control, and (v) administering one or more additional dosages of the ICOS agonist to the subject.

2. The method of claim 1, wherein:
   (a) step (iii) comprises measuring ICOS levels of CD4+T cells present in the one or more peripheral blood test samples, step (iv) comprises identifying a population of CD4+T cells having elevated ICOS levels in any one of the one or more peripheral blood test samples when compared to a control, and step (v) comprises administering one or more additional dosages of the ICOS agonist to the subject;
   (b) step (iii) comprises measuring ICOS and T-bet levels of CD4+T cells present in the one or more peripheral blood test samples, step (iv) comprises identifying a population of CD4+T cells having elevated ICOS and T-bet levels in any one of the one or more peripheral blood test samples when compared to a control, and step (v) comprises administering one or more additional dosages of the ICOS agonist to the subject; or
   step (v) comprises administration of an anti-ICOS antibody agonist to the subject.

3. The method of claim 1, wherein the anti-ICOS agonist comprises an anti-ICOS agonist antibody.

4. The method of claim 3, wherein:
the anti-ICOS agonist antibody is selected from the group consisting of JTX-2011, BMS-986226, and GSK3359609.

5. The method of claim 1, wherein the anti-ICOS antibody agonist comprises:
   (i) (a) an HCDR1 comprising the amino acid sequence of SEQ ID NO: 5; (b) an HCDR2 comprising the amino acid sequence of SEQ ID NO: 6; (c) an HCDR3 comprising the amino acid sequence of SEQ ID NO: 7; (d) an LCDR1 comprising the amino acid sequence of SEQ ID NO: 8; (e) an LCDR2 comprising the amino acid sequence of SEQ ID NO: 9; and (f) an LCDR3 comprising the amino acid sequence of SEQ ID NO: 10; or
   (ii) (a) a heavy chain comprising the amino acid sequence of SEQ ID NO: 1 and (b) a light chain comprising the amino acid sequence of SEQ ID NO: 2.

6. The method of claim 1, wherein the ICOS agonist is administered two, three, four, five, or more times prior to obtaining the one or more peripheral blood test samples.

7. The method of claim 1, wherein the obtaining of the one or more peripheral blood test samples is performed fewer than 4, 3, 2, or 1 weeks after the one or more administrations of the dosages of the one or more anticancer therapies.

8. The method of claim 1, wherein the dosage of ICOS agonist is administered multiple times at regular intervals.

9. The method of claim 8, wherein:
   (a) the regular intervals are selected from the group consisting of a dosage every week, a dosage every two weeks, a dosage every three weeks, a dosage every four weeks, a dosage every six weeks, a dosage every nine weeks, and a dosage every twelve weeks;
   (b) the obtaining of the one or more peripheral blood test samples comprises the obtaining of multiple peripheral blood test samples, with test samples being obtained concurrent with one or more of the administrations; or
   (c) the obtaining of the one or more peripheral blood test samples comprises the obtaining of multiple peripheral blood test samples, with test samples being obtained during a time intervening the multiple administrations.

10. The method of claim 1, wherein the method further comprises storing a portion of one or more of the peripheral blood test samples.

11. The method of claim 1, wherein a portion of the CD4+T cells having elevated ICOS and/or T-bet levels is isolated from one or more of the peripheral blood test samples and stored under conditions suitable for maintaining the viability of the CD4+T cells, and optionally:
   (a) the stored CD4+T cells are stored in a cell culture medium;
   (b) the stored CD4+T cells are stored at a concentration of greater than 100,000 cells/mL; or
   (c) the stored CD4+T cells are stored at a concentration between 100,000 cells/mL and 100 million cells/mL.

12. The method of claim 1, wherein the control comprises a peripheral blood test sample, which is optionally obtained from the subject before one or more of the administrations of the ICOS agonist to the subject, or the control comprises a peripheral blood sample obtained from a healthy individual not receiving the ICOS agonist.

13. The method of claim 1, wherein determining of ICOS and/or T-bet levels comprises the use of an immunoassay, and optionally the immunoassay comprises the use of an antibody that binds to an intracellular domain of ICOS to detect ICOS, wherein the antibody optionally: (a) comprises a heavy chain variable region sequence of SEQ ID NO: 27 and a light chain variable region sequence of SEQ ID NO: 31; (b) comprises a heavy chain variable region sequence of SEQ ID NO: 35 and a light chain variable region sequence of SEQ ID NO: 39; (c) cross-competes with an antibody comprising a heavy chain variable region sequence of SEQ ID NO: 27 and a light chain variable region sequence of SEQ ID NO: 31; or (d) cross-competes with an antibody comprising a heavy chain variable region sequence of SEQ ID NO: 35 and a light chain variable region sequence of SEQ ID NO: 39.

14. The method of claim 1, further comprising measuring ICOS and/or T-bet levels of CD8+T cells present in the one or more peripheral blood test samples, wherein a population of CD8+T cells having elevated ICOS and/or T-bet levels relative to a control is not detected in the samples.

15. The method of claim 1, wherein the cancer is selected from gastric cancer, breast cancer, which optionally is triple negative breast cancer (TNBC), non-small cell lung cancer (NSCLC), melanoma, renal cell carcinoma (RCC), bladder cancer, endometrial cancer, diffuse large B-cell lymphoma (DLBCL), Hodgkin's lymphoma, ovarian cancer, and head and neck squamous cell cancer (HNSCC).

16. The method of claim 1, wherein the subject is a human patient.

17. The method of claim 1, wherein the population of CD4+T cells having elevated ICOS and/or T-bet levels comprises a new, separate population of CD4+T cells, which was induced by the ICOS agonist.

18. The method of claim 1, wherein step (iii) comprises measuring T-bet levels of CD4+T cells present in the one or more peripheral blood test samples, step (iv) comprises identifying a population of CD4+T cells having elevated T-bet levels in any one of the one or more peripheral blood test samples when compared to a control, and step (v) comprises administering one or more additional dosages of the ICOS agonist to the subject.

19. The method of claim 1, wherein step (iii) comprises measuring ICOS and T-bet levels of CD4+T cells present in the one or more peripheral blood test samples, step (iv) comprises identifying a population of CD4+T cells having elevated ICOS and T-bet levels in any one of the one or more peripheral blood test samples when compared to a control, and step (v) comprises administering one or more additional dosages of the ICOS agonist to the subject.

\* \* \* \* \*